US011386324B2

(12) United States Patent
Gao et al.

(10) Patent No.: US 11,386,324 B2
(45) Date of Patent: *Jul. 12, 2022

(54) RECURRENT NEURAL NETWORK-BASED VARIANT PATHOGENICITY CLASSIFIER

(71) Applicant: Illumina, Inc., San Diego, CA (US)

(72) Inventors: Hong Gao, Palo Alto, CA (US); Kai-How Farh, San Mateo, CA (US); Laksshman Sundaram, Fremont, CA (US); Jeremy Francis McRae, Hayward, CA (US)

(73) Assignee: Illumina, Inc., San Diego, CA (US)

( * ) Notice: Subject to any disclaimer, the term of this patent is extended or adjusted under 35 U.S.C. 154(b) by 136 days.

This patent is subject to a terminal disclaimer.

(21) Appl. No.: 16/773,678

(22) Filed: Jan. 27, 2020

(65) Prior Publication Data

US 2020/0279157 A1    Sep. 3, 2020

Related U.S. Application Data

(63) Continuation of application No. 16/413,476, filed on May 15, 2019, now Pat. No. 10,558,915, which is a (Continued)

(51) Int. Cl.
*G06K 9/62* (2006.01)
*G06N 3/08* (2006.01)
(Continued)

(52) U.S. Cl.
CPC ............. *G06N 3/08* (2013.01); *G06K 9/6257* (2013.01); *G06K 9/6259* (2013.01);
(Continued)

(58) Field of Classification Search
None
See application file for complete search history.

(56) References Cited

U.S. PATENT DOCUMENTS

| 10,068,557 B1 | 9/2018 | Engel et al. |
| 2013/0110407 A1 | 5/2013 | Baccash et al. |

(Continued)

FOREIGN PATENT DOCUMENTS

| CA | 2894317 A1 | 12/2016 |
| CN | 103679185 A | 3/2014 |

(Continued)

OTHER PUBLICATIONS

AU 2018350891—First Exam Report (Office Action), dated Dec. 4, 2020, 7 pages.

(Continued)

*Primary Examiner* — Sean M Conner
(74) *Attorney, Agent, or Firm* — Haynes Beffel & Wolfeld LLP; Ernest J. Beffel, Jr.; Sikander M. Khan

(57) ABSTRACT

The technology disclosed relates to constructing a convolutional neural network-based classifier for variant classification. In particular, it relates to training a convolutional neural network-based classifier on training data using a backpropagation-based gradient update technique that progressively match outputs of the convolutional neural network-based classifier with corresponding ground truth labels. The convolutional neural network-based classifier comprises groups of residual blocks, each group of residual blocks is parameterized by a number of convolution filters in the residual blocks, a convolution window size of the residual blocks, and an atrous convolution rate of the residual blocks, the size of convolution window varies between groups of residual blocks, the atrous convolution rate varies between groups of residual blocks. The training data includes benign training examples and pathogenic training examples of translated sequence pairs generated from benign variants and pathogenic variants.

16 Claims, 62 Drawing Sheets
(21 of 62 Drawing Sheet(s) Filed in Color)

Related U.S. Application Data continuation of application No. 16/160,903, filed on Oct. 15, 2018, now Pat. No. 10,423,861.

(60) Provisional application No. 62/582,898, filed on Nov. 7, 2017, provisional application No. 62/573,153, filed on Oct. 16, 2017, provisional application No. 62/573,149, filed on Oct. 16, 2017, provisional application No. 62/573,144, filed on Oct. 16, 2017.

(51) Int. Cl.
| | | |
|---|---|---|
| *G06N 7/00* | (2006.01) | |
| *G16B 40/00* | (2019.01) | |
| *G16B 20/00* | (2019.01) | |
| *G16H 70/60* | (2018.01) | |
| *G06N 3/04* | (2006.01) | |

(52) U.S. Cl.
CPC ......... *G06K 9/6267* (2013.01); *G06N 3/0454* (2013.01); *G06N 3/0481* (2013.01); *G06N 3/084* (2013.01); *G06N 7/005* (2013.01); *G16B 20/00* (2019.02); *G16B 40/00* (2019.02); *G16H 70/60* (2018.01); *G06V 2201/03* (2022.01)

(56) References Cited

U.S. PATENT DOCUMENTS

| | | |
|---|---|---|
| 2013/0203053 A1 | 8/2013 | Princen et al. |
| 2013/0296175 A1 | 11/2013 | Rafnar et al. |
| 2015/0337388 A1 | 11/2015 | Gamer, Jr. et al. |
| 2016/0085910 A1 | 3/2016 | Bruand et al. |
| 2016/0196479 A1 | 7/2016 | Chertok et al. |
| 2016/0357903 A1 | 12/2016 | Shendure et al. |
| 2016/0364522 A1 | 12/2016 | Frey et al. |
| 2016/0371431 A1 | 12/2016 | Haque et al. |
| 2017/0169313 A1 | 6/2017 | Choi et al. |
| 2017/0199961 A1 | 7/2017 | Yelensky et al. |
| 2018/0107927 A1 | 4/2018 | Frey |
| 2018/0197067 A1 | 7/2018 | Mody et al. |
| 2018/0322327 A1 | 11/2018 | Smith et al. |

FOREIGN PATENT DOCUMENTS

| | | |
|---|---|---|
| CN | 105378104 A | 3/2016 |
| JP | 2002505741 | 2/2002 |
| JP | 2003527698 A | 9/2003 |
| JP | 200752774 A | 3/2007 |
| JP | 2012504761 A | 2/2012 |
| JP | 2015501974 A | 1/2015 |
| JP | 2017111830 A | 6/2017 |
| JP | 2017520821 A | 7/2017 |
| JP | 2018527647 A | 9/2018 |
| RU | 2470998 C2 | 12/2012 |
| WO | 2015173222 A1 | 11/2015 |
| WO | 2016061396 A1 | 4/2016 |
| WO | 2016145516 A1 | 9/2016 |
| WO | 2016201049 A2 | 12/2016 |
| WO | 2016201564 A1 | 12/2016 |
| WO | 2016209999 A1 | 12/2016 |
| WO | 2017172958 A1 | 10/2017 |
| WO | 2019136284 A1 | 7/2019 |
| WO | 2019140402 A1 | 7/2019 |

OTHER PUBLICATIONS

CN201880043817.3—First Office Action dated Aug. 3, 2020, 26 pages.
AU 2018352203—First Exam Report dated Jun. 16, 2020, 4 pages.
JP 2019567719—Notice of Allowance dated Jan. 4, 2021, 3 pages.
MYPI2019007296—First Office Action dated Aug. 27, 2020, 3 pages.
MYPI2019007296—Response to First Office Action, filed Oct. 27, 2020, 10 pages.
MYPI2019007296—Substantive Examination Clear Report dated Feb. 5, 2021, 2 pages.
AU 2018352201—First Office Action, dated Dec. 4, 2020, 7 pages.
AU 2018352201—Voluntary Amendment filed on Nov. 24, 2020, 257 pages.
CN-2018800438309 Voluntary Amendment filed Jun. 28, 2020, 29 pages including English translation.
EP 18799923.0—Response to Rule 161(1) and 162 communication dated Jan. 24, 2020, filed Aug. 3, 2020, 20 pages.
EP 18799923.0—Rule 161(1) and 162 communication dated Jun. 24, 2020, 3 pages.
EP 18796339.2—Response to Rule 161(1) and 162 communication dated Jan. 3, 2020, filed Jul. 8, 2020, 13 pages.
EP 18796339.2—Rule 161(1) and 162 communication dated Jan. 3, 2020, 3 pages.
PCT/US2018/055840 Second and Supplementary Notice informing the Applicant of the Communication of the International Application dated Feb. 20, 2020. 1 page.
CN201880043817 Notice of Allowance dated Jan. 8, 2021, 1 page.
IL2018271121, Notice of Acceptance, dated Feb. 16, 2021, 03 pages.
KR 10-2019-7036421 Notice of Issue dated Dec. 22, 2020, 2 pages.
KR 10-2019-7036421 Notice of Allowance dated Sep. 22, 2020, 3 pages.
KR 10-2019-7036421 First Office Action dated May 11, 2020, 8 pages.
KR 10-2019-7036421 Response to First Office Action dated May 11, 2020, 29 pages.
EP 18796330.1 Response to Rule 161(1) and 162 EPC dated Sep. 23, 2020, filed Apr. 6, 2021, 11 pages.
PCT/US2018/055840 Voluntary Amendment dated Dec. 24, 2019, 7 pages.
SG11201912966U Request for Examination dated Dec. 26, 2019, 4 pages.
ZA2019/08141 VoluntaryAmendment dated Dec. 9, 2019, 13pages.
IL 271119 Response to Notice Before Examination, filed Feb. 28, 2021, 5 pgs.
JP2019-567721 First Office Action dated Mar. 8, 2021, 8 pages.
JP2019567720 First Office Action dated Mar. 8, 2021, 12 pages.
Stanescu et. al., "An empirical study of ensemble-based semi-supervised learning approaches for imbalanced splice site datasets", BMC Systems Biology, dated Sep. 1, 2015, vol. 9, Article S1, pp. 1-12.
JP2019567720 Voluntary Amendments, dated Oct. 14, 2020, 6pgs.
KR 1020197036423 First Office Action, dated Feb. 25, 2021, 12 pages.
ZA2019/08142 Voluntary Amendment, dated Jul. 17, 2020, 13 pages.
KR1020197036423 Voluntary Amendment, dated Nov. 6, 2020, 13 pages.
SG11201912740T Voluntary Amendment and Request for Search and Exam dated Oct. 16, 2020, 36pgs, based on PCT/US2018/055878.
NZ 759804 First Office Action dated May 5, 2021, 3 pages.
SG 11201912966U Response to Written Opinion, filed May 17, 2021, 19 pages.
SG 11201912966U Examination Report and Grant Fee, dated May 27, 2021, 7 pages.
SG 11201912966U Written Opinion, dated Dec. 11, 2020, 7 pages.
KR 10-2019-7036422 First Office Action, dated Apr. 29, 2021, 8 pages.
NZ 759813 First Office Action, dated May 11, 2021, 4 pages.
NZ 759818 First Office Action, dated Apr. 29, 2021, 3 pages.
IL 283107 Notice Before Examination, dated May 13, 2021, 2 pages.
KR 10-2019-7036423 Response to First Office Action dated Feb. 25, 2021, filed Apr. 26, 2021, 37 pages.
KR 10-2019-7036423 Notice of Allowance, dated Jul. 9, 2021, 3 pages.

(56) References Cited

OTHER PUBLICATIONS

Karydis, Thrasyvoulos. "Learning hierarchical motif embeddings for protein engineering." PhD diss., Massachusetts Institute of Technology, Feb. 2017, 78 pages.
Lanchantin J, Sekhon A, Singh R, Qi Y. Prototype Matching Networks for Large-Scale Multi-label Genomic Sequence Classification, ArXiv 1710.11238v1 [cs LG],Oct. 30, 2017, 17 pgs.
Fu H, Yang L, Zhang X. Noncoding variants functional prioritization methods based on predicted regulatory factor binding sites, Current Genomics, 2017, vol. 18, pp. 322-331.
Wang D, Lee NK. MISCORE: Mismatch-based matrix similarity scores for DNA motif detection. In International Conference on Neural Information Processing Nov. 25, 2008 (pp. 478-485). Springer, Berlin, Heidelberg. (Year: 2008).
Chen LC et al, Deeplab—Semantic image segmentation with deep convolutional nets, Atrous convolution, and fully connected crfs. IEEE transactions on pattern analysis and machine intelligence. Apr. 27, 2017;40(4):834-48. (Year: 2017).
PCT/US2018/055881—International Search Report and Written Opinion dated Feb. 1, 2019, 17 pages.
U.S. Appl. No. 16/160,903—Notice of Allowance dated Apr. 19, 2019, 28 page.
RU 2019139312 First Office Action, dated Aug. 3, 2021, 10 pages.
CA 3066775 First Office Action, dated Mar. 10, 2021, 4 pages.
CA 3066775 Response to First Office Action dated Mar. 10, 2021, filed Jul. 9, 2021, 42 pages.
JP 2019-567720 Response to First Office Action dated Mar. 8, 2021, filed Jun. 8, 2021, 9 pages.
JP 2019-567720 Notice of Allowance, dated Sep. 13, 2021, 6 pages.
JP 2019-567721 Response to Office Action dated Mar. 8, 2021, filed Jun. 8, 2021, 10 pages.
JP 2019-567721 Notice of Allowance, dated Sep. 13, 2021, 6 pages.
AU 2018350891 Voluntary Amendments, dated Nov. 25, 2020, 4 pages.
BR 1120190274804 First Office Action, dated Sep. 6, 2021, 12 pages.
EP 18796330.1 Rule 161(1) and 162 EPC Communication, dated Sep. 23, 2020, 3 pages.
IL 271121, Response to Notice Before Examination, dated Feb. 1, 2021, 5 pages.
IL 283107 Response to Notice Before Examination dated May 13, 2021, filed Aug. 29, 2021, 5 pages.
JP 2019567719 Response to First Office Action, filed Oct. 27, 2020, 14 pages.
MY 2019007229 Response to Preliminary Exam, dated Oct. 15, 2020, 11 pages.
SG 11201912740T Search Report and Written Opinion, dated Oct. 20, 2021, 12 pages.
KR 10-2019-7036422 Response to First Office Action dated Apr. 29, 2021, filed Jul. 28, 2021, 28 pages.
AU 2018352203—Response to First Office Action dated Jun. 16, 2020, filed Aug. 16, 2021, 233 pages.
AU 2018352203 Notice of Acceptance, dated Sep. 21, 2021, 3 pages.
IL 271119 Notice Before Exam (in Hebrew), dated Sep. 29, 2020, 2 pages.
IL 271121 Notice before Exam (in Hebrew), dated Sep. 29, 2020, 2 pages.
Sundaram L. et al., "Predicting the clinical impact of human mutation with deep neural networks," Nature genetics 50, No. 8 (2018): pp. 1161-1173.
Krizhevsky, Alex, et al., ImageNet Classification with Deep Convolutional Neural Networks, 2012, 9 Pages.
Geeks for Geeks, "Underfitting and Overfitting in Machine Learning", [retrieved on Aug. 26, 2019], Retrieved from the Internet <https://www.geeksforgeeks.org/underfitting-and-overfitting-in-machine-learning/>, 2 pages.
Despois, Julien, "Memorizing is not learning!—6 tricks to prevent overfitting in machine learning", Mar. 20, 2018, 17 pages.
Bhande, Anup What is underfilling and overfitting in machine learning and how to deal with it, Mar. 11, 2018, 10pages.
U.S. Appl. No. 16/407,149—Notice of Allowance dated Sep. 5, 2019, 26 pages.
Li, Gangmin, et. al., "Classification of Genetic Mutations for Cancer Treatment with Machine Learning Approaches", International Journal of Design, Analysis and Tools for Integrated Circuits and Systems, vol. 7, No. 1, Oct. 1, 2018, pp. 63-66.
KR 10-2019-7038080—First Office Action dated Apr. 10, 2020.
AU 2019272062—First Office Action dated Sep. 2, 2020, 4 pages.
CN-201980003263.9—First Office Action dated Dec. 24, 2020, 18 pages with English translation.
CN-201980003263.9—Voluntary Amendment filed Aug. 28, 2020, 10 pages.
CA 3064223 First Office Action, dated Mar. 16, 2021, 5 pages.
CN 2019800032639 Response to First Office Action, dated Apr. 20, 2021, 4 pages.
IL 271091 Notice Before Examination, dated Sep. 22, 2020, 2 pages.
IL 271091 Response to Notice Before Examination and PPH Request, dated Jan. 21, 2021, 274 pages.
IL 271091 Notice Before Acceptance, dated Jan. 26, 2021, 60 pages.
JP 2019-567603 First Office Action, dated Jan. 4, 2021, 7 pages.
JP 2019-567603 Response to First Office Action, response dated Apr. 5, 2021, 9 pages.
JP 2019-567603 Notice of Allowance, dated Apr. 19, 2021, 3 pages.
KR 10-2019-7038080 Response to First Office Action, response dated Jun. 10, 2020, 19 pages.
KR 10-2019-7038080 Notice of Allowance, dated Jul. 7, 2020, 5 pages.
SG 11201911777Q Written Opinion, dated Dec. 17, 2020, 6 pages.
SG 11201911777Q Response to Written Opinion, dated May 17, 2021, 18 pages.
SG 112019117770 Exam Report, dated May 20, 2021, 5 pages.
EP 19729404.4 First Office Action—Article 94(3), dated May 18, 2021, 5 pages.
NZ 759665 First Office Action, dated Jun. 9, 2021, 4 pages.
CN 2019800032639 Notice of Allowance, dated Jul. 13, 2021, 4 pages.
EP 19729404.4 First Office Action, dated May 18, 2021, 5 pages.
EP 19729404.4 Voluntary Amendment Rule 161(1), dated May 11, 2020, 3 pages.
EP 19729404.4 Response to Rule 161(1) and 162, dated Nov. 23, 2020, 12 pages.
AU 2019272062—Response to First Office Action dated Sep. 3, 2020, filed Jul. 23, 2021, 86 pages.
AU 2019272062—Notice of Acceptance, dated Aug. 10, 2021, 3 pages.
CA 3064223 Response to First Office Action, dated Mar. 16, 2021, filed Sep. 16, 2021, 32 pages.
IL 282689, Notice before Examination (Hebrew version), dated Apr. 29, 2021, 2 pages.
IL 282689 Response to Notice Before Examination dated Apr. 29, 2021, filed Aug. 29, 2021, 5 pages.
AU 2018350891 Response to Office Action dated Dec. 4, 2020, filed Oct. 21, 2021, 237 pages.
Macarthur, D. G. et al. Guidelines for investigating causality of sequence variants in human disease. Nature 508, 469-476 (2014).
Rehm, H. L. et al. ClinGen—the Clinical Genome Resource. N. Engl. J. Med. 372, 2235-2242 (2015).
Bamshad, M. J. et al. Exome sequencing as a tool for Mendelian disease gene discovery. Nat. Rev. Genet. 12, 745-755 (2011).
Rehm, H. L. Evolving health care through personal genomics. Nat. Rev. Genet. 18, 259-267 (2017).
Richards, S. et al. Standards and guidelines for the interpretation of sequence variants: a joint consensus recommendation of the American College of Medical Genetics and Genomics and the Association for Molecular Pathology. Genet. Med. 17, 405-424 (2015).
Lek, M. et al. Analysis of protein-coding genetic variation in 60,706 humans. Nature 536, 285-291 (2016).
Mallick, S. et al. The Simons Genome Diversity Project: 300 genomes from 142 diverse populations. Nature 538, 201-206 (2016).

(56) References Cited

OTHER PUBLICATIONS

Genomes Project Consortium, et al. A global reference for human genetic variation. Nature 526, 68-74 (2015).
Liu, X., Jian, X. & Boerwinkle, E. dbNSFP: a lightweight database of human nonsynonymous SNPs and their functional predictions. Human. Mutat. 32, 894-899 (2011).
Chimpanzee Sequencing Analysis Consortium. Initial sequence of the chimpanzee genome and comparison with the human genome. Nature 437, 69-87 (2005).
Takahata, N. Allelic genealogy and human evolution. Mol. Biol. Evol. 10, 2-22 (1993).
Asthana, S., Schmidt, S., & Sunyaev, S. A limited role for balancing selection. Trends Genet. 21, 30-32 (2005).
Leffler, E. M. et al. Multiple instances of ancient balancing selection shared between humans and chimpanzees. Science 339, 12 pages (2013).
Samocha, K. E. et al. A framework for the interpretation of de novo mutation in human disease. Nat. Genet. 46, 944-950 (2014).
Ohta, T. Slightly deleterious mutant substitutions in evolution. Nature 246, 96-98 (1973).
Reich, D. E. & Lander, E. S. On the allelic spectrum of human disease. Trends Genet. 17, 502-510 (2001).
Whiffin, N. et al. Using high-resolution variant frequencies to empower clinical genome interpretation. Genet. Med. 19, 1151-1158 (2017).
Prado-Martinez, J. et al. Great ape genome diversity and population history. Nature 499, 471-475 (2013).
Klein, J., Satta, Y., O'HUigin, C., & Takahata, N. The molecular descent of the major histocompatibility complex. Annu. Rev. Immunol. 11, 269-295 (1993).
De Manuel, M. et al. Chimpanzee genomic diversity reveals ancient admixture with bonobos. Science 354, 477-481 (2016).
Locke, D. P. et al. Comparative and demographic analysis of orang-utan genomes. Nature 469, 529-533 (2011).
Rhesus Macaque Genome Sequencing Analysis Consortium. Evolutionary and biomedical insights from the rhesus macaque genome. Science 316, 222-234 (2007).
Worley, K. C. et al. The common marmoset genome provides insight into primate biology and evolution. Nat. Genet. 46, 850-857 (2014).
Sherry, S. T. et al. dbSNP: the NCBI database of genetic variation. Nucleic Acids Res. 29, 308-311 (2001).
Schrago, C. G., & Russo, C. A. Timing the origin of New World monkeys. Mol. Biol. Evol. 20, 1620-1625 (2003).
Landrum, M. J. et al. ClinVar: public archive of interpretations of clinically relevant variants. Nucleic Acids Res. 44, D862-868 (2016).
Brandon, E. P., Idzerda, R. L. & McKnight, G. S. Targeting the mouse genome: a compendium of knockouts (Part II). Curr. Biol. 5, 758-765 (1995).
Lieschke, J. G. & Currie, P. D. Animal models of human disease: zebrafish swim into view. Nat. Rev. Genet. 8, 353-367 (2007).
Sittig, L. J. et al. Genetic background limits generalizability of genotype-phenotype relationships. Neuron 91, 1253-1259 (2016).
Bazykin, G. A. et al. Extensive parallelism in protein evolution. Biol. Direct 2, 20, 13 pages (2007).
Ng, P. C., & Henikoff, S. Predicting deleterious amino acid substitutions. Genome Res. 11, 863-874 (2001).
Adzhubei, I. A et al. A method and server for predicting damaging missense mutations. Nat. Methods 7, 248-249 (2010).
Chun, S. & Fay, J. C. Identification of deleterious mutations within three human genomes. Genome Res. 19, 1553-1561 (2009).
Schwarz, J. M., Rodelsperger, C., Schuelke, M. & Seelow, D. MutationTaster evaluates disease-causing potential of sequence alterations. Nat. Methods 7, 575-576 (2010).
Reva, B., Antipin, Y., & Sander, C. Predicting the functional impact of protein mutations: application to cancer genomics. Nucleic Acids Res 39, e118 (2011), 14pgs.
Dong, C. et al. Comparison and integration of deleteriousness prediction methods for nonsynonymous SNVs in whole exome sequencing studies. Hum. Mol. Genet. 24, 2125-2137 (2015).
Carter, H., Douville, C., Stenson, P. D., Cooper, D. N., & Karchin, R. Identifying Mendelian disease genes with the variant effect scoring tool. BMC Genom, (2013), 13 pages.
Choi, Y., Sims, G. E., Murphy, S., Miller, J. R., & Chan, A. P. Predicting the functional effect of amino acid substitutions and indels. PLoS One 7, e46688 (2012).
Gulko, B., Hubisz, M. J., Gronau, I., & Siepel, A. A method for calculating probabilities of fitness consequences for point mutations across the human genome. Nat. Genet. 47, 276-283 (2015).
Shihab, H. A. et al. An integrative approach to predicting the functional effects of non-coding and coding sequence variation. Bioinformatics 31, 1536-1543 (2015).
Quang, D., Chen, Y., & Xie, X. "DANN: a deep learning approach for annotating the pathogenicity of genetic variants", Bioinformatics 31, 761-763 (2015).
Bell, C. J. et al. Comprehensive carrier testing for severe childhood recessive diseases by next generation sequencing. Sci. Transl. Med. 3, Jan. 12, 2011, 28 pages.
Kircher, M. et al. A general framework for estimating the relative pathogenicity of human genetic variants. Nat. Genet. 46, 310-315 (2014).
Smedley, D. et al. A whole-genome analysis framework for effective identification of pathogenic regulatory variants in mendelian disease. Am. J. Hum. Genet. 99, 595-606 (2016).
Iannidis, N. M. et al. REVEL: an ensemble method for predicting the pathogenicity of rare missense variants. Am. J. Hum. Genet. 99, 877-885 (2016).
Jagadeesh, K. A. et al. M-CAP eliminates a majority of variants of uncertain significance in clinical exomes at high sensitivity. Nat. Genet. 48, 1581-1586 (2016).
Grimm, D. G. The evaluation of tools used to predict the impact of missense variants is hindered by two types of circularity. Human. Mutat. 36, 513-523 (2015).
Heffernan, R. et al. Improving prediction of secondary structure, local backbone angles, and solvent accessible surface area of proteins by iterative deep learning. Sci. Rep. 5, 11476 (2015), 11 pages.
Wang, S., Peng, J., Ma, J. & Xu, J. Protein secondary structure prediction using deep convolutional neural fields. Sci. Rep. 6, 18962-18962 (2016).
Harpak, A., Bhaskar, A., & Pritchard, J. K. Mutation rate variation is a primary determinant of the distribution of allele frequencies in humans. PLoS Genet. Dec. 15, 2016, 22pgs.
Leung, et. al., "Deep learning of the tissue regulated splicing code", 2014, 9pgs.
Leung, et. al., "Inference of the Human Polyadenylation Code", Apr. 27, 2017, 13pgs.
Leung, et. al., "Machine Learning in Genomic Medicine", Jan. 1, 2016, 22pgs.
Park, et. al., "Deep Learning for Regulatory Genomics", Aug. 2015, 2pgs.
Piqueras Autoregressive model based on a deep CNN for audio generation, Mar. 2017, 58pgs.
Srivastava, et. al., "Highway Networks", Nov. 3, 2015 6pgs.
Sundaram, et. al., "Predicting the clinical impact of human mutation with deep neural networks", Aug. 2018, 15pgs.
Szegedy, et. al., "Going deeper with convolutions", Sep. 17, 2014, 12pgs.
Van Den Oord, et. al.,"WaveNet: A Generative Model for Raw Audio", Sep. 19, 2016, 15 pgs.
Wolterink, et. al., "Dilated Convolutional Neural Networks for Cardiovascular MR Segmentation", Apr. 12, 2017, 9pgs.
Wu "Intro to CNN", May 1, 2017, 31 pgs.
Xiong, et. al., "The human splicing code reveals new insights into the genetic determinants of disease", Jan. 9, 2015, 20pgs.
Yue, et. al., "Deep Learning for Genomics:A Concise Overview from internet", May 8, 2018, 40pgs.
Yuen, et. al., "Genome wide characteristics of de novo mutations in autism", Jun. 13, 2016, 10pgs.
Yu, et al., "Multi Scale Context Aggregation by Dilated Convolutions", Apr. 30, 2016, 13pgs.
Libbrecht, et al., "Machine learning in genetics and genomics", Jan. 2, 2017, 30pgs.

(56) References Cited

OTHER PUBLICATIONS

Min, et. al., "Deep Learning in Bioinformatics", Jul. 25, 2016, 46pgs.
Torng, Wen, et al., "3D deep convolutional neural networks for amino acid environment similarity analysis", 2017, 23pages.
Chen, Kathleen M., et. al., "Selene: a PyTorch based deep learning library for sequence level data", Oct. 10, 2018, 15pages.
Grob, C., et. al., "Predicting variant deleteriousness in non human species Applying the CADD approach in mouse", 2018, 11 pages.
Li, et. al., "FoldingZero: Protein Folding from Scratch in Hydrophobic Polar Model", Dec. 3, 2018, 10 pages.
Rentzsch, et. al., "CADD: predicting the deleteriousness of variants throughout the human genome", Oct. 11, 2018, 9 pages.
Zou, etal, "A primer on deep learning in genomics", Nov. 26, 2018, 7pages.
Alberts, Bruce, et al., "Molecular biology of the cell", Sixth Edition, 2015, 3 pages.
U.S. Appl. No. 16/160,903—Notice of Allowance dated Dec. 28, 2018, 47 page.
PCT/US2018/055840—International Search Report and Written Opinion dated Jan. 25, 2019, 18 pages.
Wei etal_The Role of Balanced Training and Testing Data Sets for Binary Classifiers in Bioinformatics dated Jul. 9, 2013 12 pages.
PCT/US2018/055878—International Search Report and Written Opinion dated Jan. 22, 2019, 20 pages.
Duggirala, Ravindranath, et.al.,"Genome Mapping and Genomics in Human and Non Human Primate", 2015, 306pgs.
Brookes, Anthony J., "The essence of SNPs", 1999, pp. 177-186.
UniProtKB P04217 A1BG Human [retrieved on Mar. 13, 2019], Retrieved from the Internet <https://www.uniprot.org/uniprot/P04217>, 12pages.
Bahar, Protein Actions Principles and Modeling, Chapter 7, 2017 pp. 165-166.
Dunbrack, Roland L., Re: Question about your Paper titled "The Role of Balanced Training and Testing Data Sets for Binary Classifiers in Bioinformatics", Message to Sikander Mohammed Khan, Feb. 3, 2019, E-mailm, 3pgs.
DbSNP rs2241788 [Retrieved on Mar. 13, 2019], Retrieved from the Internet<https://www.ncbi.nlm.nih.gov/snp/rs2241788>, 5 pages.
Wei, et. al., "Prediction of phenotypes of missense mutations in human proteins from biological assemblies", Feb. 2013, 28 pages.
Ioffe et al., Batch Normalization: Accelerating Deep Network Training: Mar. 2, 2015_11pgs.
Darter et al., "Cancer-specific high-throughput annotation of somatic mutations: computational prediction of driver missense mutations," Cancer research 69, No. 16 (2009): pp. 6660-6667.
PCT/US2019/031621—International Search Report and Written Opinion dated Aug. 7, 2019, 17 pages.
Bi, Yingtao, et al. "Tree-based position weight matrix approach to model transcription factor binding site profiles", PloS one 6(9), Sep. 2, 2011, 14 pages.
Chang, Chia-Yun, et al. "Oversampling to overcome overfilling: exploring the relationship between data set composition, molecular descriptors, and predictive modeling methods", Journal of chemical information and modeling, 53, Mar. 6, 2013, pp. 958-971.
Gao, Tingting, et al. "Identifying translation initiation sites in prokaryotes using support vector machine," Journal of theoretical biology, 262, Oct. 17, 2010, 644-649.
Korhonen, Janne H., et al., "Fast motif matching revisited: high-order PWMs, SNPs and indels", Bioinformatics, 33 (4), Dec. 5, 2016, pp. 514-521.
Martin-Navarro, Antonio, et al., "Machine learning classifier for identification of damaging missense mutations exclusive to human mitochondrial DNA-encoded polypeptides", BMC bioinformatic, 18:158, (2017), 12 pages.
Wong, Sebastien C., et al., "Understanding data augmentation for classification: when to warp?", International Conference on Digital Image Computing: Techniques and Applications (DICTA). IEEE, 2016, 6 pages.

Zhang, Jun, et. al.. "PSFM-DBT: identifying DNA-binding proteins by combing position specific frequency matrix and distance-bi gram transformation", International journal of molecular sciences, 18, Jul. 29, 2017, 16 pages.
PCT/US2018/055881—Amendment Under Article 34 dated Oct. 12, 2019, 25 pages.
Reed, et. al., "Training Deep Neural Networks on Noisy Labels with Bootstrapping", 2015, 11 pages.
PCT/US2018/055840—Amendment Under Article 34 dated Aug. 10, 2019, 18 pages.
PCT/US2018/055878—Amendment Under Article 34 dated Aug. 10, 2019, 36 pages.
Payandeh, J., Scheuer, T., Zheng, N. & Catterall, W. A. The crystal structure of a voltage-gated sodium channel. Nature 475, 353-358 (2011).
Shen, H. et al. Structure of a eukaryotic voltage-gated sodium channel at near-atomic resolution. Science 355, eaal4326 (2017), 19 pages.
Nakamura, K. et al. Clinical spectrum of SCN2A mutations expanding to Ohtahara syndrome. Neurology 81, 992-998 (2013).
Henikoff, S. & Henikoff, J. G. Amino acid substitution matrices from protein blocks. Proc. Natl. Acad. Sci. USA 89, 10915-10919 (1992).
Li, W. H., Wu, C. I. & Luo, C. C. Nonrandomness of point mutation as reflected in nucleotide substitutions in oseudogenes and its evolutionary implications. J Molec. Evol. 21, 58-71 (1984).
Grantham, R. Amino acid difference formula to help explain protein evolution. Science 185, 862-864 (1974).
LeCun, Y., Bottou, L., Bengio, Y., & Haffner, P. Gradient based learning applied to document recognition. Proc. IEEE 86, 2278-2324 (1998).
Vissers, L. E., Gilissen, C., & Veltman, J. A. Genetic studies in intellectual disability and related disorders. Nat. Rev. Genet. 17, 9-18 (2016).
Neale, B. M. et al. Patterns and rates of exonic de novo mutations in autism spectrum disorders. Nature 485, 242-245 (2012).
Sanders, S. J. et al. De novo mutations revealed by whole-exome sequencing are strongly associated with autism. Nature 485, 237-241 (2012).
De Rubeis, S. et al. Synaptic, transcriptional and chromatin genes disrupted in autism. Nature 515, 209-215 (2014).
Deciphering Developmental Disorders Study. Large-scale discovery of novel genetic causes of developmental disorders. Nature 519, 223-228 (2015).
Deciphering Developmental Disorders Study. Prevalence and architecture of de novo mutations in developmental disorders. Nature 542, 433-438 (2017).
Iossifov, I. et al. The contribution of de novo coding mutations to autism spectrum disorder. Nature 515, 216-221 (2014).
Zhu, X., Need, A. C., Petrovski, S. & Goldstein, D. B. One gene, many neuropsychiatric disorders: lessons from Mendelian diseases. Nat. Neurosci. 17, 773-78, (2014).
Leffler, E. M. et al. Revisiting an old riddle: what determines genetic diversity levels within species? PLoS Biol. 10, e1001388 (2012), 9 pgs.
Estrada, A. et al. Impending extinction crisis of the worid's primates: why primates matter. Sci. Adv. 3, e1600946 (2017), 17 pages.
Kent, W. J. et al. The human genome browser at UCSC. Genome Res. 12, 996-1006 (2002).
Tyner, C. et al. The UCSC Genome Browser database: 2017 update. Nucleic Acids Res. 45, D626-D634 (2017).
Kabsch, W., & Sander, C. Dictionary of protein secondary structure: pattern recognition of hydrogen-bonded and geometrical features. Biopolymers 22, 2577-2637 (1983).
Joosten, R. P. et al. A series of PDB related databases for everyday needs. Nucleic Acids Res. 39, 411-419 (2011).
He, K., Zhang, X., Ren, S., & Sun, J. Identity mappings in deep residual networks, in 14th European Conference on Computer Vision—ECCV 2016. ECCV 2016. Lecture Notes in Computer Science, vol. 9908; 630-645 (Springer, Cham, Switzerland; 2016).

(56) References Cited

OTHER PUBLICATIONS

Ionita-Laza, I., McCallum, K., Xu, B., & Buxbaum, J. D. A spectral approach integrating functional genomic annotations for coding and noncoding variants. Nat. Genet. 48, 214-220 (2016).
Li, B. et al. Automated inference of molecular mechanisms of disease from amino acid substitutions. Bioinformatics 25, 2744-2750 (2009).
Lu, Q. et al. A statistical framework to predict functional non-coding regions in the human genome through integrated analysis of annotation data. Sci. Rep. 5, 10576 (2015), 13 pgs.
Shihab, H. A. et al. Predicting the functional, molecular, and phenotypic consequences of amino acid substitutions using hidden Markov models. Human. Mutat. 34, 57-65 (2013).
Davydov, E. V. et al. Identifying a high fraction of the human genome to be under selective constraint using GERP++. PLoS Comput. Biol. 6, Dec. 2, 2010, 13 pages.
Liu, X., Wu, C., Li, C., & Boerwinkle, E. dbNSFPv3.0: a one-stop database of functional predictions and annotations for human nonsynonymous and splice-site SNVs. Human. Mutat. 37, 235-241 (2016).
Jain, S., White, M., Radivojac, P. Recovering true classifier performance in positive-unlabeled learning, in Proceedings Thirty-First AAAI Conference on Artificial Intelligence. 2066-2072 (AAAI Press, San Francisco; 2017).
De Ligt, J. et al. Diagnostic exome sequencing in persons with severe intellectual disability. N. Engl. J. Med. 367, 1921-1929 (2012).
Iossifov, I. et al. De novo gene disruptions in children on the autistic spectrum. Neuron 74, 285-299 (2012).
O'Roak, B. J. et al. Sporadic autism exomes reveal a highly interconnected protein network of de novo mutations. Nature 485, 246-250 (2012).
Rauch, A. et al. Range of genetic mutations associated with severe non-syndromic sporadic intellectual disability: an exome sequencing study. Lancet 380, 1674-1682 (2012).
Epi, K. C. et al. De novo mutations in epileptic encephalopathies. Nature 501, 217-221 (2013).
EuroEPINOMICS-RES Consortium, Epilepsy Phenome/Genome Project, Epi4K Consortium. De novo mutations in synaptic transmission genes including DNM1 cause epileptic encephalopathies. Am. J. Hum. Genet. 95, 360-370 (2014).
Gilissen, C. et al. Genome sequencing identifies major causes of severe intellectual disability. Nature 511, 344-347 (2014).
Lelieveld, S. H. et al. Meta-analysis of 2,104 trios provides support for 10 new genes for intellectual disability. Nat. Neurosci. 19, 1194-1196 (2016).
Famiglietti, M. L. et al. Genetic variations and diseases in UniProtKB/Swiss-Prot: the ins and outs of expert manual curation. Human. Mutat. 35, 927-935 (2014).
Horaitis, O., Talbot, C. C.Jr., Phommarinh, M., Phillips, K. M., & Cotton, R. G. A database of locus-specific databases. Nat. Genet. 39, 425 (2007).
Stenson, P. D. et al. The Human Gene Mutation Database: building a comprehensive mutation repository for clinical and molecular genetics, diagnostic testing and personalized genomic medicine. Hum. Genet. 133, 1-9 (2014).
Alipanahi, et. al., "Predicting the Sequence Specificities of DNA and RNA Binding Proteins by Deep Learning", Aug. 2015, 9pgs.
Angermueller, et. al., "Accurate Prediction of Single Cell DNA Methylation States Using Deep Learning", Apr. 11, 2017, 33pgs.
Angermueller, et. al., "Deep Learning for Computational Biology", 2016, 16pgs.
Arik, et. al., "Deep Voice: Real time Neural Text to Speech", Mar. 7, 2017, 17pgs.
Ching, et. al., "Opportunities and Obstacles for Deep Learning in Biology and Medicine", Jan. 19, 2018, 123pgs.
Ching, et. al., "Opportunities and Obstacles for Deep Learning in Biology and Medicine", May 26, 2017, 47pgs.
Goodfellow, et. al., "Deep Learing Chapter 9 Convolutional Networks", 2016, 41 pgs.
Gu, et. al., "Recent Advances in Convolutional Neural Networks", Jan. 5, 2017, 37pgs.
He, et. al., "Deep Residual Learning for Image Recognition", Dec. 10, 2015, 12pgs.
Huang, et. al., "Densely Connected Convolutional Networks", Aug. 27, 2017, 9pgs.
PCT/US2018/055881—Amendment Under Article 34 dated Dec. 12, 2019, 41 pages.
PCT/US2018/055878—International Preliminary Report on Patentability dated Jan. 22, 2020, 38 pages.
PCT/US2018/055840—International Preliminary Reporton Patentability dated Jan. 20, 2020, 26 pages.
PCT/US2018/055881—International Preliminary Report on Patentabiity dated Jan. 28, 2020, 40 pages.
Stanescu, et al., "Ensemble-based semi-supervised learning approaches for imbalanced splice site datasets," In 2014 IEEE International Conference on Bioinformatics and Biomedicine (BIBM), pp. 432-437. IEEE, 2014.
Prakash et al., "A survey on semi-supervised learning techniques." arXiv preprint arXiv:1402.4645, 8 pages (2014).
Karczewski et al., "The Genome Aggregation Database (gnomAD)." MacArthur Lab (2017), 19 pages.
Vikram et al., "SSCM: A method to analyze and predict the pathogenicity of sequence variants." bioRxiv (2015): 021527, 30 pages.
Zhang et al., "Discerning novel splice junctions derived from RNA-seq alignment: A deep learning approach." BMC genomics 19, No. 1 (2018): 971.
Eigen, Columbia University 2015, http://www.columbia.edu/~ii2135/information_eigen.html, accessed Dec. 19, 2018, 1 page.
PCT/US2018/055878—Amendment Under Article 34 dated Mar. 26, 2019, 44 pages.
PCT/US2018/055878—Amendment Under Article 34 dated Dec. 13, 2019, 31 pages.
JP 2019-567719—First Office Action dated Jul. 27, 2020, 5 pages.
U.S. Appl. No. 16/160,986 Notice of Allowance, dated Jul. 23, 2021, 49 pages.
SG 11201912740T International Search Report and Written Opinion, dated Oct. 21, 2021, 13 pages.
AU 2018352201 Response to Office Action, filed Oct. 21, 2021, 243 pages.
RU 2019139312—Response to First Office Action dated Aug. 4, 2021, filed Nov. 4, 2021, 16 pages.
AU 2018350891 Second Office Action dated Nov. 16, 2021, 3 pages.
AU 2018350891 Response to Second Office Action dated Nov. 16, 2021, filed Nov. 22, 2021, 222 pages.
NZ 759818 Response to Office Action, filed Nov. 26, 2021, 14 pages.
IL 283107 First Office Action dated Oct. 27, 2021, 5 pages.
NZ 759804 Response to Office Action, filed Dec. 2, 2021, 13 pages.
NZ 759813 Response to Office Action, filed Dec. 10, 2021, 138 pages.
JP 2019-547220—Office Action dated Nov. 15, 2021, 8 pages.
U.S. Appl. No. 16/160,986-Notice of Allowance dated Dec. 15, 2021, 39 pages.
U.S. Appl. No. 16/160,968—Office Action dated Jan. 19, 2022, 71 pages.
AU 2018350891—Notice of Acceptance dated Dec. 1, 2021, 3 pages.
BR 1120190274804—Response to First Office Action (in Spanish), dated Sep. 6, 2021, filed Dec. 20, 2021, 9 pages.
CA 3066775—Second Office Action dated Dec. 1, 2021, 3 pages.
NZ 759804—Notice of Acceptance, dated Dec. 16, 2021, 1 page.
RU 2019139312—Notice of Allowance dated Dec. 30, 2021, 29 pages.
Douville et al., Assessing the Pathogenicity of Insertion and Deletion Variants with the Variant Effect Scoring Tool, Human mutation, dated 2016, vol. 37, No. 1, pp. 28-35.
AU 2018352201 Notice of Acceptance dated Nov. 24, 2021, 3 pages.
KR 10-2019-7036422—Notice of Allowance, dated Nov. 9, 2021, 3 pages.

(56) References Cited

OTHER PUBLICATIONS

Lin et al., Computational identification and characterization of primate-specific microRNAs in human genome, Computational Biology and Chemistry, Aug. 24, 2010., vol. 34, Issue. 4, pp. 232-241.
NZ 759813 Notice of Acceptance dated Jan. 17, 2022, 1 page.
KR 10-2021-7032755 Office Action dated Nov. 24, 2021, 5 pages.
MYPI2019007296 Notice of Grant, dated May 20, 2021, 1 page.
NZ 759818 Notice of Acceptance, dated Dec. 2, 2021, 1 page.
NZ 759665 Response to Office Action, filed Jan. 10, 2022, 67 pages.

Residual Block and Skip-Connections used in Convolutional Neural Networks

Batch Normalization Forward Pass with Convolutional Neural Networks $$\mu_B = \frac{1}{n}\sum_{i=1}^{n} x_i^{(\ell-1)}$$

$$\sigma_B^2 = \frac{1}{n}\sum_{i=1}^{n} (x_i^{(\ell-1)} - \mu_B)^2$$

$$\hat{x}^{(\ell-1)} = \frac{x^{(\ell-1)} - \mu_B}{\sqrt{\sigma_B^2 + \epsilon}}$$

$$x^{(\ell)} = \gamma^{(\ell)} \hat{x}^{(\ell-1)} + \beta^{(\ell)}$$

FIG. 9

Batch Normalization – Inference with Convolutional Neural Networks $$\hat{x}^{(\ell-1)} = \frac{x^{(\ell-1)} - \mu_\mathcal{D}}{\sqrt{\sigma_\mathcal{D}^2 + \epsilon}}$$

$$x_i^{(\ell)} = \gamma^{(\ell)} \hat{x}_i^{(\ell-1)} + \beta^{(\ell)}$$

FIG. 10

Batch Normalization Backward Pass with
Convolutional Neural Networks $$\nabla_{\gamma^{(\ell)}} \mathcal{L} = \sum_{i=1}^{n} \left( \nabla_{x^{(\ell+1)}} \mathcal{L} \right)_i \cdot \hat{x}_i^{(\ell)}$$

$$\nabla_{\beta^{(\ell)}} \mathcal{L} = \sum_{i=1}^{n} \left( \nabla_{x^{(\ell+1)}} \mathcal{L} \right)_i$$

FIG. 11

Batch Normalization Before/After Convolution Layers

```
conv_model.add(layers.Conv2D(32, 3, activation='relu'))         <------ After a Conv layer
conv_model.add(layers.BatchNormalization())

dense_model.add(layers.Dense(32, activation='relu'))            <------ After a Dense layer
dense_model.add(layers.BatchNormalization())
```

FIG. 12

Global Average Pooling (GAP) in Convolutional Neural Networks
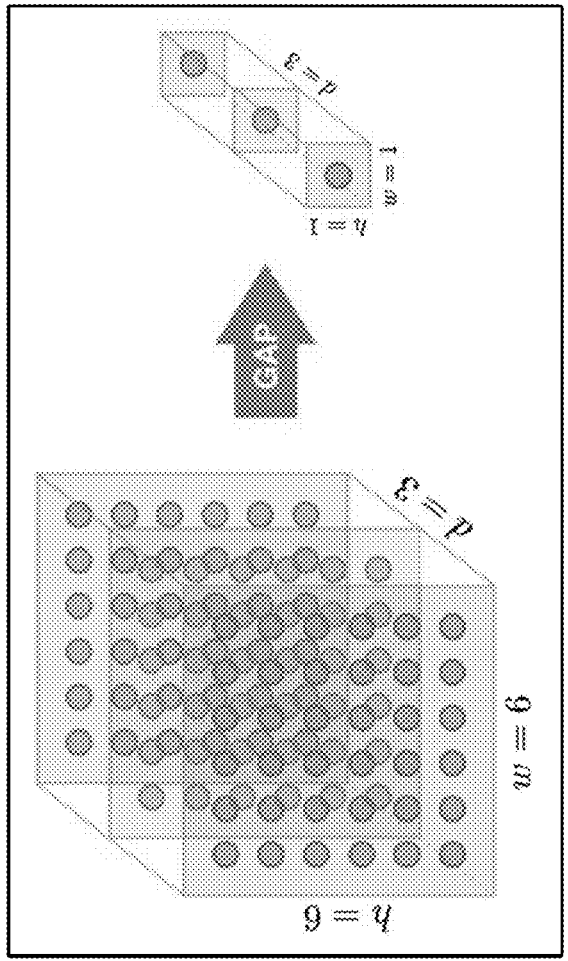
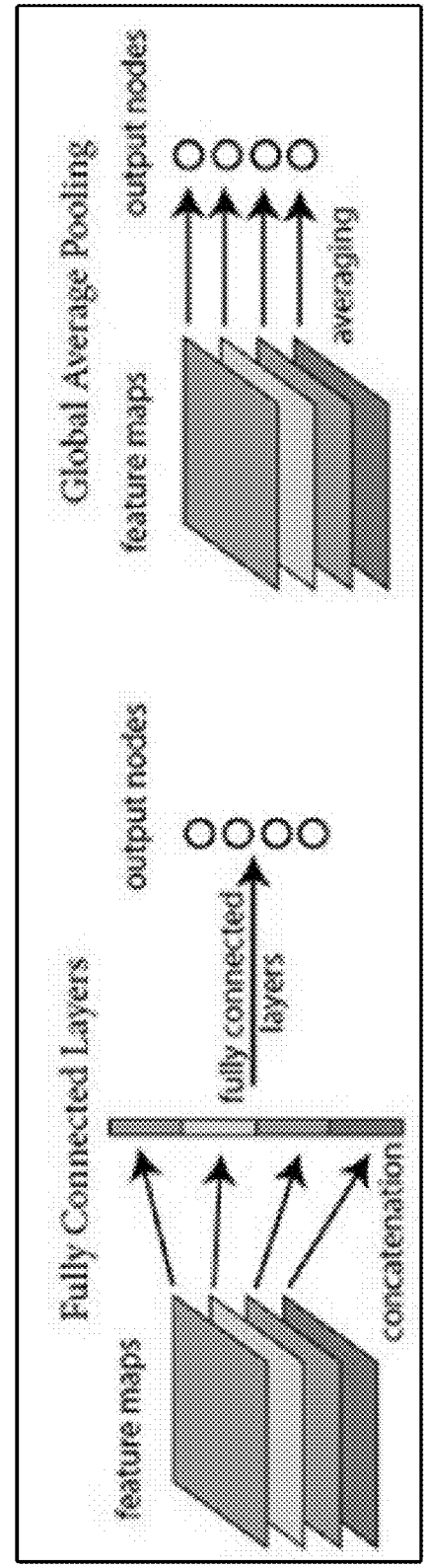
FIG. 14

| Layer | Input to the Layer | Type | Number of Kernel & Window size | Shape | Activation |
|---|---|---|---|---|---|
| Layer 1a | Reference Sequence | Convolution 1D | 40,1 | (51,40) | Linear |
| Layer 1b | Alternative Sequence | Convolution 1D | 40,1 | (51,40) | Linear |
| Layer 1c | Primate Conservation | Convolution 1D | 40,1 | (51,40) | Linear |
| Layer 1d | Mammal Conservation | Convolution 1D | 40,1 | (51,40) | Linear |
| Layer 1e | Vertebrate Conservation | Convolution 1D | 40,1 | (51,40) | Linear |
| Pre-trained Secondary Structure Prediction Model (Trainable Network) | Primate + Mammal + Vertebrate Conservation | - | - | (51,40) | - |
| Pre-trained Solvent Accessibility Model (Trainable Network) | Primate + Mammal + Vertebrate Conservation | | | (51,40) | |
| Layer 1f | Pre-trained Structure Prediction Model output | Convolution 1D | 40,1 | (51,40) | Linear |
| Layer 1g | Pre-trained Solvent Accessibility Model output | Convolution 1D | 40,1 | (51,40) | Linear |
| Merge 1a | Layer 1a, Layer 1c, Layer 1d, Layer 1e, Layer 1f, Layer 1g | Add | - | (51,40) | - |
| Merge 1b | Layer 1b, Layer 1c, Layer 1d, Layer 1e, Layer 1f, Layer 1g | Add | | (51,40) | |
| Layer 2a | Merge 1a | Batch Normalization | - | (51,40) | - |
| Layer 3a | Layer 2a | Activation | | (51,40) | Relu |
| Layer 4a | Layer 3a | Convolution 1D | 40,5 | (51,40) | Linear |
| Layer 5a | Layer 4a | Batch Normalization | | (51,40) | |
| Layer 6a | Layer 5a | Activation | - | (51,40) | Relu |
| Layer 7a | Layer 6a | Convolution 1D | 40,5 | (51,40) | Linear |
| Layer 2b | Merge 1b | Batch Normalization | - | (51,40) | - |
| Layer 3b | Layer 2b | Activation | | (51,40) | Relu |
| Layer 4b | Layer 3b | Convolution 1D | 40,5 | (51,40) | Linear |

FIG. 18A

| Layer 5b | Layer 4b | Batch Normalization | | (51,40) | |
| Layer 6b | Layer 5b | Activation | | (51,40) | Relu |
| Layer 7b | Layer 6b | Convolution 1D | 40,5 | (51,40) | Linear |
| Merge 2x | Layer 7x, Layer 7b | Concatenate | | (51,80) | |
| Merge 2b | Layer 7x, Layer 7b | Concatenate | | (51,80) | |
| Layer 8a | Merge 2a | Convolution 1D | 40,5 | (51,40) | Linear |
| Layer 8b | Merge 2b | Convolution 1D | 40,5 | (51,40) | Linear |
| Layer 9 | Layer 8a | Batch Normalization | | (51,40) | |
| Layer 10 | Layer 9 | Activation | | (51,40) | Relu |
| Layer 11 | Layer 10 | Convolution 1D | 40,5 | (51,40) | Linear |
| Layer 12 | Layer 11 | Batch Normalization | | (51,40) | |
| Layer 13 | Layer 12 | Activation | | (51,40) | Relu |
| Layer 14 | Layer 13 | Convolution 1D | 40,5 | (51,40) | Linear |
| Merge3 | Layer 8a, Layer 14 | Add | | (51,40) | |
| Layer 15 | Merge3 | Batch Normalization | | (51,40) | |
| Layer 16 | Layer 15 | Activation | | (51,40) | Relu |
| Layer 17 | Layer 16 | Convolution 1D | 40,5 | (51,40) | Linear |
| Layer 18 | Layer 17 | Batch Normalization | | (51,40) | |
| Layer 19 | Layer 18 | Activation | | (51,40) | Relu |
| Layer 20 | Layer 19 | Convolution 1D | 40,5 | (51,40) | Linear |
| Merge4 | Merge3, Layer20 | Add | | (51,40) | |
| Layer 21 | Merge4 | Convolution 1D | 40,5 | (51,40) | Linear |
| Layer 22 | Merge4 | Batch Normalization | | (51,40) | |
| Layer 23 | Layer 22 | Activation | | (51,40) | Relu |
| Layer 24 | Layer 23 | Convolution 1D | 40,5 | (51,40) | Linear |
| Layer 25 | Layer 24 | Batch Normalization | | (51,40) | |
| Layer 26 | Layer 25 | Activation | | (51,40) | Relu |
| Layer 27 | Layer 26 | Convolution 1D | 40,5 | (51,40) | Linear |
| Merge5 | Merge4, Layer 27 | Add | | (51,40) | |
| Layer 28 | Merge 5 | Batch Normalization | | (51,40) | |
| Layer 29 | Layer 28 | Activation | | (51,40) | Relu |
| Layer 30 | Layer 29 | Convolution 1D | 40,5 | (51,40) | Linear |
| Layer 31 | Layer 30 | Batch Normalization | | (51,40) | |
| Layer 32 | Layer 31 | Activation | | (51,40) | Relu |

FIG. 18B

| Layer 33 | Layer 32 | Convolution 1D | 40, 5 | (51, 40) | Linear |
| Merge 6 | Merge 5, Layer 33 | Add | - | (51, 40) | - |
| Layer 34 | Merge 6 | Convolution 1D | 40, 1 | (51, 40) | Linear |
| Layer 35 | Merge 6 | Batch Normalization | - | (51, 40) | - |
| Layer 36 | Layer 35 | Activation | - | (51, 40) | Relu |
| Layer 37 | Layer 36 | Convolution 1D | 40, 5 | (51, 40) | Linear |
| Layer 38 | Layer 37 | Batch Normalization | - | (51, 40) | - |
| Layer 39 | Layer 38 | Activation | - | (51, 40) | Relu |
| Layer 40 | Layer 39 | Convolution 1D | 40, 3 | (51, 40) | Linear |
| Merge 7 | Merge 6, Layer 40 | Add | - | (51, 40) | - |
| Layer 41 | Merge 7 | Batch Normalization | - | (51, 40) | - |
| Layer 42 | Layer 41 | Activation | - | (51, 40) | Relu |
| Layer 43 | Layer 42 | Convolution 1D | 40, 5 | (51, 40) | Linear |
| Layer 44 | Layer 43 | Batch Normalization | - | (51, 40) | - |
| Layer 45 | Layer 44 | Activation | - | (51, 40) | Relu |
| Layer 46 | Layer 45 | Convolution 1D | 40, 5 | (51, 40) | Linear |
| Merge 8 | Merge 7, Layer 46 | Add | - | (51, 40) | - |
| Layer 47 | Merge 8 | Convolution 1D | 40, 1 | (51, 40) | Linear |
| Merge 9 | Layer 8b, Layer 21, Layer 34, Layer 47 | Add | - | (51, 40) | - |
| Layer 48 | Merge 9 | Batch Normalization | - | (51, 40) | - |
| Layer 49 | Layer 48 | Activation | - | (51, 40) | Relu |
| Layer 50 | Layer 49 | Convolution 1D | 40, 1 | (51, 40) | Linear |
| Layer 51 | Layer 50 | Batch Normalization | - | (51, 40) | - |
| Layer 52 | Layer 51 | Activation | - | (51, 40) | Relu |
| Layer 53 | Layer 52 | Convolution 1D | 40, 3 | (51, 40) | Linear |
| Merge 10 | Merge 9, Layer 53 | Add | - | (51, 40) | - |
| Layer 54 | Merge 10 | Convolution 1D | 1, 1 | (51, 1) | Sigmoid |
| Output Layer | Layer 54 | GlobalMaxPooling 1D | - | 1 | - |

FIG. 18C

| Layer | Input to the Layer | Type | Number of Kernel & Kernel Window size | Shape | Activation |
|---|---|---|---|---|---|
| Layer 1a | Input PSFM | Convolution 1D | 40,1 | (51,40) | Linear |
| Layer 2a | Layer 1a | Convolution 1D | 40,1 | (51,40) | Linear |
| Layer 1b | Input PSFM | Convolution 1D | 40,1 | (51,40) | Linear |
| Layer 2b | Layer 1b | Convolution 1D | 40,1 | (51,40) | Linear |
| Layer 3 | Layer 2a | Batch Normalization | - | (51,40) | - |
| Layer 4 | Layer 3 | Activation | - | (51,40) | Relu |
| Layer 5 | Layer 4 | Convolution 1D | 40,5 | (51,40) | Linear |
| Layer 6 | Layer 5 | Batch Normalization | - | (51,40) | - |
| Layer 8 | Layer 7 | Activation | - | (51,40) | Relu |
| Layer 9 | Layer 8 | Convolution 1D | 40,5 | (51,40) | Linear |
| Merge1 | Layer 2a, Layer 9 | Add | - | (51,40) | - |
| Layer 10 | Merge1 | Batch Normalization | - | (51,40) | - |
| Layer 11 | Layer 10 | Activation | - | (51,40) | Relu |
| Layer 12 | Layer 11 | Convolution 1D | 40,5 | (51,40) | Linear |
| Layer 13 | Layer 12 | Batch Normalization | - | (51,40) | - |
| Layer 14 | Layer 13 | Activation | - | (51,40) | Relu |
| Layer 15 | Layer 14 | Convolution 1D | 40,5 | (51,40) | Linear |
| Merge2 | Merge1, Layer15 | Add | - | (51,40) | - |
| Layer 16 | Merge2 | Convolution 1D | 40,1 | (51,40) | Linear |
| Layer 17 | Merge2 | Batch Normalization | - | (51,40) | - |
| Layer 18 | Layer 17 | Activation | - | (51,40) | Relu |
| Layer 19 | Layer 18 | Convolution 1D | 40,5 | (51,40) | Linear |
| Layer 20 | Layer 19 | Batch Normalization | - | (51,40) | - |
| Layer 21 | Layer 20 | Activation | - | (51,40) | Relu |
| Layer 22 | Layer 21 | Convolution 1D | 40,5 | (51,40) | Linear |
| Merge3 | Merge2, Layer 22 | Add | - | (51,40) | - |

FIG. 21A

| Layer 23 | Merge 3 | Batch Normalization | - | (51,40) | - |
| Layer 24 | Layer 23 | Activation | - | (51,40) | Relu |
| Layer 25 | Layer 24 | Convolution 1D | 40,5 | (51,40) | Linear |
| Layer 26 | Layer 25 | Batch Normalization | - | (51,40) | - |
| Layer 27 | Layer 26 | Activation | - | (51,40) | Relu |
| Layer 28 | Layer 27 | Convolution 1D | 40,5 | (51,40) | Linear |
| Merge4 | Merge3, Layer 28 | Add | - | (51,40) | - |
| Layer 29 | Merge4 | Convolution 1D | 40,1 | (51,40) | Linear |
| Layer 30 | Merge4 | Batch Normalization | - | (51,40) | - |
| Layer 31 | Layer 30 | Activation | - | (51,40) | Relu |
| Layer 32 | Layer 31 | Convolution 1D | 40,5 | (51,40) | Linear |
| Layer 33 | Layer 32 | Batch Normalization | - | (51,40) | - |
| Layer 34 | Layer 33 | Activation | - | (51,40) | Relu |
| Layer 35 | Layer 34 | Convolution 1D | 40,5 | (51,40) | Linear |
| Merge5 | Merge4, Layer 35 | Add | - | (51,40) | - |
| Layer 36 | merge5 | Batch Normalization | - | (51,40) | - |
| Layer 37 | Layer 36 | Activation | - | (51,40) | Relu |
| Layer 38 | Layer 37 | Convolution 1D | 40,5 | (51,40) | Linear |
| Layer 39 | Layer 38 | Batch Normalization | - | (51,40) | - |
| Layer 40 | Layer 39 | Activation | - | (51,40) | Relu |
| Layer 41 | Layer 40 | Convolution 1D | 40,5 | (51,40) | Linear |
| Merge6 | Merge5, Layer 41 | Add | - | (51,40) | - |
| Layer 42 | Merge 6 | Convolution 1D | 40,1 | (51,40) | Linear |
| Merge7 | Layer 28, Layer 16, Layer 35, Layer 42 | Add | - | (51,40) | - |
| Layer 43 | Merge 7 | Batch Normalization | - | (51,40) | - |
| Layer 44 | Layer 43 | Activation | - | (51,40) | Relu |
| Layer 45 | Merge 44 | Convolution 1D | 40,1 | (51,40) | Linear |
| Layer 46 | Layer 45 | Batch Normalization | - | (51,40) | - |
| Layer 47 | Layer 46 | Activation | - | (51,40) | Relu |
| Layer 48 | Layer 47 | Convolution 1D | 40,1 | (51,40) | Linear |
| Merge 8 | Merge 7, Layer 48 | Add | - | (51,40) | - |
| Output layer | Merge 8 | Convolution 1D | 3,1 | (51,3) | Softmax |

FIG. 21B

| Layer | Input to the Layer | Type | Number of Kernel & Kernel Window size | Shape | Activation |
|---|---|---|---|---|---|
| Layer 1a | Input PSFM | Convolution 1D | 40,1 | (51,40) | Linear |
| Layer 2a | Layer 1a | Convolution 1D | 40,1 | (51,40) | Linear |
| Layer 1b | Input PSFM | Convolution 1D | 40,1 | (51,40) | Linear |
| Layer 2b | Layer 1b | Convolution 1D | 40,1 | (51,40) | Linear |
| Layer 3 | Layer 2a | Batch Normalization | - | (51,40) | - |
| Layer 4 | Layer 3 | Activation | - | (51,40) | Relu |
| Layer 5 | Layer 4 | Convolution 1D | 40,5 | (51,40) | Linear |
| Layer 6 | Layer 5 | Batch Normalization | - | (51,40) | - |
| Layer 7 | Layer 6 | Activation | - | (51,40) | Relu |
| Layer 9 | Layer 8 | Convolution 1D | 40,5 | (51,40) | Linear |
| Merge1 | Layer 2a, Layer 9 | Add | - | (51,40) | - |
| Layer 10 | Merge1 | Batch Normalization | - | (51,40) | - |
| Layer 11 | Layer 10 | Activation | - | (51,40) | Relu |
| Layer 12 | Layer 11 | Convolution 1D | 40,5 | (51,40) | Linear |
| Layer 13 | Layer 12 | Batch Normalization | - | (51,40) | - |
| Layer 14 | Layer 13 | Activation | - | (51,40) | Relu |
| Layer 15 | Layer 14 | Convolution 1D | 40,5 | (51,40) | Linear |
| Merge2 | Merge1, Layer15 | Add | - | (51,40) | - |
| Layer 16 | Merge2 | Convolution 1D | 40,1 | (51,40) | Linear |
| Layer 17 | Merge2 | Batch Normalization | - | (51,40) | - |
| Layer 18 | Layer 17 | Activation | - | (51,40) | Relu |
| Layer 19 | Layer 18 | Convolution 1D | 40,5 | (51,40) | Linear |
| Layer 20 | Layer 19 | Batch Normalization | - | (51,40) | - |
| Layer 21 | Layer 20 | Activation | - | (51,40) | Relu |
| Layer 22 | Layer 21 | Convolution 1D | 40,5 | (51,40) | Linear |
| Merge3 | Merge2, Layer 22 | Add | - | (51,40) | - |

FIG. 22A

| | | | | | |
|---|---|---|---|---|---|
| Layer 23 | Merge 3 | Batch Normalization | - | (51,40) | - |
| Layer 24 | Layer 23 | Activation | - | (51,40) | Relu |
| Layer 25 | Layer 24 | Convolution 1D | 40,5 | (51,40) | Linear |
| Layer 26 | Layer 25 | Batch Normalization | - | (51,40) | - |
| Layer 27 | Layer 26 | Activation | - | (51,40) | Relu |
| Layer 28 | Layer 27 | Convolution 1D | 40,5 | (51,40) | Linear |
| Merge4 | Merge3, Layer 28 | Add | - | (51,40) | - |
| Layer 29 | Merge4 | Convolution 1D | 40,1 | (51,40) | Linear |
| Layer 30 | Merge4 | Batch Normalization | - | (51,40) | - |
| Layer 31 | Layer 30 | Activation | - | (51,40) | Relu |
| Layer 32 | Layer 31 | Convolution 1D | 40,5 | (51,40) | Linear |
| Layer 33 | Layer 32 | Batch Normalization | - | (51,40) | - |
| Layer 34 | Layer 33 | Activation | - | (51,40) | Relu |
| Layer 35 | Layer 34 | Convolution 1D | 40,5 | (51,40) | Linear |
| Merge5 | Merge4, Layer 35 | Add | - | (51,40) | - |
| Layer 36 | merge5 | Batch Normalization | - | (51,40) | - |
| Layer 37 | Layer 36 | Activation | - | (51,40) | Relu |
| Layer 38 | Layer 37 | Convolution 1D | 40,5 | (51,40) | Linear |
| Layer 39 | Layer 38 | Batch Normalization | - | (51,40) | - |
| Layer 40 | Layer 39 | Activation | - | (51,40) | Relu |
| Layer 41 | Layer 40 | Convolution 1D | 40,5 | (51,40) | Linear |
| Merge6 | Merge5, Layer 41 | Add | - | (51,40) | - |
| Layer 42 | Merge 6 | Convolution 1D | 40,1 | (51,40) | Linear |
| Merge7 | Layer 26, Layer 18, Layer 29, Layer 42 | Add | - | (51,40) | - |
| Layer 43 | Merge 7 | Batch Normalization | - | (51,40) | - |
| Layer 44 | Layer 43 | Activation | - | (51,40) | Relu |
| Layer 45 | Merge 44 | Convolution 1D | 40,1 | (51,40) | Linear |
| Layer 46 | Layer 45 | Batch Normalization | - | (51,40) | - |
| Layer 47 | Layer 46 | Activation | - | (51,40) | Relu |
| Layer 48 | Layer 47 | Convolution 1D | 40,1 | (51,40) | Linear |
| Merge 8 | Merge 7, Layer 48 | Add | - | (51,40) | - |
| Output layer | Merge 8 | Convolution 1D | 3,1 | (51,3) | Softmax |

FIG. 22B

|  | Training Accuracy | Validation Accuracy | Testing Accuracy |
|---|---|---|---|
| 3-State Secondary Structure | 80.32 % | 79.17 % | 79.86 % |
| 3-State Solvent Accessibility | 64.83 % | 60.53 % | 60.31 % |

FIG. 39

| Models | Replicates | Withheld Primate Variant Accuracy | DDD Case vs Control -log(pvalue) | DDD 605 disease genes -log(pvalue) |
|---|---|---|---|---|
| Use DL predicted secondary structure labels | 1 | 0.914 | 28.60 | 15.61 |
| | 2 | 0.919 | 32.32 | 15.94 |
| | 3 | 0.915 | 29.48 | 16.38 |
| | 4 | 0.917 | 30.35 | 15.62 |
| | 5 | 0.916 | 29.11 | 16.22 |
| | Median | 0.916 | 29.48 | 15.94 |
| Replace DL predicted secondary structure labels with DSSP secondary structure labels of human proteins when available | 1 | 0.916 | 29.48 | 15.94 |
| | 2 | 0.913 | 31.72 | 16.24 |
| | 3 | 0.915 | 31.09 | 15.69 |
| | 4 | 0.915 | 30.49 | 16.09 |
| | 5 | 0.915 | 30.57 | 14.79 |
| | Median | 0.915 | 30.79 | 16.09 |

FIG. 40

|  | Withheld Primate Variant Accuracy | DDD Case vs Control -log(pvalue) |
|---|---|---|
| SIFT | 0.7490 | 14.1233 |
| PolyPhen-2 | 0.7618 | 13.7044 |
| CADD | 0.7939 | 14.8167 |
| M-CAP | 0.7667 | 20.6078 |
| LRT | 0.7598 | 6.2960 |
| MutationTaster | 0.5332 | 2.2811 |
| MutationAssessor | 0.6879 | 11.5202 |
| FATHMM | 0.5981 | 8.1690 |
| PROVEAN | 0.6995 | 14.0747 |
| VEST3 | 0.7978 | 19.7068 |
| MetaSVM | 0.7215 | 15.9829 |
| MetaLR | 0.6991 | 15.5842 |
| REVEL | 0.7686 | 21.5892 |
| MutPred | 0.6240 | 7.3044 |
| DANN | 0.7666 | 9.8976 |
| MKL_coding | 0.7657 | 6.2469 |
| Eigen | 0.8003 | 13.5364 |
| GenoCanyon | 0.8058 | 7.2196 |
| integrated_fitCons | 0.5331 | 0.4954 |
| GERP | 0.7430 | 2.8285 |
| PrimateAI Human | 0.8411 | 23.4536 |
| PrimateAI Human + Primates | 0.9156 | 28.8346 |

FIG. 41

| | -log(pvalue) | AUC | Threshold | Classification Accuracy |
|---|---|---|---|---|
| SIFT | 5.6793 | 0.6903 | 0.001 | 0.7949 |
| PolyPhen-2 | 8.5522 | 0.7430 | 0.956 | 0.8197 |
| CADD | 6.4772 | 0.7087 | 5.040 | 0.7643 |
| M-CAP | 7.7143 | 0.7283 | 0.081 | 0.7348 |
| LRT | 6.0285 | 0.6970 | 1.00E-06 | 0.7604 |
| MutationTaster | 2.1366 | 0.6117 | 1.000 | 0.6564 |
| MutationAssessor | 6.6779 | 0.7115 | 2.240 | 0.7006 |
| FATHMM | 2.5979 | 0.6194 | -1.260 | 0.6401 |
| PROVEAN | 7.3447 | 0.7188 | -4.310 | 0.7833 |
| VEST3 | 7.0357 | 0.7173 | 0.679 | 0.7953 |
| MetaSVM | 6.2556 | 0.7041 | -0.3371 | 0.7406 |
| MetaLR | 5.8707 | 0.6971 | 0.349 | 0.7407 |
| REVEL | 8.4115 | 0.7392 | 0.456 | 0.8056 |
| MutPred | 5.3370 | 0.7036 | 0.526 | 0.6949 |
| DANN | 3.1588 | 0.6397 | 0.996 | 0.7046 |
| MKL_coding | 1.1649 | 0.5773 | 0.965 | 0.5840 |
| Eigen | 7.1659 | 0.7320 | 0.577 | 0.7844 |
| GenoCanyon | 4.6763 | 0.6740 | 0.999 | 0.6875 |
| integrated_fitCons | 0.8315 | 0.5554 | 0.706 | 0.5736 |
| GERP | 1.0330 | 0.5718 | 5.060 | 0.6330 |
| PrimateAI Human + Primates | 15.3064 | 0.8154 | 0.802 | 0.8772 |

FIG. 42

Human Orthologous Missense SNP: A missense SNP in a non-human species that has matching reference and alternative codons with humans.

FIG. 53 Classify Chimpanzee Missense SNPs with Matching Reference Codons with Humans as Benign

|  | Rare | Common |
|---|---|---|
| Synonymous SNPs | x | y |
| Missense Identical SNPs | m | n |

2 x 2 Contingency Table $$\text{ES for Synonymous SNPs} = \frac{\text{Count of Rare Synonymous SNPs (x)}}{\text{Count of Common Synonymous SNPs (y)}}$$

$$\text{ES for Missense Identical SNPs} = \frac{\text{Count of Rare Missense Identical SNPs (m)}}{\text{Count of Common Missense Identical SNPs (n)}}$$

FIG. 54

RECURRENT NEURAL NETWORK-BASED VARIANT PATHOGENICITY CLASSIFIER

PRIORITY APPLICATIONS

This application is a continuation of U.S. patent application Ser. No. 16/413,476, by Hong Gao, Kai-How Farh, Laksshman Sundaram and Jeremy Francis McRae, entitled "Deep Learning-Based Techniques for Training Deep Convolutional Neural Networks," filed May 15, 2019, which is a continuation of U.S. patent application Ser. No. 16/160,903, by Hong Gao, Kai-How Farh, Laksshman Sundaram and Jeremy Francis McRae, entitled "Deep Learning-Based Techniques for Training Deep Convolutional Neural Networks," filed Oct. 15, 2018, which claims priority to or the benefit of U.S. Provisional Patent Application No. 62/573,144, titled, "Training a Deep Pathogenicity Classifier Using Large-Scale Benign Training Data," by Hong Gao, Kai-How Farh, Laksshman Sundaram and Jeremy Francis McRae, filed Oct. 16, 2017; U.S. Provisional Patent Application No. 62/573,149, titled, "Pathogenicity Classifier Based On Deep Convolutional Neural Networks," by Kai-How Farh, Laksshman Sundaram, Samskruthi Reddy Padigepati and Jeremy Francis McRae, filed Oct. 16, 2017; U.S. Provisional Patent Application No. 62/573,153, titled, "Deep Semi-Supervised Learning that Generates Large-Scale Pathogenic Training Data," by Hong Gao, Kai-How Farh, Laksshman Sundaram and Jeremy Francis McRae, filed Oct. 16, 2017; 1000-3/IP-1613-PRV); and U.S. Provisional Patent Application No. 62/582,898, titled, "Pathogenicity Classification of Genomic Data Using Deep Convolutional Neural Networks (CNNs)," by Hong Gao, Kai-How Farh and Laksshman Sundaram, filed Nov. 7, 2017. The provisional applications are hereby incorporated by reference for all purposes.

INCORPORATIONS

The following are incorporated by reference for all purposes as if fully set forth herein:

PCT Patent Application No. PCT/US18/55840, titled "DEEP LEARNING-BASED TECHNIQUES FOR TRAINING DEEP CONVOLUTIONAL NEURAL NETWORKS," by Hong Gao, Kai-How Farh, Laksshman Sundaram and Jeremy Francis McRae, filed on Oct. 15, 2018, subsequently published as PCT Publication No. WO 2019/079166.

PCT Patent Application No. PCT/US18/55878, titled "DEEP CONVOLUTIONAL NEURAL NETWORKS FOR VARIANT CLASSIFICATION," by Laksshman Sundaram, Kai-How Farh, Hong Gao, Samskruthi Reddy Padigepati and Jeremy Francis McRae, filed on Oct. 15, 2018, subsequently published as PCT Publication No. WO 2019/079180.

PCT Patent Application No. PCT/US18/55881, titled "SEMI-SUPERVISED LEARNING FOR TRAINING AN ENSEMBLE OF DEEP CONVOLUTIONAL NEURAL NETWORKS," by Laksshman Sundaram, Kai-How Farh, Hong Gao and Jeremy Francis McRae, filed on Oct. 15, 2018, subsequently published as PCT Publication No. WO 2019/079182.

US Nonprovisional patent application No. 16/160,903, titled "DEEP LEARNING-BASED TECHNIQUES FOR TRAINING DEEP CONVOLUTIONAL NEURAL NETWORKS," by Hong Gao, Kai-How Farh, Laksshman Sundaram and Jeremy Francis McRae, filed filed on Oct. 15, 2018.

US Nonprovisional patent application No. 16/160,986, titled "DEEP CONVOLUTIONAL NEURAL NETWORKS FOR VARIANT CLASSIFICATION," by Laksshman Sundaram, Kai-How Farh, Hong Gao and Jeremy Francis McRae, filed on Oct. 15, 2018.

US Nonprovisional patent application No. 16/160,986, titled "SEMI-SUPERVISED LEARNING FOR TRAINING AN ENSEMBLE OF DEEP CONVOLUTIONAL NEURAL NETWORKS," by Laksshman Sundaram, Kai-How Farh, Hong Gao and Jeremy Francis McRae, filed on Oct. 15, 2018.

Document 1—S. Dieleman, H. Zen, K. Simonyan, O. Vinyals, A. Graves, N. Kalchbrenner, A. Senior, and K. Kavukcuoglu, "WAVENET: A GENERATIVE MODEL FOR RAW AUDIO," arXiv:1609.03499, 2016;

Document 2—S. Ö. Arik, M. Chrzanowski, A. Coates, G. Diamos, A. Gibiansky, Y. Kang, X. Li, J. Miller, A. Ng, J. Raiman, S. Sengupta and M. Shoeybi, "DEEP VOICE: REAL-TIME NEURAL TEXT-TO-SPEECH," arXiv: 1702.07825, 2017;

Document 3—F. Yu and V. Koltun, "MULTI-SCALE CONTEXT AGGREGATION BY DILATED CONVOLUTIONS," arXiv:1511.07122, 2016;

Document 4—K. He, X. Zhang, S. Ren, and J. Sun, "DEEP RESIDUAL LEARNING FOR IMAGE RECOGNITION," arXiv:1512.03385, 2015;

Document 5—R. K. Srivastava, K. Greff, and J. Schmidhuber, "HIGHWAY NETWORKS," arXiv: 1505.00387, 2015;

Document 6—G. Huang, Z. Liu, L. van der Maaten and K. Q. Weinberger, "DENSELY CONNECTED CONVOLUTIONAL NETWORKS," arXiv:1608.06993, 2017;

Document 7—C. Szegedy, W. Liu, Y. Jia, P. Sermanet, S. Reed, D. Anguelov, D. Erhan, V. Vanhoucke, and A. Rabinovich, "GOING DEEPER WITH CONVOLUTIONS," arXiv: 1409.4842, 2014;

Document 8—S. Ioffe and C. Szegedy, "BATCH NORMALIZATION: ACCELERATING DEEP NETWORK TRAINING BY REDUCING INTERNAL COVARIATE SHIFT," arXiv: 1502.03167, 2015;

Document 9—J. M. Wolterink, T. Leiner, M. A. Viergever, and I. Išgum, "DILATED CONVOLUTIONAL NEURAL NETWORKS FOR CARDIOVASCULAR MR SEGMENTATION IN CONGENITAL HEART DISEASE," arXiv:1704.03669, 2017;

Document 10—L. C. Piqueras, "AUTOREGRESSIVE MODEL BASED ON A DEEP CONVOLUTIONAL NEURAL NETWORK FOR AUDIO GENERATION," Tampere University of Technology, 2016;

Document 11—J. Wu, "Introduction to Convolutional Neural Networks," Nanjing University, 2017;

Document 12—I. J. Goodfellow, D. Warde-Farley, M. Mirza, A. Courville, and Y. Bengio, "CONVOLUTIONAL NETWORKS", Deep Learning, MIT Press, 2016; and Document 13—J. Gu, Z. Wang, J. Kuen, L. Ma, A. Shahroudy, B. Shuai, T. Liu, X. Wang, and G. Wang, "RECENT ADVANCES IN CONVOLUTIONAL NEURAL NETWORKS," arXiv:1512.07108, 2017.

Document 1 describes deep convolutional neural network architectures that use groups of residual blocks with convolution filters having same convolution window size, batch normalization layers, rectified linear unit (abbreviated ReLU) layers, dimensionality altering layers, atrous convolution layers with exponentially growing atrous convolution rates, skip connections, and a softmax classification layer to accept an input sequence and produce an output sequence that scores entries in the input sequence. The technology disclosed uses neural network components and parameters described in Document 1. In one implementation, the technology disclosed modifies the parameters of the neural network components described in Document 1. For instance, unlike in Document 1, the atrous convolution rate in the technology disclosed progresses non-exponentially from a lower residual block group to a higher residual block group. In another example, unlike in Document 1, the convolution window size in the technology disclosed varies between groups of residual blocks.

Document 2 describes details of the deep convolutional neural network architectures described in Document 1.

Document 3 describes atrous convolutions used by the technology disclosed. As used herein, atrous convolutions are also referred to as "dilated convolutions". Atrous/dilated convolutions allow for large receptive fields with few trainable parameters. An atrous/dilated convolution is a convolution where the kernel is applied over an area larger than its length by skipping input values with a certain step, also called atrous convolution rate or dilation factor. Atrous/dilated convolutions add spacing between the elements of a convolution filter/kernel so that neighboring input entries (e.g., nucleotides, amino acids) at larger intervals are considered when a convolution operation is performed. This enables incorporation of long-range contextual dependencies in the input. The atrous convolutions conserve partial convolution calculations for reuse as adjacent nucleotides are processed.

Document 4 describes residual blocks and residual connections used by the technology disclosed.

Document 5 describes skip connections used by the technology disclosed. As used herein, skip connections are also referred to as "highway networks".

Document 6 describes densely connected convolutional network architectures used by the technology disclosed.

Document 7 describes dimensionality altering convolution layers and modules-based processing pipelines used by the technology disclosed. One example of a dimensionality altering convolution is a 1×1 convolution.

Document 8 describes batch normalization layers used by the technology disclosed.

Document 9 also describes atrous/dilated convolutions used by the technology disclosed.

Document 10 describes various architectures of deep neural networks that can be used by the technology disclosed, including convolutional neural networks, deep convolutional neural networks, and deep convolutional neural networks with atrous/dilated convolutions.

Document 11 describes details of a convolutional neural network that can be used by the technology disclosed, including algorithms for training a convolutional neural network with subsampling layers (e.g., pooling) and fully-connected layers.

Document 12 describes details of various convolution operations that can be used by the technology disclosed.

Document 13 describes various architectures of convolutional neural networks that can be used by the technology disclosed.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep learning-based techniques for training deep convolutional neural networks.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Neural Networks

FIG. 1 shows one implementation of a fully connected neural network with multiple layers. A neural network is a system of interconnected artificial neurons (e.g., $a_1$, $a_2$, $a_3$) that exchange messages between each other. The illustrated neural network has three inputs, two neurons in the hidden layer and two neurons in the output layer. The hidden layer has an activation function $f(\cdot)$ and the output layer has an activation function $g(\cdot)$. The connections have numeric weights (e.g., $w_{11}$, $w_{21}$, $w_{12}$, $w_{31}$, $w_{22}$, $w_{32}$, $v_{11}$, $v_{22}$) that are tuned during the training process, so that a properly trained network responds correctly when fed an image to recognize. The input layer processes the raw input, the hidden layer processes the output from the input layer based on the weights of the connections between the input layer and the hidden layer. The output layer takes the output from the hidden layer and processes it based on the weights of the connections between the hidden layer and the output layer. The network includes multiple layers of feature-detecting neurons. Each layer has many neurons that respond to different combinations of inputs from the previous layers. These layers are constructed so that the first layer detects a set of primitive patterns in the input image data, the second layer detects patterns of patterns and the third layer detects patterns of those patterns.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The color drawings also may be available in PAIR via the Supplemental Content tab. In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIG. 9 shows the batch normalization forward pass.

FIG. 10 illustrates the batch normalization transform at test time.

FIG. 11 shows the batch normalization backward pass.

FIG. 12 depicts use of a batch normalization layer after and before a convolutional or densely connected layer.

FIG. 14 illustrates how global average pooling (GAP) works.

FIGS. 18A, 18B, and 18C are Supplementary Table 16 that show example model architecture details of the pathogenicity prediction deep learning model PrimateAI.

FIGS. 21A and 21B are Supplementary Table 11 that show example model architecture details for the 3-state secondary structure prediction deep learning (DL) model.

FIGS. 22A and 22B are Supplementary Table 12 that show example model architecture details for the 3-state solvent accessibility prediction deep learning model.

FIG. 39 is Supplementary Table 14 that shows performance of the 3-state secondary structure and 3-state solvent accessibility prediction models on annotated samples from the Protein DataBank.

FIG. 40 is Supplementary Table 15 that shows performance comparison of deep learning network using annotated secondary structure labels of human proteins from DSSP database.

FIG. 41 is Supplementary Table 17 that shows the accuracy values on the 10,000 withheld primate variants and the p-values for de novo variants in DDD cases vs controls for each of the 20 classifiers we evaluated.

FIG. 42 is Supplementary Table 19 that shows comparison of the performance of different classifiers on de novo variants in the DDD case vs control dataset, restricted to 605 disease-associated genes.

FIG. 54 depicts one implementation of calculating enrichment scores and comparing them.

DETAILED DESCRIPTION

Figure 1:
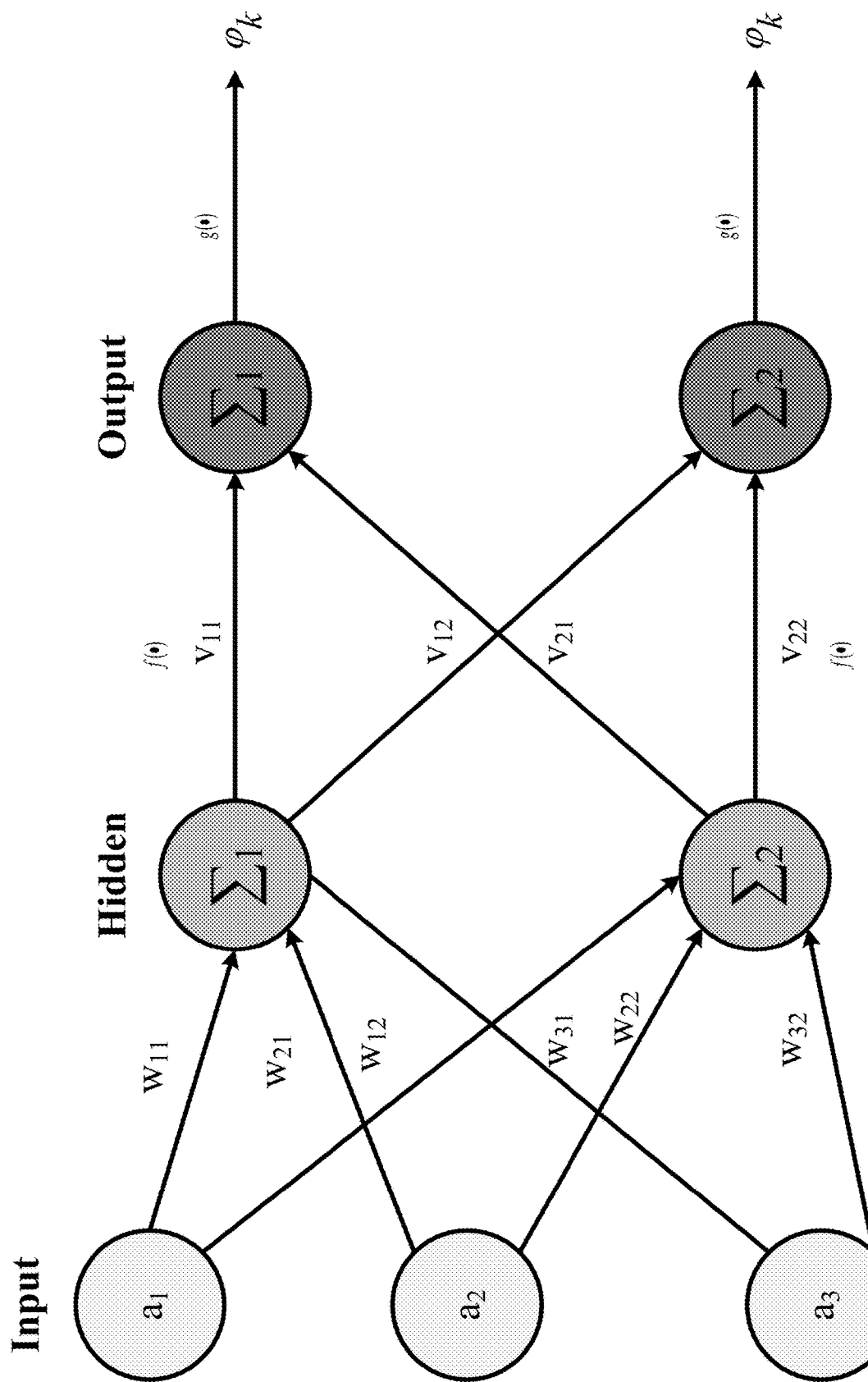
FIG. 1 shows one implementation of a feed-forward neural network with multiple layers.

The following discussion is presented to enable any person skilled in the art to make and use the technology disclosed, and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein.

INTRODUCTION

Convolutional Neural Networks

A convolutional neural network is a special type of neural network. The fundamental difference between a densely connected layer and a convolution layer is this: Dense layers learn global patterns in their input feature space, whereas convolution layers learn local patters: in the case of images, patterns found in small 2D windows of the inputs. This key characteristic gives convolutional neural networks two interesting properties: (1) the patterns they learn are translation invariant and (2) they can learn spatial hierarchies of patterns.

Regarding the first, after learning a certain pattern in the lower-right corner of a picture, a convolution layer can recognize it anywhere: for example, in the upper-left corner. A densely connected network would have to learn the pattern anew if it appeared at a new location. This makes convolutional neural networks data efficient because they need fewer training samples to learn representations they have generalization power.

Regarding the second, a first convolution layer can learn small local patterns such as edges, a second convolution layer will learn larger patterns made of the features of the first layers, and so on. This allows convolutional neural networks to efficiently learn increasingly complex and abstract visual concepts.

A convolutional neural network learns highly non-linear mappings by interconnecting layers of artificial neurons arranged in many different layers with activation functions that make the layers dependent. It includes one or more convolutional layers, interspersed with one or more sub-sampling layers and non-linear layers, which are typically followed by one or more fully connected layers. Each element of the convolutional neural network receives inputs from a set of features in the previous layer. The convolutional neural network learns concurrently because the neurons in the same feature map have identical weights. These local shared weights reduce the complexity of the network such that when multi-dimensional input data enters the network, the convolutional neural network avoids the complexity of data reconstruction in feature extraction and regression or classification process.

Convolutions operate over 3D tensors, called feature maps, with two spatial axes (height and width) as well as a depth axis (also called the channels axis). For an RGB image, the dimension of the depth axis is 3, because the image has three color channels; red, green, and blue. For a black-and-white picture, the depth is 1 (levels of gray). The convolution operation extracts patches from its input feature map and applies the same transformation to all of these patches, producing an output feature map. This output feature map is still a 3D tensor: it has a width and a height. Its depth can be arbitrary, because the output depth is a parameter of the layer, and the different channels in that depth axis no longer stand for specific colors as in RGB input; rather, they stand for filters. Filters encode specific aspects of the input data: at a height level, a single filter could encode the concept "presence of a face in the input," for instance.

For example, the first convolution layer takes a feature map of size (28, 28, 1) and outputs a feature map of size (26, 26, 32): it computes 32 filters over its input. Each of these 32 output channels contains a 26×26 grid of values, which is a response map of the filter over the input, indicating the response of that filter pattern at different locations in the input. That is what the term feature map means: every dimension in the depth axis is a feature (or filter), and the 2D tensor output [:, :, n] is the 2D spatial map of the response of this filter over the input.

Convolutions are defined by two key parameters: (1) size of the patches extracted from the inputs—these are typically 1×1, 3×3 or 5×5 and (2) depth of the output feature map—the number of filters computed by the convolution. Often these start with a depth of 32, continue to a depth of 64, and terminate with a depth of 128 or 256.

Figure 2:
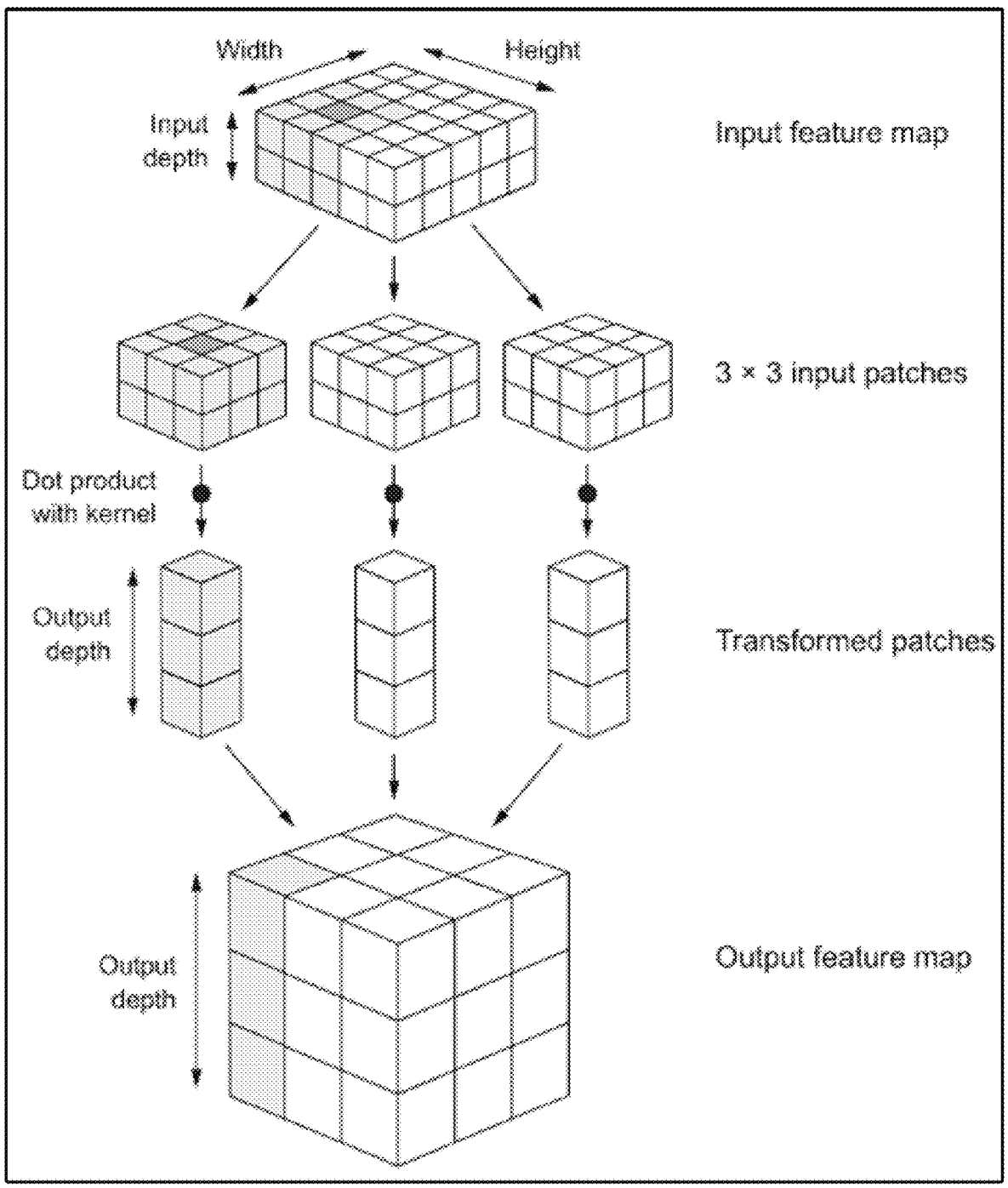
FIG. 2 depicts one implementation of workings of a convolutional neural network.

A convolution works by sliding these windows of size 3×3 or 5×5 over the 3D input feature map, stopping at every location, and extracting the 3D patch of surrounding features (shape (window_height, window_width, input_depth)). Each such 3D patch is ten transformed (via a tensor product with the same learned weight matrix, called the convolution kernel) into a 1D vector of shape (output_depth). All of these vectors are then spatially reassembled into a 3D output map of shape (height, width, output_depth). Every spatial location in the output feature map corresponds to the same location in the input feature map (for example, the lower-right corner of the output contains information about the lower-right corner of the input). For instance, with 3×3 windows, the vector output [i, j, :] comes from the 3D patch input [i−1: i+1, j−1J+1, :]. The full process is detailed in FIG. 2.

The convolutional neural network comprises convolution layers which perform the convolution operation between the input values and convolution filters (matrix of weights) that are learned over many gradient update iterations during the training. Let (m, n) be the filter size and W be the matrix of weights, then a convolution layer performs a convolution of the W with the input X by calculating the dot product W·x+b, where x is an instance of X and b is the bias. The step size by which the convolution filters slide across the input is called the stride, and the filter area (m×n) is called the receptive field. A same convolution filter is applied across different positions of the input, which reduces the number of weights learned. It also allows location invariant learning, i.e., if an important pattern exists in the input, the convolution filters learn it no matter where it is in the sequence.

Training a Convolutional Neural Network

Figure 3:
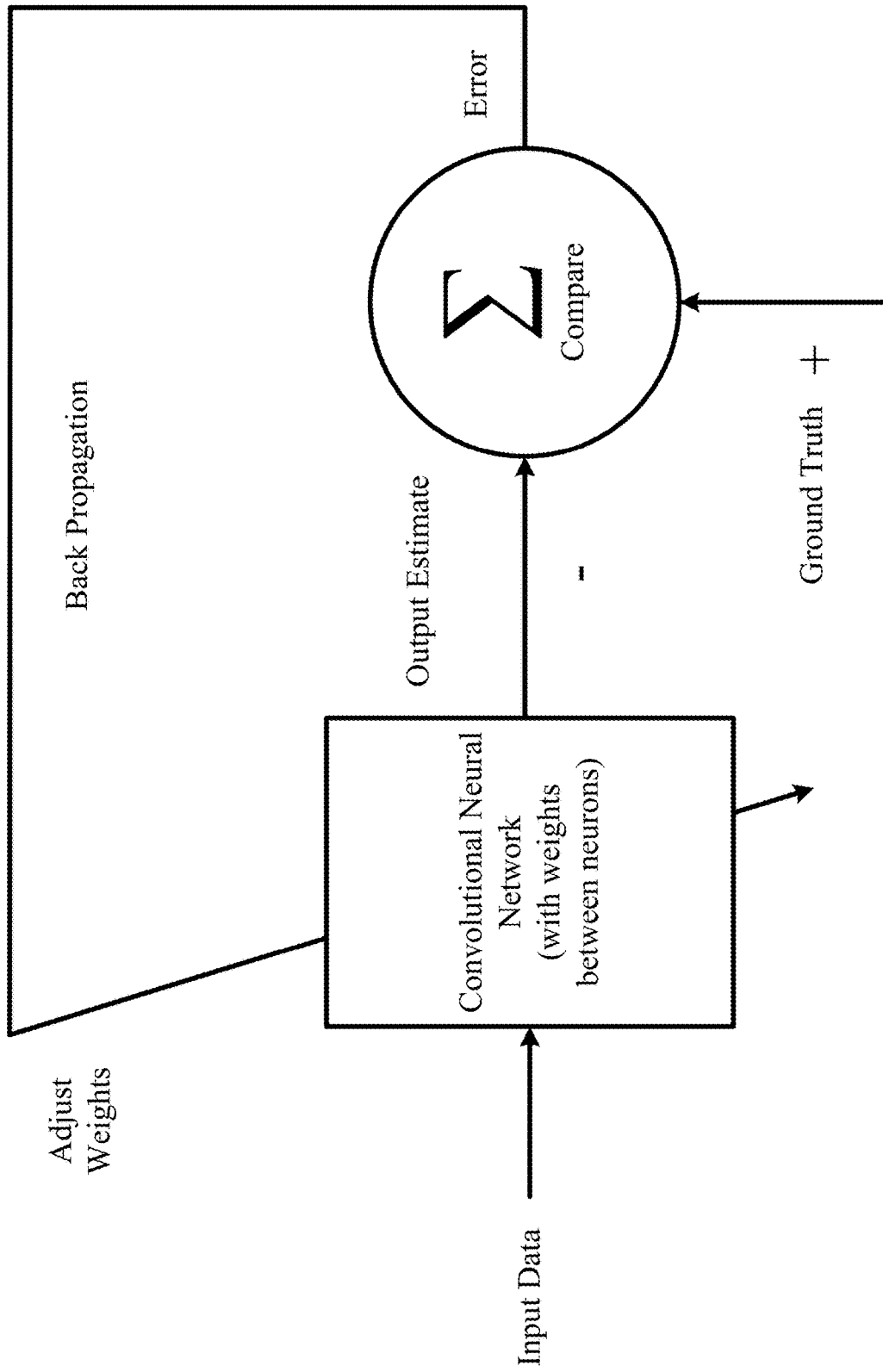
FIG. 3 depicts a block diagram of training a convolutional neural network in accordance with one implementation of the technology disclosed.

FIG. 3 depicts a block diagram of training a convolutional neural network in accordance with one implementation of the technology disclosed. The convolutional neural network is adjusted or trained so that the input data leads to a specific output estimate. The convolutional neural network is adjusted using back propagation based on a comparison of the output estimate and the ground truth until the output estimate progressively matches or approaches the ground truth.

The convolutional neural network is trained by adjusting the weights between the neurons based on the difference between the ground truth and the actual output. This is mathematically described as:

$$\Delta w_i = x_i \delta$$

where $\delta$=(ground truth)−(actual output)

In one implementation, the training rule is defined as:

$$w_{nm} \leftarrow w_{nm} + \alpha(t_m - \varphi_m)a_n$$

In the equation above: the arrow indicates an update of the value; $t_m$ is the target value of neuron m; $\varphi_m$ is the computed current output of neuron m; $a_n$ is input n; and $\alpha$ is the learning rate.

The intermediary step in the training includes generating a feature vector from the input data using the convolution layers. The gradient with respect to the weights in each layer, starting at the output, is calculated. This is referred to as the backward pass, or going backwards. The weights in the network are updated using a combination of the negative gradient and previous weights.

In one implementation, the convolutional neural network uses a stochastic gradient update algorithm (such as ADAM) that performs backward propagation of errors by means of gradient descent. One example of a sigmoid function based back propagation algorithm is described below:

$$\varphi = f(h) = \frac{1}{1 + e^{-h}}$$

In the sigmoid function above, h is the weighted sum computed by a neuron. The sigmoid function has the following derivative:

$$\frac{\partial \varphi}{\partial h} = \varphi(1 - \varphi)$$

The algorithm includes computing the activation of all neurons in the network, yielding an output for the forward pass. The activation of neuron m in the hidden layers is described as:

$$\varphi_m = \frac{1}{1 + e^{-h_m}}$$

$$h_m = \sum_{n=1}^{N} a_n w_{nm}$$

This is done for all the hidden layers to get the activation described as:

$$\varphi_k = \frac{1}{1 + e^{h_k}}$$

$$h_k = \sum_{m=1}^{M} \varphi_m v_{mk}$$

Then, the error and the correct weights are calculated per layer. The error at the output is computed as:

$$\delta_{ok} = (t_k - \varphi_k) \varphi_k (1 - \varphi_k)$$

The error in the hidden layers is calculated as:

$$\delta_{hm} = \varphi_m (1 - \varphi_m) \sum_{k=1}^{K} v_{mk} \delta_{ok}$$

The weights of the output layer are updated as:

$$v_{mk} \leftarrow v_{mk} + \alpha \delta_{ok} \varphi_m$$

The weights of the hidden layers are updated using the learning rate α as:

$$v_{nm} \leftarrow w_{nm} + \alpha \delta_{hm} a_n$$

In one implementation, the convolutional neural network uses a gradient descent optimization to compute the error across all the layers. In such an optimization, for an input feature vector x and the predicted output ŷ, the loss function is defined as l for the cost of predicting ŷ when the target is y, i.e. l(ŷ, y). The predicted output ŷ is transformed from the input feature vector x using function $f$. Function $f$ is parameterized by the weights of convolutional neural network 101, i.e. ŷ=$f_w$(x). The loss function is described as l(ŷ, y)=l($f_w$(x), y), or Q(z, w)=l($f_w$(x), y) where z is an input and output data pair (x, y). The gradient descent optimization is performed by updating the weights according to:

$$V_{t+1} = \mu V_t - \alpha \frac{1}{n} \sum_{i=1}^{N} \nabla w_t Q(z_t, w_t)$$

$$W_{t+1} = W_t + V_{t+1}$$

In the equations above, α is the learning rate. Also, the loss is computed as the average over a set of n data pairs. The computation is terminated when the learning rate α is small enough upon linear convergence. In other implementations, the gradient is calculated using only selected data pairs fed to a Nesterov's accelerated gradient and an adaptive gradient to inject computation efficiency.

In one implementation, the convolutional neural network uses a stochastic gradient descent (SGD) to calculate the cost function. A SGD approximates the gradient with respect to the weights in the loss function by computing it from only one, randomized, data pair, $Z_t$, described as:

$$V_{t+1} = \mu v - \alpha \nabla wQ(z_t, w_t)$$

$$w_{t+1} = w_t + v_{t+1}$$

In the equations above: α is the learning rate; μ is the momentum; and t is the current weight state before updating. The convergence speed of SGD is approximately O(1/t) when the learning rate α are reduced both fast and slow enough. In other implementations, the convolutional neural network uses different loss functions such as Euclidean loss and softmax loss. In a further implementation, an Adam stochastic optimizer is used by the convolutional neural network.

Convolution Layers

The convolution layers of the convolutional neural network serve as feature extractors. Convolution layers act as adaptive feature extractors capable of learning and decomposing the input data into hierarchical features. In one implementation, the convolution layers take two images as input and produce a third image as output. In such an implementation, convolution operates on two images in two-dimension (2D), with one image being the input image and the other image, called the "kernel", applied as a filter on the input image, producing an output image. Thus, for an input vector $f$ of length n and a kernel g of length m, the convolution $f$*g of $f$ and g is defined as:

$$(f * g)(i) = \sum_{j=1}^{m} g(j) \cdot f(i - j + m/2)$$

The convolution operation includes sliding the kernel over the input image. For each position of the kernel, the overlapping values of the kernel and the input image are multiplied and the results are added. The sum of products is the value of the output image at the point in the input image where the kernel is centered. The resulting different outputs from many kernels are called feature maps.

Once the convolutional layers are trained, they are applied to perform recognition tasks on new inference data. Since the convolutional layers learn from the training data, they avoid explicit feature extraction and implicitly learn from the training data. Convolution layers use convolution filter kernel weights, which are determined and updated as part of the training process. The convolution layers extract different features of the input, which are combined at higher layers. The convolutional neural network uses a various number of convolution layers, each with different convolving parameters such as kernel size, strides, padding, number of feature maps and weights.

Sub-Sampling Layers

Figure 4:
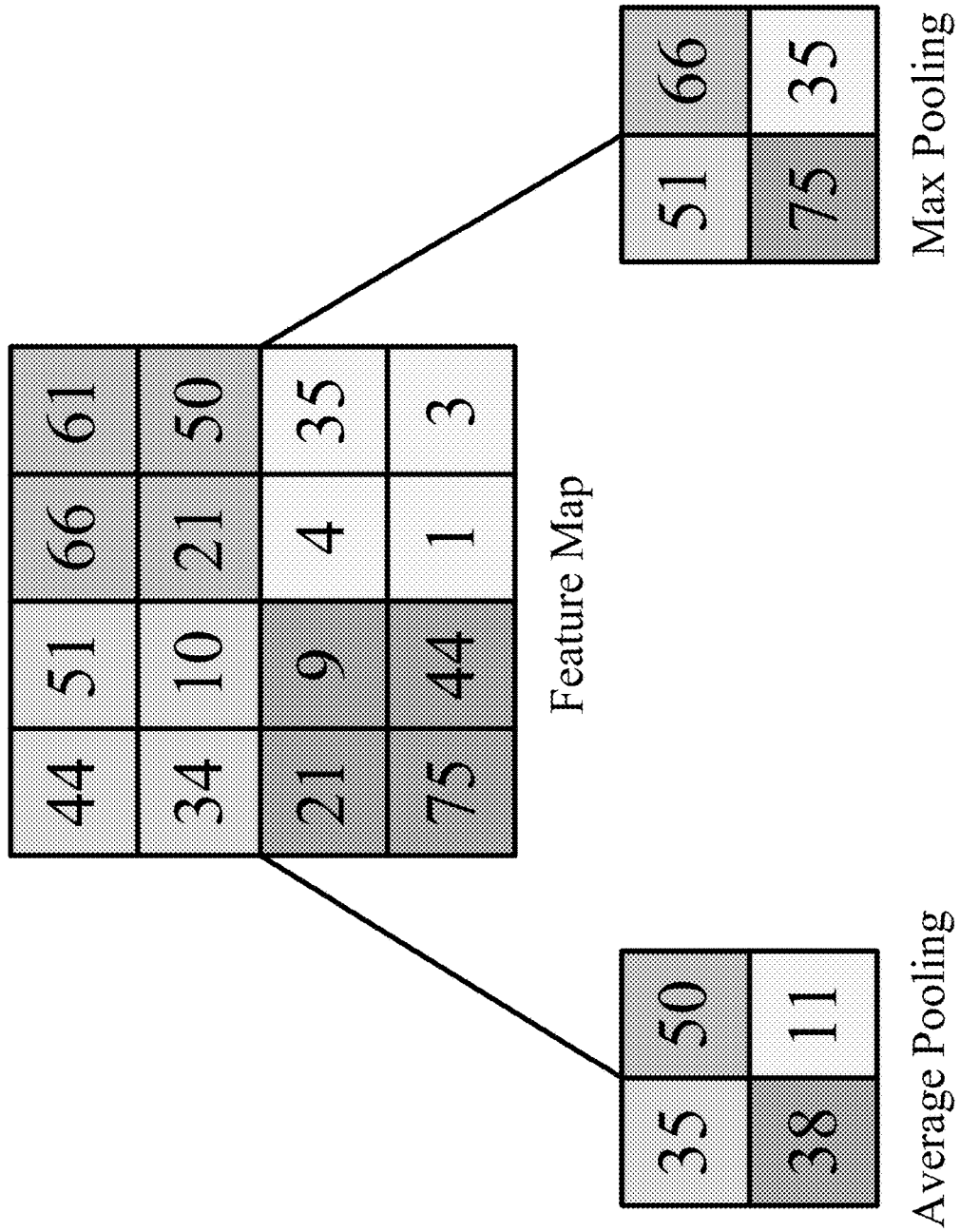
FIG. 4 is one implementation of sub-sampling layers (average/max pooling) in accordance with one implementation of the technology disclosed.

FIG. 4 is one implementation of sub-sampling layers in accordance with one implementation of the technology disclosed. Sub-sampling layers reduce the resolution of the features extracted by the convolution layers to make the extracted features or feature maps-robust against noise and distortion. In one implementation, sub-sampling layers employ two types of pooling operations, average pooling and max pooling. The pooling operations divide the input into non-overlapping two-dimensional spaces. For average pooling, the average of the four values in the region is calculated. For max pooling, the maximum value of the four values is selected.

In one implementation, the sub-sampling layers include pooling operations on a set of neurons in the previous layer by mapping its output to only one of the inputs in max pooling and by mapping its output to the average of the input in average pooling. In max pooling, the output of the pooling neuron is the maximum value that resides within the input, as described by:

$$\varphi_o = \max(\varphi_1, \varphi_2, \ldots, \varphi_N)$$

In the equation above, N is the total number of elements within a neuron set.

In average pooling, the output of the pooling neuron is the average value of the input values that reside with the input neuron set, as described by:

$$\varphi_o = \frac{1}{N}\sum_{n=1}^{N}\varphi_n$$

In the equation above, N is the total number of elements within input neuron set.

In FIG. 4, the input is of size 4×4. For 2×2 sub-sampling, a 4×4 image is divided into four non-overlapping matrices of size 2×2. For average pooling, the average of the four values is the whole-integer output. For max pooling, the maximum value of the four values in the 2×2 matrix is the whole-integer output.

Non-Linear Layers

Figure 5:
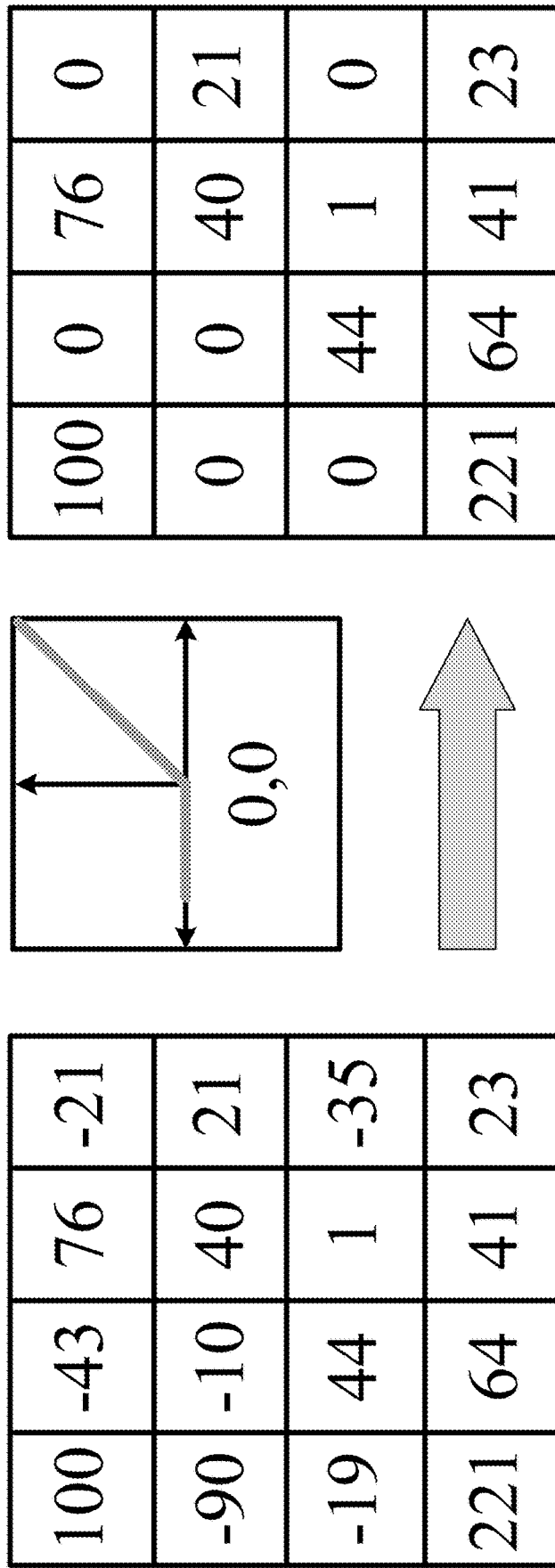
FIG. 5 shows one implementation of a ReLU non-linear layer in accordance with one implementation of the technology disclosed.

FIG. 5 shows one implementation of non-linear layers in accordance with one implementation of the technology disclosed. Non-linear layers use different non-linear trigger functions to signal distinct identification of likely features on each hidden layer. Non-linear layers use a variety of specific functions to implement the non-linear triggering, including the rectified linear units (ReLUs), hyperbolic tangent, absolute of hyperbolic tangent, sigmoid and continuous trigger (non-linear) functions. In one implementation, a ReLU activation implements the function y=max(x, 0) and keeps the input and output sizes of a layer the same. The advantage of using ReLU is that the convolutional neural network is trained many times faster. ReLU is a non-continuous, non-saturating activation function that is linear with respect to the input if the input values are larger than zero and zero otherwise. Mathematically, a ReLU activation function is described as:

$$\varphi(h) = \max(h, 0)$$

$$\varphi(h) = \begin{cases} h & \text{if } h > 0 \\ 0 & \text{if } h \leq 0 \end{cases}$$

In other implementations, the convolutional neural network uses a power unit activation function, which is a continuous, non-saturating function described by:

$$\varphi(h) = (a+bh)^c$$

In the equation above, a, b and c are parameters controlling the shift, scale and power respectively. The power activation function is able to yield x and y-antisymmetric activation if c is odd and y-symmetric activation if c is even. In some implementations, the unit yields a non-rectified linear activation.

In yet other implementations, the convolutional neural network uses a sigmoid unit activation function, which is a continuous, saturating function described by the following logistic function:

$$\varphi(h) = \frac{1}{1+e^{-\beta h}}$$

In the equation above, $\beta=1$. The sigmoid unit activation function does not yield negative activation and is only antisymmetric with respect to the y-axis.

Convolution Examples

Figure 6:
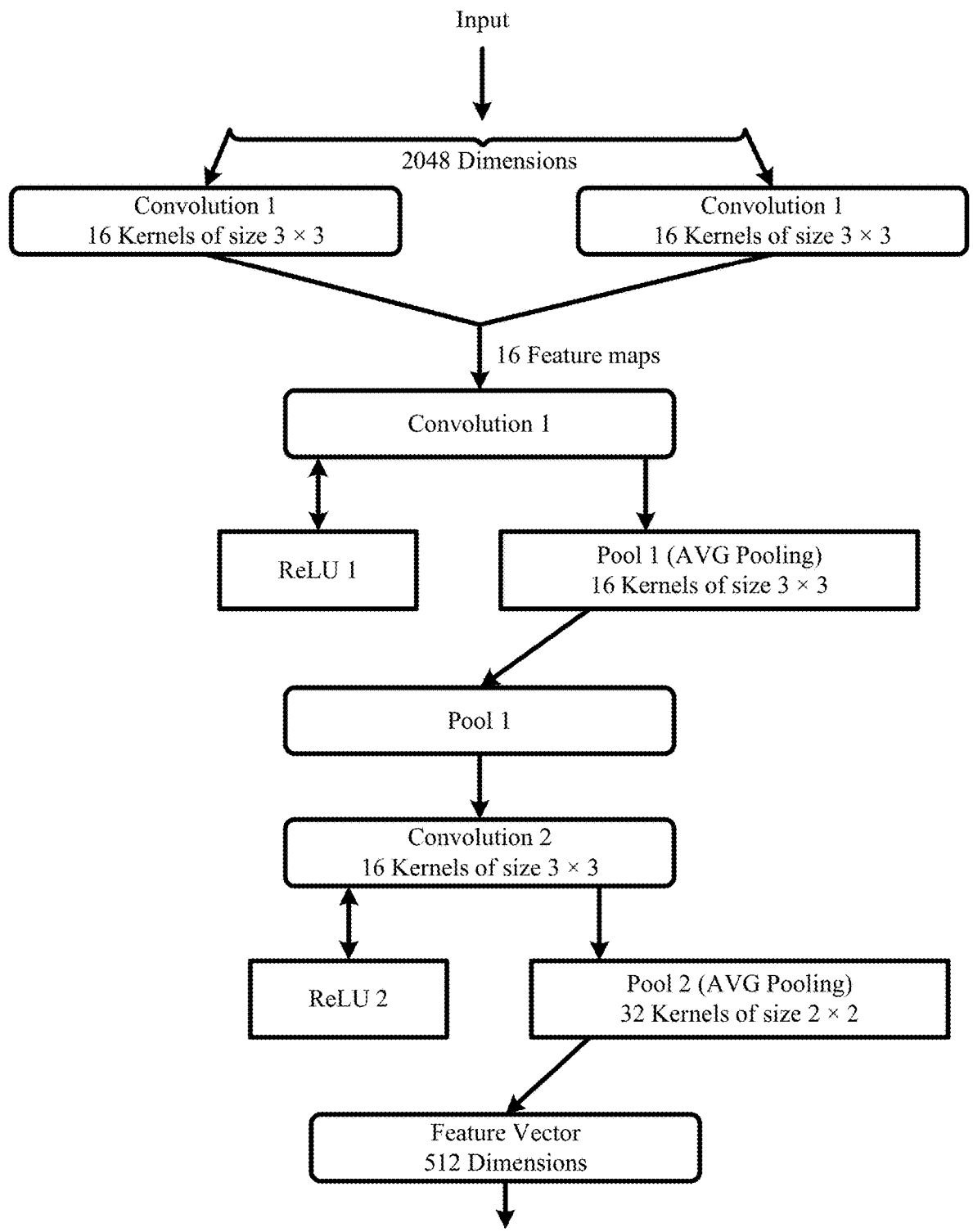
FIG. 6 depicts one implementation of a two-layer convolution of the convolution layers.

FIG. 6 depicts one implementation of a two-layer convolution of the convolution layers. In FIG. 6, an input of size 2048 dimensions is convolved. At convolution 1, the input is convolved by a convolutional layer comprising of two channels of sixteen kernels of size 3×3. The resulting sixteen feature maps are then rectified by means of the ReLU activation function at ReLU1 and then pooled in Pool 1 by means of average pooling using a sixteen channel pooling layer with kernels of size 3×3. At convolution 2, the output of Pool 1 is then convolved by another convolutional layer comprising of sixteen channels of thirty kernels with a size of 3×3. This is followed by yet another ReLU2 and average pooling in Pool 2 with a kernel size of 2×2. The convolution layers use varying number of strides and padding, for example, zero, one, two and three. The resulting feature vector is five hundred and twelve (512) dimensions, according to one implementation.

In other implementations, the convolutional neural network uses different numbers of convolution layers, sub-sampling layers, non-linear layers and fully connected layers. In one implementation, the convolutional neural network is a shallow network with fewer layers and more neurons per layer, for example, one, two or three fully connected layers with hundred (100) to two hundred (200) neurons per layer. In another implementation, the convolutional neural network is a deep network with more layers and fewer neurons per layer, for example, five (5), six (6) or eight (8) fully connected layers with thirty (30) to fifty (50) neurons per layer.

Forward Pass

The output of a neuron of row x, column y in the $l^{th}$ convolution layer and $k^{th}$ feature map for $f$ number of convolution cores in a feature map is determined by the following equation:

$$O_{x,y}^{(l,k)} = \tanh\left(\sum_{t=0}^{f-1}\sum_{r=0}^{k_h}\sum_{c=0}^{k_w} W_{(r,c)}^{(k,t)} O_{(x+r,x+c)}^{(l-1,t)} + Bias^{(l,k)}\right)$$

The output of a neuron of row x, column y in the $l^{th}$ sub-sample layer and $k^{th}$ feature map is determined by the following equation:

$$O_{x,y}^{(l,k)} = \tanh\left(W^{(k)}\sum_{r=0}^{S_h}\sum_{c=0}^{S_w} O_{(x\times S_h+r, y\times S_w+c)}^{(l-1,k)} + Bias^{(l,k)}\right)$$

The output of an $i^{th}$ neuron of the $l^{th}$ output layer is determined by the following equation:

$$O_{(l,i)} = \tanh\left(\sum_{j=0}^{H} O_{(l-1,j)} W_{(i,j)}^{l} + Bias^{(l,i)}\right)$$

Backpropagation

The output deviation of a $k^{th}$ neuron in the output layer is determined by the following equation:

$$d(O_k^o) = y_k - t_k$$

The input deviation of a $k^{th}$ neuron in the output layer is determined by the following equation:

$$d(I_k^o) = (y_k - t_k)\varphi'(v_k) = \varphi'(v_k)d(O_k^o)$$

The weight and bias variation of a $k^{th}$ neuron in the output layer is determined by the following equation:

$$\Delta W_{k,x}^o = d(I_k^o) y_{k,x}$$

$$\Delta Bias_k^o = d(I_k^o)$$

The output bias of a $k^{th}$ neuron in the hidden layer is determined by the following equation:

$$d(O_k^H) = \sum_{i=0}^{i<84} d(I_i^o) W_{i,k}$$

The input bias of a $k^{th}$ neuron in the hidden layer is determined by the following equation:

$$d(I_k^H) = \varphi'(v_k)d(O_k^H)$$

The weight and bias variation in row x, column y in a $m^{th}$ feature map of a prior layer receiving input from k neurons in the hidden layer is determined by the following equation:

$$\Delta W_{m,x,y}^{H,k} = d(I_k^H) y_{x,y}^m$$

$$\Delta Bias_k^H = d(I_k^H)$$

The output bias of row x, column y in a $m^{th}$ feature map of sub-sample layer S is determined by the following equation:

$$d(O_{x,y}^{S,m}) = \sum_k^{170} d(I_{m,x,y}^H) W_{m,x,y}^{H,k}$$

The input bias of row x, column y in a $m^{th}$ feature map of sub-sample layer S is determined by the following equation:

$$d(I_{x,y}^{S,m}) = \varphi'(v_k)d(O_{x,y}^{S,m})$$

The weight and bias variation in row x, column y in a $m^{th}$ feature map of sub-sample layer S and convolution layer C is determined by the following equation:

$$\Delta W^{S,m} = \sum_{x=0}^{fh}\sum_{y=0}^{fw} d(I_{[x/2],[y/2]}^{S,m}) O_{x,y}^{C,m}$$

$$\Delta Bias^{S,m} = \sum_{x=0}^{fh}\sum_{y=0}^{fw} d(O_{x,y}^{S,m})$$

The output bias of row x, column y in a $k^{th}$ feature map of convolution layer C is determined by the following equation:

$$d(O_{x,y}^{C,k}) = d(I_{[x/2],[y/2]}^{S,k}) W^k$$

The input bias of row x, column y in a $k^{th}$ feature map of convolution layer C is determined by the following equation:

$$d(I_{x,y}^{C,k}) = \varphi'(v_k)d(O_{x,y}^{C,k})$$

The weight and bias variation in row r, column c in an $m^{th}$ convolution core of a $k^{th}$ feature map of Pt convolution layer C:

$$\Delta W_{r,c}^{k,m} = \sum_{x=0}^{fh}\sum_{y=0}^{fw} d(I_{x,y}^{C,k}) O_{x+r,y+c}^{l-1,m}$$

$$\Delta Bias^{C,k} = \sum_{x=0}^{fh}\sum_{y=0}^{fw} d(I_{x,y}^{C,k})$$

Residual Connections

Figure 7:
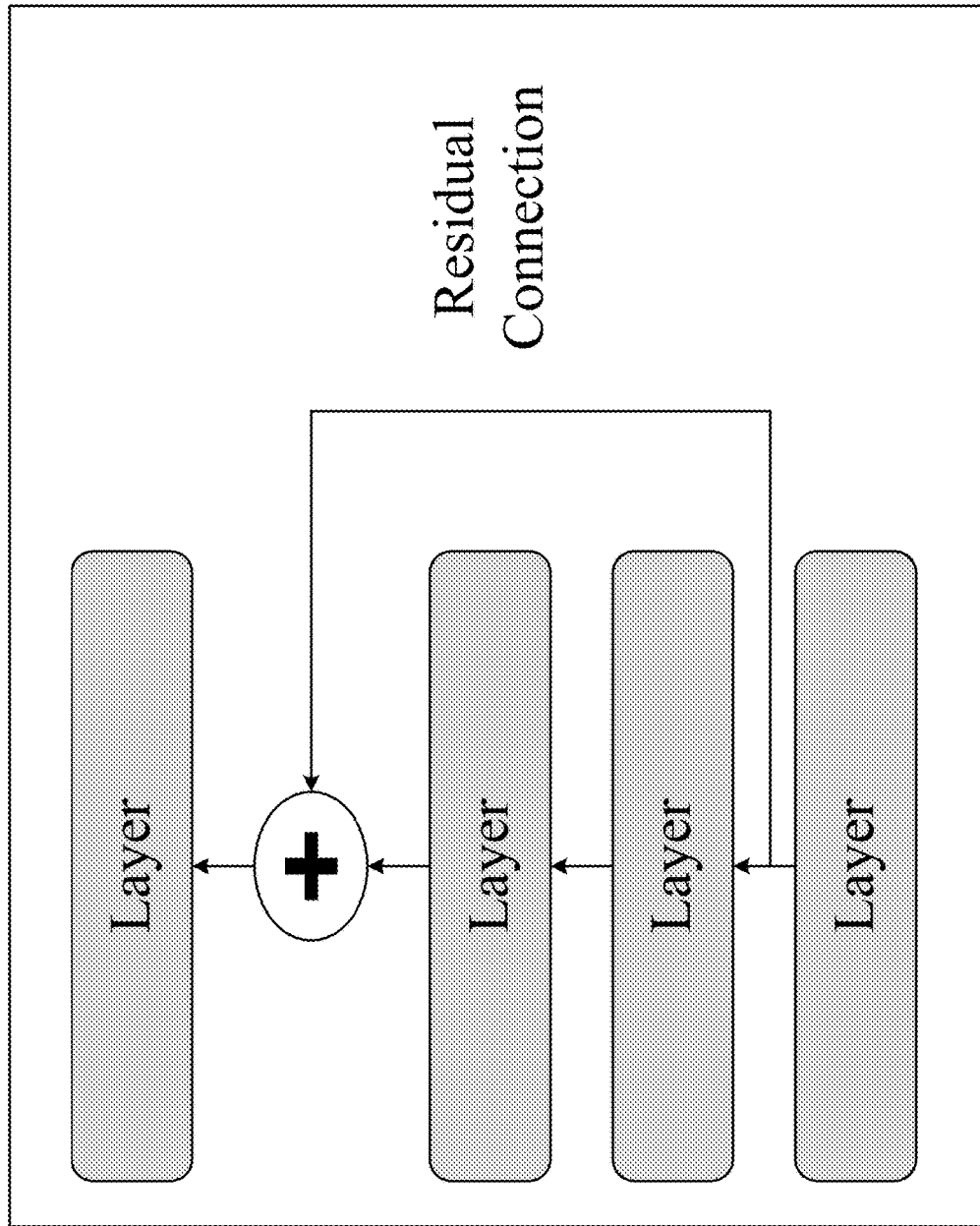
FIG. 7 depicts a residual connection that reinjects prior information downstream via feature-map addition.

FIG. 7 depicts a residual connection that reinjects prior information downstream via feature-map addition. A residual connection comprises reinjecting previous representations into the downstream flow of data by adding a past output tensor to a later output tensor, which helps prevent information loss along the data-processing flow. Residual connections tackle two common problems that plague any large-scale deep-learning model: vanishing gradients and representational bottlenecks. In general, adding residual connections to any model that has more than 10 layers is likely to be beneficial. As discussed above, a residual connection comprises making the output of an earlier layer available as input to a later layer, effectively creating a shortcut in a sequential network. Rather than being concatenated to the later activation, the earlier output is summed with the later activation, which assumes that both activations are the same size. If they are of different sizes, a linear transformation to reshape the earlier activation into the target shape can be used.

Residual Learning and Skip-Connections

Figure 8:
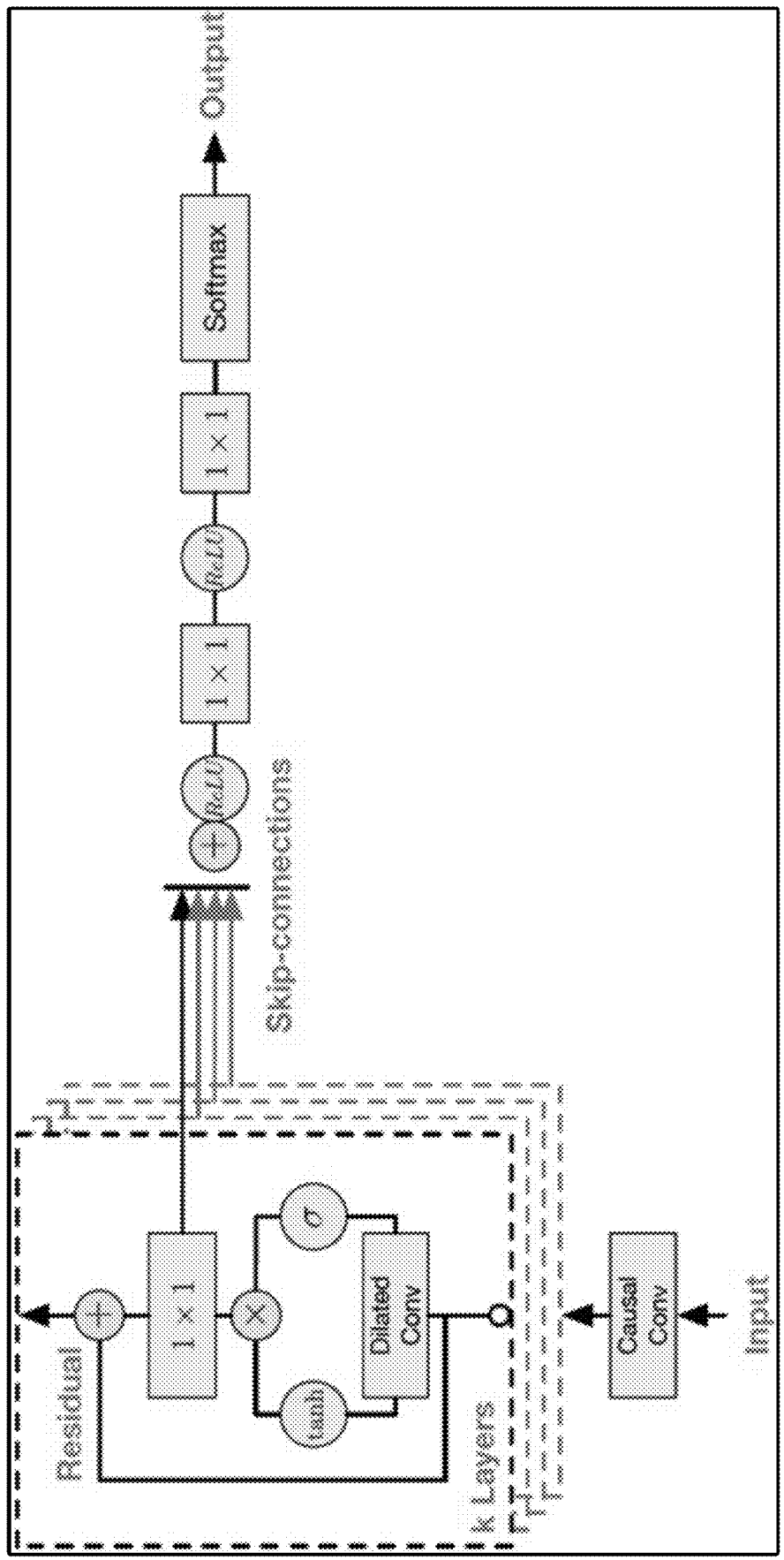
FIG. 8 depicts one implementation of residual blocks and skip-connections.

FIG. 8 depicts one implementation of residual blocks and skip-connections. The main idea of residual learning is that the residual mapping is much easier to be learned than the original mapping. Residual network stacks a number of residual units to alleviate the degradation of training accuracy. Residual blocks make use of special additive skip connections to combat vanishing gradients in deep neural networks. At the beginning of a residual block, the data flow is separated into two streams: the first carries the unchanged input of the block, while the second applies weights and non-linearities. At the end of the block, the two streams are merged using an element-wise sum. The main advantage of such constructs is to allow the gradient to flow through the network more easily.

Benefited from residual network, deep convolutional neural networks (CNNs) can be easily trained and improved accuracy has been achieved for image classification and object detection. Convolutional feed-forward networks connect the output of the $l^{th}$ layer as input to the $(l+1)^{th}$ layer, which gives rise to the following layer transition: $x_l = H_l(x_{l-1})$. Residual blocks add a skip-connection that bypasses the non-linear transformations with an identify function: $x_l = H_l(x_{l-1}) + x_{l-1}$. An advantage of residual blocks is that the gradient can flow directly through the identity function from later layers to the earlier layers. However, the identity function and the output of $H_l$ are combined by summation, which may impede the information flow in the network.

Batch Normalization

Batch normalization is a method for accelerating deep network training by making data standardization an integral part of the network architecture. Batch normalization can adaptively normalize data even as the mean and variance change over time during training. It works by internally maintaining an exponential moving average of the batch-wise mean and variance of the data seen during training. The main effect of batch normalization is that it helps with gradient propagation—much like residual connections—and thus allows for deep networks. Some very deep networks can only be trained if they include multiple Batch Normalization layers.

Batch normalization can be seen as yet another layer that can be inserted into the model architecture, just like the fully connected or convolutional layer. The BatchNormalization layer is typically used after a convolutional or densely connected layer. It can also be used before a convolutional or densely connected layer. Both implementations can be used by the technology disclosed and are shown in FIG. 12. The BatchNormalization layer takes an axis argument, which specifies the feature axis that should be normalized. This argument defaults to −1, the last axis in the input tensor. This is the correct value when using Dense layers, Conv1D layers, RNN layers, and Conv2D layers with data_format set to "channels_last". But in the niche use case of Conv2D layers with data_format set to "channels_first", the features axis is axis 1; the axis argument in BatchNormalization can be set to 1.

Batch normalization provides a definition for feed-forwarding the input and computing the gradients with respect to the parameters and its own input via a backward pass. In practice, batch normalization layers are inserted after a convolutional or fully connected layer, but before the outputs are fed into an activation function. For convolutional layers, the different elements of the same feature map—i.e. the activations—at different locations are normalized in the same way in order to obey the convolutional property. Thus, all activations in a mini-batch are normalized over all locations, rather than per activation.

The internal covariate shift is the major reason why deep architectures have been notoriously slow to train. This stems from the fact that deep networks do not only have to learn a new representation at each layer, but also have to account for the change in their distribution.

The covariate shift in general is a known problem in the deep learning domain and frequently occurs in real-world problems. A common covariate shift problem is the difference in the distribution of the training and test set which can lead to suboptimal generalization performance. This problem is usually handled with a standardization or whitening preprocessing step. However, especially the whitening operation is computationally expensive and thus impractical in an online setting, especially if the covariate shift occurs throughout different layers.

The internal covariate shift is the phenomenon where the distribution of network activations change across layers due to the change in network parameters during training. Ideally, each layer should be transformed into a space where they have the same distribution but the functional relationship stays the same. In order to avoid costly calculations of covariance matrices to decorrelate and whiten the data at every layer and step, we normalize the distribution of each input feature in each layer across each mini-batch to have zero mean and a standard deviation of one.

Forward Pass

During the forward pass, the mini-batch mean and variance are calculated. With these mini-batch statistics, the data is normalized by subtracting the mean and dividing by the standard deviation. Finally, the data is scaled and shifted with the learned scale and shift parameters. The batch normalization forward pass $f_{BN}$ is depicted in FIG. 9.

In FIG. 9, $\mu_\beta$ is the batch mean and $\sigma_\beta^2$ is the batch variance, respectively. The learned scale and shift parameters are denoted by $\gamma$ and $\beta$, respectively. For clarity, the batch normalization procedure is described herein per activation and omit the corresponding indices.

Since normalization is a differentiable transform, the errors are propagated into these learned parameters and are thus able to restore the representational power of the network by learning the identity transform. Conversely, by learning scale and shift parameters that are identical to the corresponding batch statistics, the batch normalization transform would have no effect on the network, if that was the optimal operation to perform. At test time, the batch mean and variance are replaced by the respective population statistics since the input does not depend on other samples from a mini-batch. Another method is to keep running averages of the batch statistics during training and to use these to compute the network output at test time. At test time, the batch normalization transform can be expressed as illustrated in FIG. 10. In FIG. 10, $\mu_D$ and $\sigma_D^2$ denote the population mean and variance, rather than the batch statistics, respectively.

Backward Pass

Since normalization is a differentiable operation, the backward pass can be computed as depicted in FIG. 11.

Figure 13:
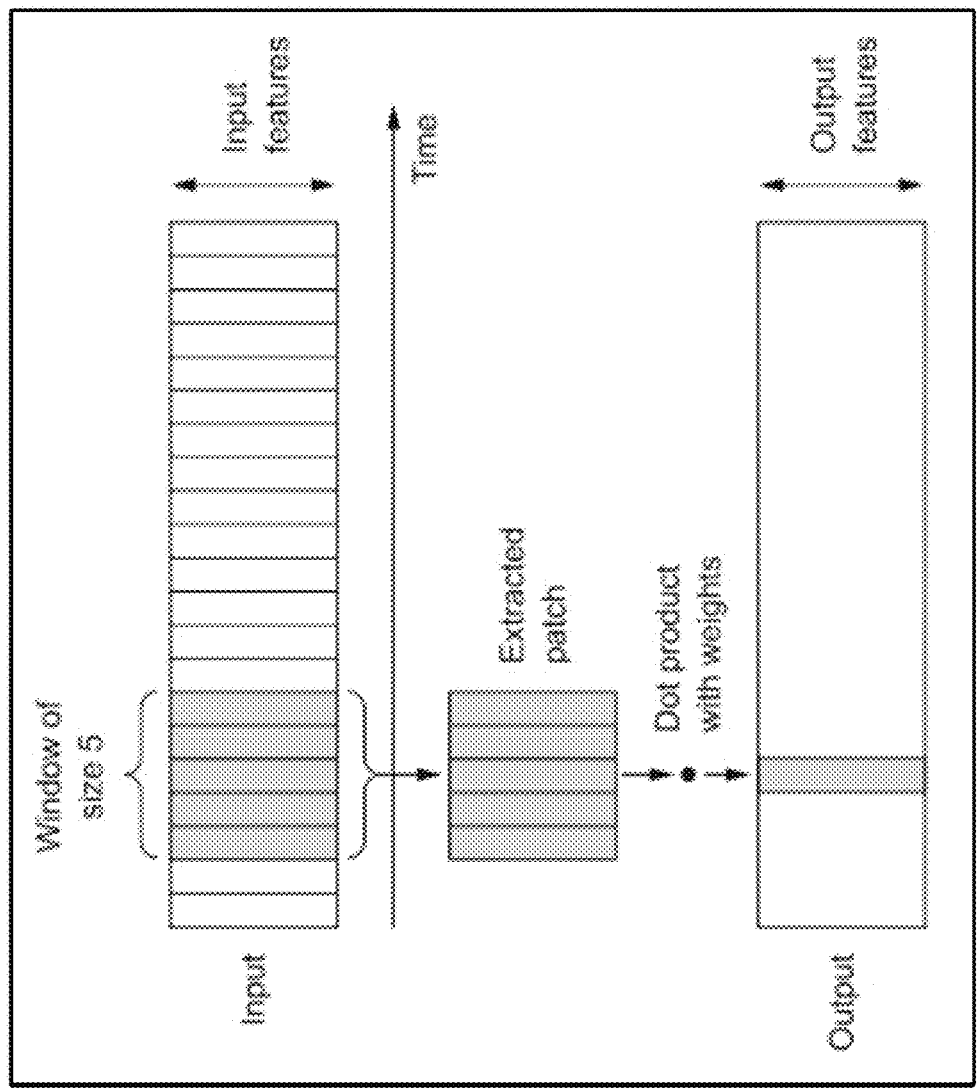
FIG. 13 shows one implementation of 1D convolution.

1D Convolution 1D convolutions extract local 1D patches or subsequences from sequences, as shown in FIG. 13. 1D convolution obtains each output timestep from a temporal patch in the input sequence. 1D convolution layers recognize local patterns in a sequence. Because the same input transformation is performed on every patch, a pattern learned at a certain position in the input sequences can be later recognized at a different position, making 1D convolution layers translation invariant for temporal translations. For instance, a 1D convolution layer processing sequences of bases using convolution windows of size 5 should be able to learn bases or base sequences of length 5 or less, and it should be able to recognize the base motifs in any context in an input sequence. A base-level 1D convolution is thus able to learn about base morphology.

Global Average Pooling

FIG. 14 illustrates how global average pooling (GAP) works. Global average pooling can be use used to replace fully connected (FC) layers for classification, by taking the spatial average of features in the last layer for scoring. The reduces the training load and bypasses overfitting issues. Global average pooling applies a structural prior to the model and it is equivalent to linear transformation with predefined weights. Global average pooling reduces the number of parameters and eliminates the fully connected layer. Fully connected layers are typically the most parameter and connection intensive layers, and global average pooling provides much lower-cost approach to achieve similar results. The main idea of global average pooling is to generate the average value from each last layer feature map as the confidence factor for scoring, feeding directly into the softmax layer.

Global average pooling have three benefits: (1) there are no extra parameters in global average pooling layers thus overfitting is avoided at global average pooling layers; (2) since the output of global average pooling is the average of the whole feature map, global average pooling will be more robust to spatial translations; and (3) because of the huge number of parameters in fully connected layers which usually take over 50% in all the parameters of the whole network, replacing them by global average pooling layers can significantly reduce the size of the model, and this makes global average pooling very useful in model compression.

Global average pooling makes sense, since stronger features in the last layer are expected to have a higher average value. In some implementations, global average pooling can be used as a proxy for the classification score. The feature maps under global average pooling can be interpreted as confidence maps, and force correspondence between the feature maps and the categories. Global average pooling can be particularly effective if the last layer features are at a sufficient abstraction for direct classification; however, global average pooling alone is not enough if multilevel features should be combined into groups like parts models, which is best performed by adding a simple fully connected layer or other classifier after the global average pooling.

Deep Learning in Genomics

Genetic variations can help explain many diseases. Every human being has a unique genetic code and there are lots of genetic variants within a group of individuals. Most of the deleterious genetic variants have been depleted from genomes by natural selection. It is important to identify which genetics variations are likely to be pathogenic or deleterious. This will help researchers focus on the likely pathogenic genetic variants and accelerate the pace of diagnosis and cure of many diseases.

Modeling the properties and functional effects (e.g., pathogenicity) of variants is an important but challenging task in the field of genomics. Despite the rapid advancement of functional genomic sequencing technologies, interpretation of the functional consequences of variants remains a great challenge due to the complexity of cell type-specific transcription regulation systems.

Advances in biochemical technologies over the past decades have given rise to next generation sequencing (NGS) platforms that quickly produce genomic data at much lower costs than ever before. Such overwhelmingly large volumes of sequenced DNA remain difficult to annotate. Supervised machine learning algorithms typically perform well when large amounts of labeled data are available. In bioinformatics and many other data-rich disciplines, the process of labeling instances is costly; however, unlabeled instances are inexpensive and readily available. For a scenario in which the amount of labeled data is relatively small and the amount of unlabeled data is substantially larger, semi-supervised learning represents a cost-effective alternative to manual labeling.

An opportunity arises to use semi-supervised algorithms to construct deep learning-based pathogenicity classifiers that accurately predict pathogenicity of variants. Databases of pathogenic variants that are free from human ascertainment bias may result.

Regarding pathogenicity classifiers, deep neural networks are a type of artificial neural networks that use multiple nonlinear and complex transforming layers to successively model high-level features. Deep neural networks provide feedback via backpropagation which carries the difference between observed and predicted output to adjust parameters. Deep neural networks have evolved with the availability of large training datasets, the power of parallel and distributed computing, and sophisticated training algorithms. Deep neural networks have facilitated major advances in numerous domains such as computer vision, speech recognition, and natural language processing.

Convolutional neural networks (CNNs) and recurrent neural networks (RNNs) are components of deep neural networks. Convolutional neural networks have succeeded particularly in image recognition with an architecture that comprises convolution layers, nonlinear layers, and pooling layers. Recurrent neural networks are designed to utilize sequential information of input data with cyclic connections among building blocks like perceptrons, long short-term memory units, and gated recurrent units. In addition, many other emergent deep neural networks have been proposed for limited contexts, such as deep spatio-temporal neural networks, multi-dimensional recurrent neural networks, and convolutional auto-encoders.

The goal of training deep neural networks is optimization of the weight parameters in each layer, which gradually combines simpler features into complex features so that the most suitable hierarchical representations can be learned from data. A single cycle of the optimization process is organized as follows. First, given a training dataset, the forward pass sequentially computes the output in each layer and propagates the function signals forward through the network. In the final output layer, an objective loss function measures error between the inferenced outputs and the given labels. To minimize the training error, the backward pass uses the chain rule to backpropagate error signals and compute gradients with respect to all weights throughout the neural network. Finally, the weight parameters are updated using optimization algorithms based on stochastic gradient descent. Whereas batch gradient descent performs parameter updates for each complete dataset, stochastic gradient descent provides stochastic approximations by performing the updates for each small set of data examples. Several optimization algorithms stem from stochastic gradient descent. For example, the Adagrad and Adam training algorithms perform stochastic gradient descent while adaptively modifying learning rates based on update frequency and moments of the gradients for each parameter, respectively.

Another core element in the training of deep neural networks is regularization, which refers to strategies intended to avoid overfitting and thus achieve good generalization performance. For example, weight decay adds a penalty term to the objective loss function so that weight parameters converge to smaller absolute values. Dropout randomly removes hidden units from neural networks during training and can be considered an ensemble of possible subnetworks. To enhance the capabilities of dropout, a new activation function, maxout, and a variant of dropout for recurrent neural networks called rnnDrop have been proposed. Furthermore, batch normalization provides a new regularization method through normalization of scalar features for each activation within a mini-batch and learning each mean and variance as parameters.

Given that sequenced data are multi- and high-dimensional, deep neural networks have great promise for bioinformatics research because of their broad applicability and enhanced prediction power. Convolutional neural networks have been adapted to solve sequence-based problems in genomics such as motif discovery, pathogenic variant identification, and gene expression inference. Convolutional neural networks use a weight-sharing strategy that is especially useful for studying DNA because it can capture sequence motifs, which are short, recurring local patterns in DNA that are presumed to have significant biological functions. A hallmark of convolutional neural networks is the use of convolution filters. Unlike traditional classification approaches that are based on elaborately-designed and manually-crafted features, convolution filters perform adaptive learning of features, analogous to a process of mapping raw input data to the informative representation of knowledge. In this sense, the convolution filters serve as a series of motif scanners, since a set of such filters is capable of recognizing relevant patterns in the input and updating themselves during the training procedure. Recurrent neural networks can capture long-range dependencies in sequential data of varying lengths, such as protein or DNA sequences.

Therefore, a powerful computational model for predicting the pathogenicity of variants can have enormous benefits for both basic science and translational research.

Unlike earlier models which employ a large number of human-engineered features and meta-classifiers, we apply a simple deep learning residual network which takes as input only the amino acid sequence flanking the variant of interest and the orthologous sequence alignments in other species. To provide the network with information about protein structure, we train two separate networks to learn secondary structure and solvent accessibility from sequence alone, and incorporate these as sub-networks in the larger deep learning network to predict effects on protein structure. Using sequence as a starting point avoids potential biases in protein structure and functional domain annotation, which may be incompletely ascertained or inconsistently applied.

We use semi-supervised learning to overcome the problem of the training set containing only variants with benign labels, by initially training an ensemble of networks to separate likely benign primate variants versus random unknown variants that are matched for mutation rate and sequencing coverage. This ensemble of networks is used to score the complete set of unknown variants and influence the selection of unknown variants to seed the next iteration of the classifier by biasing towards unknown variants with more pathogenic predicted consequence, taking gradual steps at each iteration to prevent the model from prematurely converging to a suboptimal result.

Common primate variation also provides a clean validation dataset for evaluating existing methods that is completely independent of previously used training data, which has been hard to evaluate objectively because of the proliferation of meta-classifiers. We evaluated the performance of our model, along with four other popular classification algorithms (Sift, Polyphen2, CADD, M-CAP), using 10,000 held-out primate common variants. Because roughly 50% of all human missense variants would be removed by natural selection at common allele frequencies, we calculated the 50th-percentile score for each classifier on a set of randomly picked missense variants that were matched to the 10,000 held-out primate common variants by mutational rate, and used that threshold to evaluate the held-out primate common variants. The accuracy of our deep learning model was significantly better than the other classifiers on this independent validation dataset, using either deep learning networks that were trained only on human common variants, or using both human common variants and primate variants.

Recent trio sequencing studies have catalogued thousands of de novo mutations in patients with neurodevelopmental disorders and their healthy siblings, enabling assessment of the strength of various classification algorithms in separating de novo missense mutations in cases versus controls. For each of the four classification algorithms, we scored each de novo missense variant in cases versus controls, and report the p-value from the Wilcoxon rank-sum test of the difference between the two distributions, showing that the deep learning method trained on primate variants ($p\sim10^{-33}$) performed far better than the other classifiers ($p\sim10^{-13}$ to $10^{19}$) on this clinical scenario. From the ~1.3-fold enrichment of de novo missense variants over expectation previously reported for this cohort, and prior estimates that ~20% of missense variants produce loss-of-function effects, we would expect a perfect classifier to separate the two classes with a p-value of $p\sim10^{-40}$, indicating that our classifier still has room for improvement.

The accuracy of the deep learning classifier scales with the size of the training dataset, and variation data from each of the six primate species independently contributes to boosting the accuracy of the classifier. The large number and diversity of extant non-human primate species, along with evidence showing that the selective pressures on protein-altering variants are largely concordant within the primate lineage, suggests systematic primate population sequencing as an effective strategy to classify the millions of human variants of unknown significance that currently limit clinical genome interpretation. Of the 504 known non-human primate species, roughly 60% face extinction due to hunting and habitat loss, motivating urgency for a worldwide conservation effort that would benefit both these unique and irreplaceable species and our own.

Deep Learning Network for Variant Pathogenicity Classification

The technology disclosed provides a deep learning network for variant pathogenicity classification. The importance of variant classification for clinical applications has inspired numerous attempts to use supervised machine learning to address the problem, but these efforts have been hindered by the lack of an adequately sized truth dataset containing confidently labeled benign and pathogenic variants for training.

Existing databases of human expert curated variants do not represent the entire genome, with ~50% of the variants in the ClinVar database coming from only 200 genes (~1% of human protein-coding genes). Moreover, systematic studies identify that many human expert annotations have questionable supporting evidence, underscoring the difficulty of interpreting rare variants that may be observed in only a single patient. Although human expert interpretation has become increasingly rigorous, classification guidelines are largely formulated around consensus practices and are at risk of reinforcing existing tendencies. To reduce human interpretation biases, recent classifiers have been trained on common human polymorphisms or fixed human-chimpanzee substitutions, but these classifiers also use as their input the prediction scores of earlier classifiers that were trained on human curated databases. Objective benchmarking of the performance of these various methods has been elusive in the absence of an independent, bias-free truth dataset.

Variation from the six non-human primates (chimpanzee, bonobo, gorilla, orangutan, rhesus, and marmoset) contributes over 300,000 unique missense variants that are non-overlapping with common human variation, and largely represent common variants of benign consequence that have been through the sieve of purifying selection, greatly enlarging the training dataset available for machine learning approaches. On average, each primate species contributes more variants than the whole of the ClinVar database (~42,000 missense variants as of November 2017, after excluding variants of uncertain significance and those with conflicting annotations). Additionally, this content is free from biases in human interpretation.

Figure 16:
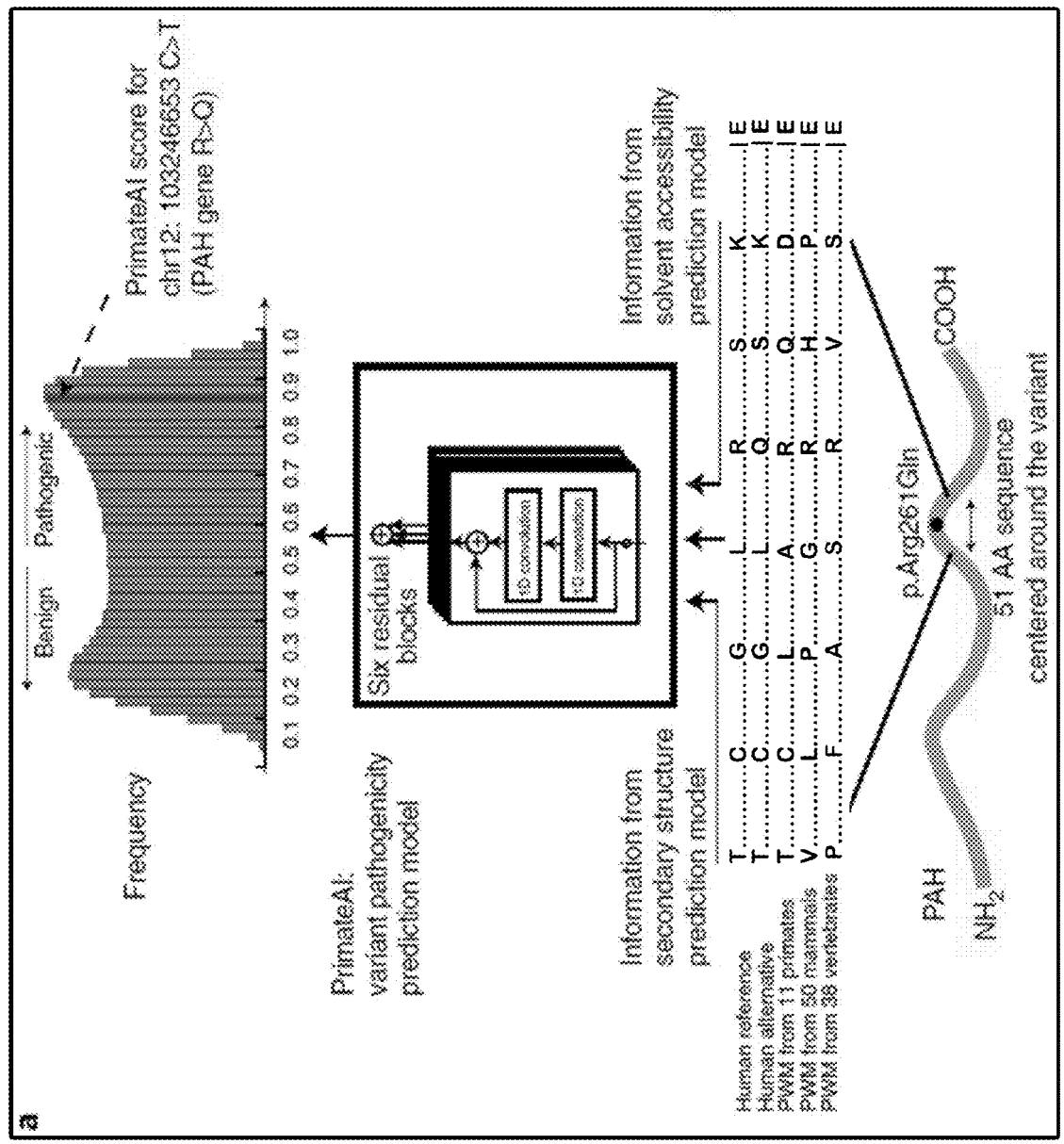
FIG. 16 shows an example architecture of a deep residual network for pathogenicity prediction, referred to herein as "PrimateAI".
Figure 17:
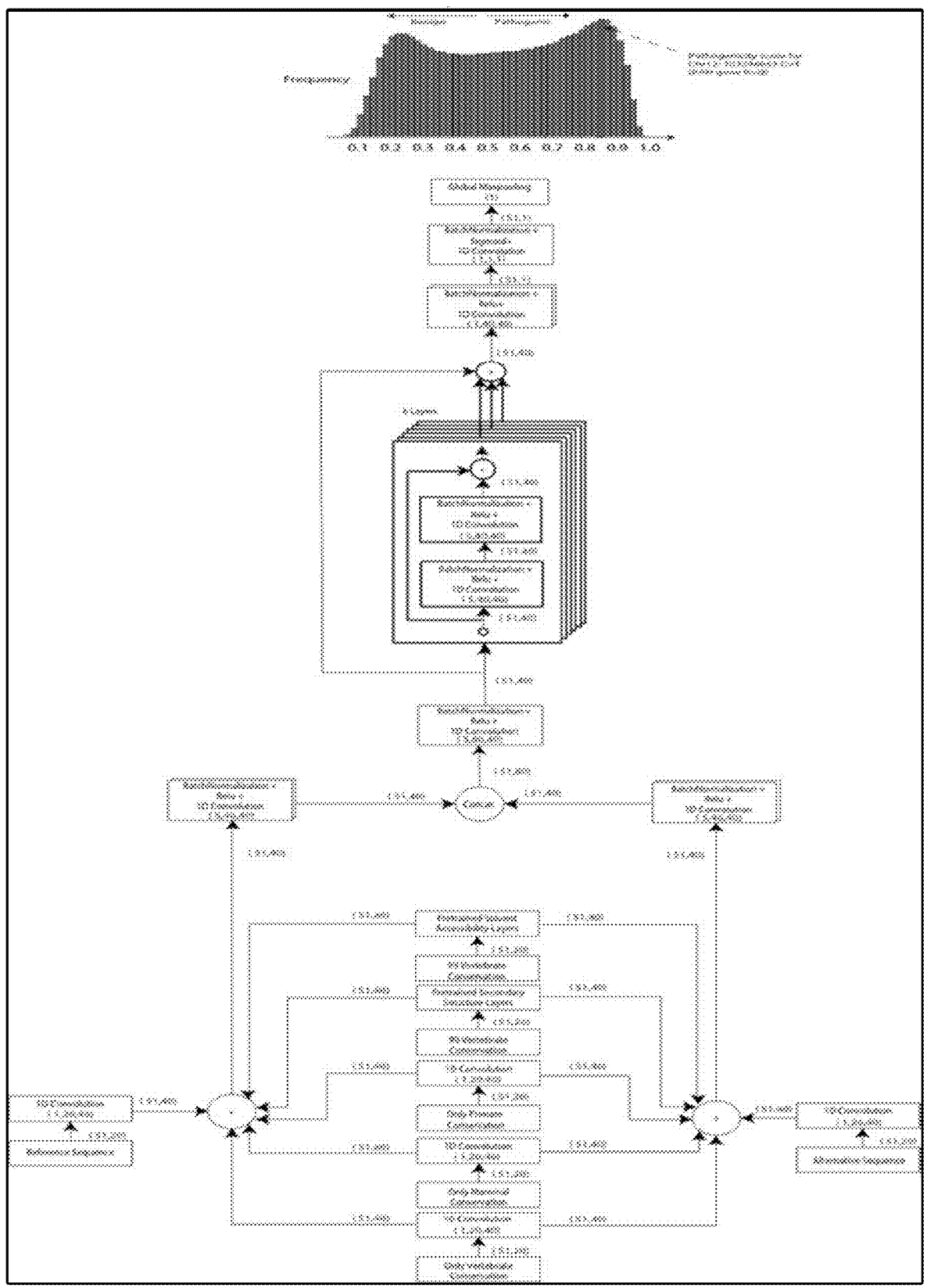
FIG. 17 depicts a schematic illustration of PrimateAI, the deep learning network architecture for pathogenicity classification.
Figure 19:
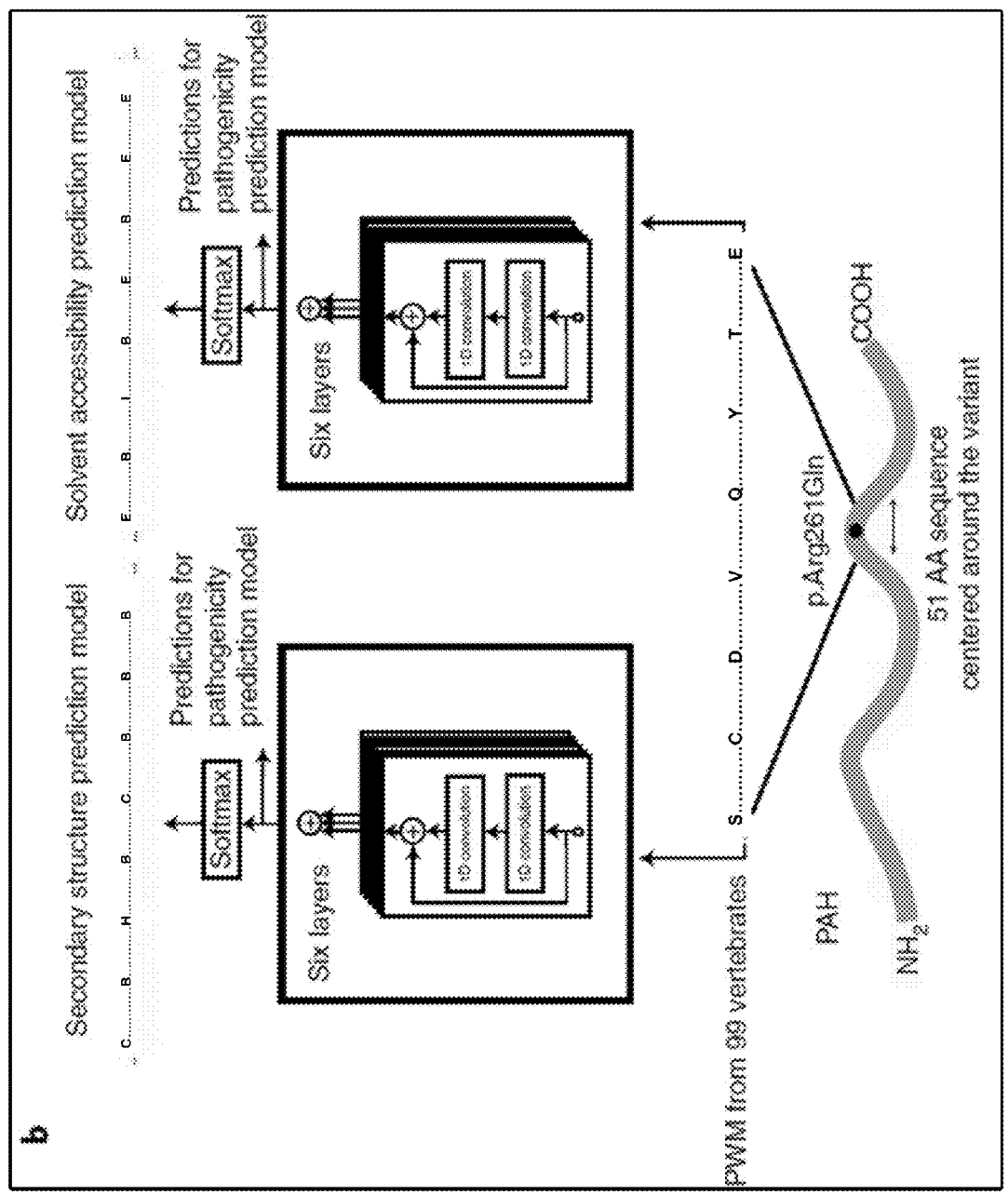
FIGS. 19 and 20 illustrate the deep learning network architecture used for predicting secondary structure and solvent accessibility of proteins.
Figure 20:
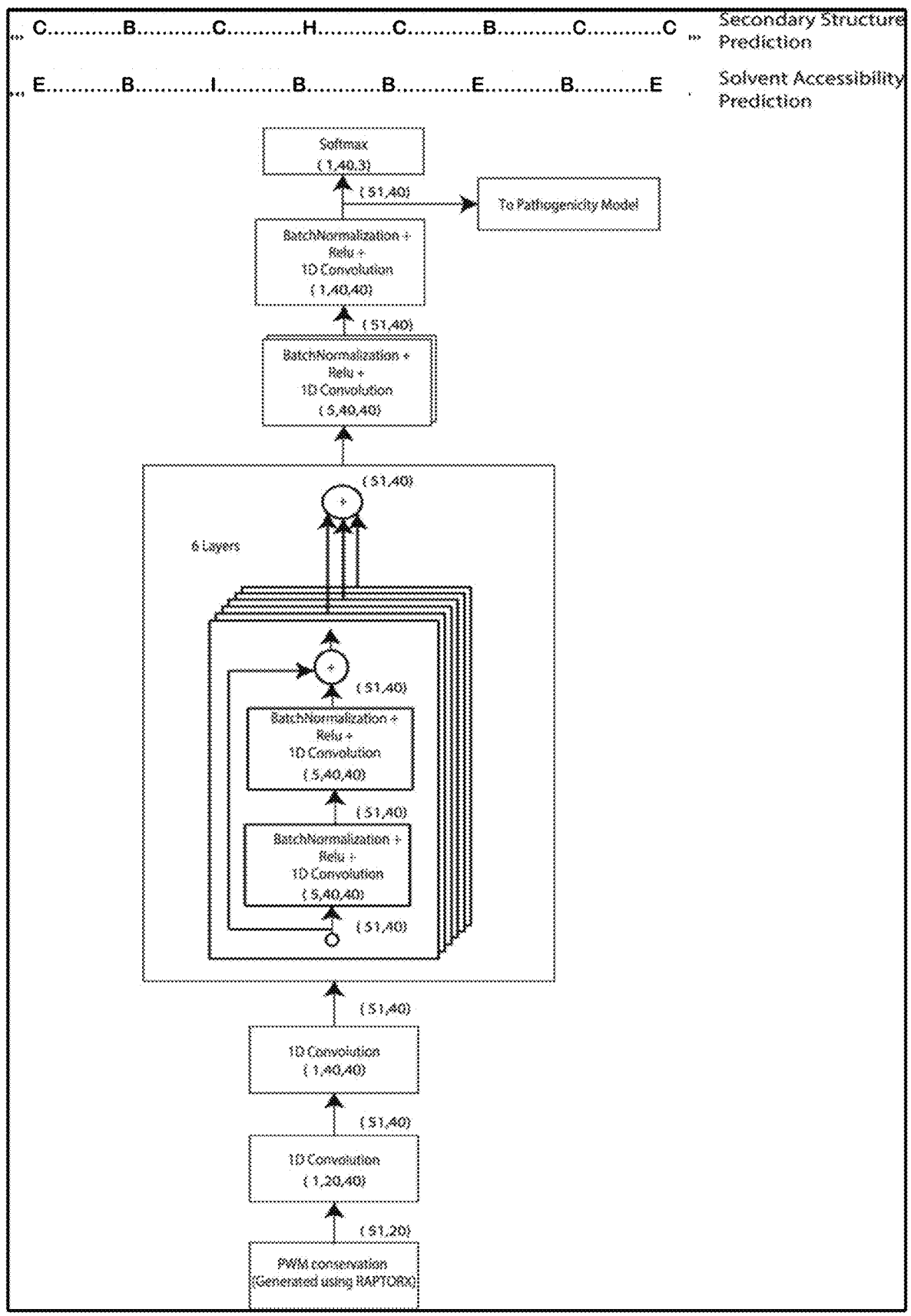

Using a dataset comprising common human variants (AF>0.1%) and primate variation, we trained a novel deep residual network, PrimateAI, which takes as input the amino acid sequence flanking the variant of interest and the orthologous sequence alignments in other species (FIG. 16 and FIG. 17). Unlike existing classifiers that employ human-engineered features, our deep learning network learns to extract features directly from the primary sequence. To incorporate information about protein structure, we trained separate networks to predict the secondary structure and solvent accessibility from the sequence alone, and then included these as subnetworks in the full model (FIG. 19 and FIG. 20). Given the small number of human proteins that have been successfully crystallized, inferring structure from the primary sequence has the advantage of avoiding biases due to incomplete protein structure and functional domain annotation. The total depth of the network, with protein structure included, was 36 layers of convolutions, comprising roughly 400,000 trainable parameters.

To train a classifier using only variants with benign labels, we framed the prediction problem as whether a given mutation is likely to be observed as a common variant in the population. Several factors influence the probability of observing a variant at high allele frequencies, of which we are interested only in deleteriousness; other factors include mutation rate, technical artifacts such as sequencing coverage, and factors impacting neutral genetic drift such as gene conversion.

Generation of Benign and Unlabeled Variants for Model Training

We constructed a benign training dataset of largely common benign missense variants from human and non-human primates for machine learning. The dataset comprises common human variants (>0.1% allele frequency; 83,546 variants), and variants from chimpanzee, bonobo, gorilla, and orangutan, rhesus, and marmoset (301,690 unique primate variants).

We trained the deep learning network to discriminate between a set of labeled benign variants and an unlabeled set of variants that were matched to control for trinucleotide context, sequencing coverage, and alignability between the species and human. To obtain an unlabeled training dataset, we started with all possible missense variants in canonical coding regions. We excluded variants that were observed in the 123,136 exomes from ExAC, and variants in start or stop codons. In total, 68,258,623 unlabeled missense variants were generated. This was filtered to correct for regions of poor sequencing coverage, and regions where there was not a one-to-one alignment between human and primate genomes when selecting matched unlabeled variants for the primate variants.

We obtained a consensus prediction by training eight models that use the same set of labeled benign variants and eight randomly sampled sets of unlabeled variants, and taking the average of their predictions. We also set aside two randomly sampled sets of 10,000 primate variants for validation and testing, which we withheld from training (Supplementary Data File 3). For each of these sets, we sampled 10,000 unlabeled variants that were matched by trinucleotide context, which we used to normalize the threshold of each classifier when comparing between different classification algorithms (Supplementary Data File 4). In other implementations, fewer or additional models can be used in the ensemble, ranging from 2 to 500.

We assessed the classification accuracy of two versions of the deep learning network, one trained with common human variants only, and one trained with the full benign labeled dataset including both common human variants and primate variants.

Architecture of the Deep Learning Network

For each variant, the pathogenicity prediction network takes as input the 51-length amino acid sequence centered at the variant of interest, and the outputs of the secondary structure and solvent accessibility networks (FIG. 16 and FIG. 17) with the missense variant substituted in at the central position. Three 51-length position frequency matrices are generated from multiple sequence alignments of 99 vertebrates, including one for 11 primates, one for 50 mammals excluding primates, and one for 38 vertebrates excluding primates and mammals.

The secondary structure deep learning network predicts a three-state secondary structure at each amino acid position: alpha helix (H), beta sheet (B), and coils (C). The solvent accessibility network predicts a three-state solvent accessibility at each amino acid position: buried (B), intermediate (I), and exposed (E). Both networks only take the flanking amino acid sequence as their inputs, and were trained using labels from known non-redundant crystal structures in the Protein DataBank. For the input to the pretrained three-state secondary structure and three-state solvent accessibility networks, we used a single length position frequency matrix generated from the multiple sequence alignments for all 99 vertebrates, also with length 51 and depth 20. After pre-training the networks on known crystal structures from the Protein DataBank, the final two layers for the secondary structure and solvent models were removed and the output of the network was directly connected to the input of the pathogenicity model. The best testing accuracy achieved for the three-state secondary structure prediction model was 79.86%. There was no substantial difference when comparing the predictions of the neural network when using DSSP-annotated (Define Secondary Structure of Proteins) structure labels for the approximately ~4,000 human proteins that had crystal structures versus using predicted structure labels only.

Both our deep learning network for pathogenicity prediction (PrimateAI) and deep learning networks for predicting secondary structure and solvent accessibility adopted the architecture of residual blocks. The detailed architecture for PrimateAI is described in (FIG. 17) and (FIGS. 18A, 18B, and 18C). The detailed architecture for the networks for predicting secondary structure and solvent accessibility is described in FIG. 20 and (FIGS. 21A and 21B) and (FIGS. 22A and 22B).

FIG. 16 shows an example architecture of a deep residual network for pathogenicity prediction, referred to herein as "PrimateAI". In FIG. 16, 1D refers to 1-dimensional convolutional layer. Predicted pathogenicity is on a scale from 0 (benign) to 1 (pathogenic). The network takes as input the human amino acid (AA) reference and alternate sequence (51 AAs) centered at the variant, the position weight matrix (PWM) conservation profiles calculated from 99 vertebrate species, and the outputs of secondary structure and solvent accessibility prediction deep learning networks, which predict three-state protein secondary structure (helix—H, beta sheet—B, and coil—C) and three-state solvent accessibility (buried—B, intermediate—I, and exposed—E).

FIG. 17 depicts a schematic illustration of PrimateAI, the deep learning network architecture for pathogenicity classification. The inputs to the model include 51 amino acids (AA) of flanking sequence for both the reference sequence and the sequence with the variant substituted in, conservation represented by three 51-AA-length position-weighted matrices from primate, mammal, and vertebrate alignments, and the outputs of pre-trained secondary structure network and solvent accessibility network (also 51 AA in length).

FIGS. 18A, 18B, and 18C show example model architecture details of the pathogenicity prediction deep learning model PrimateAI. The shape specifies the shape of the output tensor at each layer of the model and the activation is the activation given to the neurons of the layer. Inputs to the model are the position-specific frequency matrices (51 AA length, 20 depth) for the flanking amino acid sequence around the variant, the one-hot encoded human reference and alternate sequences (51 AA length, 20 depth), and the output from the secondary structure and solvent accessibility models (51 AA length, 40 depth).

The illustrated example uses 1D convolutions. In other implementations, the model can use different types of convolutions such as 2D convolutions, 3D convolutions, dilated or atrous convolutions, transposed convolutions, separable convolutions, and depthwise separable convolutions. Some layers also use ReLU activation function which greatly accelerates the convergence of stochastic gradient descent compared to saturating nonlinearities such as sigmoid or hyperbolic tangent. Other examples of activation functions that can be used by the technology disclosed include parametric ReLU, leaky ReLU, and exponential linear unit (ELU).

Some layers also use batch normalization (Ioffe and Szegedy 2015). Regarding batch normalization, distribution of each layer in a convolution neural network (CNN) changes during training and it varies from one layer to another. This reduces the convergence speed of the optimization algorithm. Batch normalization is a technique to overcome this problem. Denoting the input of a batch normalization layer with x and its output using z, batch normalization applies the following transformation on x:

$$z = \frac{x - \mu}{\sqrt{\sigma^2 + \varepsilon}} \gamma + \beta$$

Batch normalization applies mean-variance normalization on the input x using $\mu$ and $\sigma$ and linearly scales and shifts it using $\gamma$ and $\beta$. The normalization parameters $\mu$ and $\sigma$ are computed for the current layer over the training set using a method called exponential moving average. In other words, they are not trainable parameters. In contrast, $\gamma$ and $\beta$ are trainable parameters. The values for $\mu$ and $\sigma$ calculated during training are used in forward pass during inference.

FIGS. 19 and 20 illustrate the deep learning network architecture used for predicting secondary structure and solvent accessibility of proteins. The input to the model is a position-weighted matrix using conservation generated by the RaptorX software (for training on Protein Data Bank sequences) or the 99-vertebrate alignments (for training and inference on human protein sequences). The output of the second to last layer, which is 51 AAs in length, becomes the input for the deep learning network for pathogenicity classification.

FIGS. 21A and 21B show example model architecture details for the 3-state secondary structure prediction deep learning (DL) model. The shape specifies the shape of the output tensor at each layer of the model and the activation is the activation given to the neurons of the layer. Inputs to the model were the position-specific frequency matrices (51 AA length, 20 depth) for the flanking amino acid sequence around the variant.

FIGS. 22A and 22B show example model architecture details for the 3-state solvent accessibility prediction deep learning model. The shape specifies the shape of the output tensor at each layer of the model and the activation is the activation given to the neurons of the layer. Inputs to the model were the position-specific frequency matrices (51 AA length, 20 depth) for the flanking amino acid sequence around the variant.

Figures 34D, 34E:
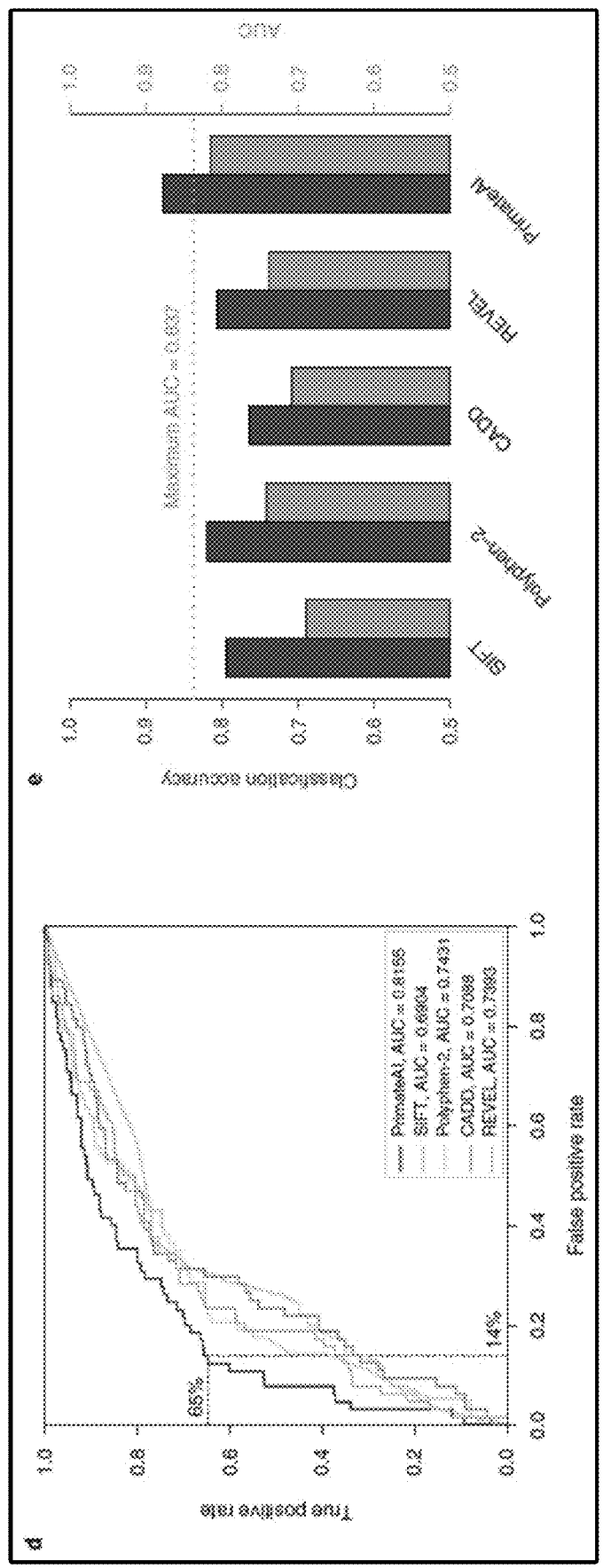
FIG. 34D depicts comparison of various classifiers, shown on a receiver operator characteristic curve, with area under curve (AUC) indicated for each classifier.
FIG. 34E illustrates classification accuracy and area under curve (AUC) for each classifier.

FIG. 34D depicts comparison of various classifiers, shown on a receiver operator characteristic curve, with AUC indicated for each classifier.

FIG. 34E illustrates classification accuracy and AUC for each classifier. The classification accuracy shown is the average of the true positive and true negative error rates, using the threshold where the classifier would predict the same number of pathogenic and benign variants as expected based on the enrichment. To take into account the fact that 33% of the DDD de novo missense variants represent background, the maximum achievable AUC for a perfect classifier is indicated with a dotted line.

Figure 35:
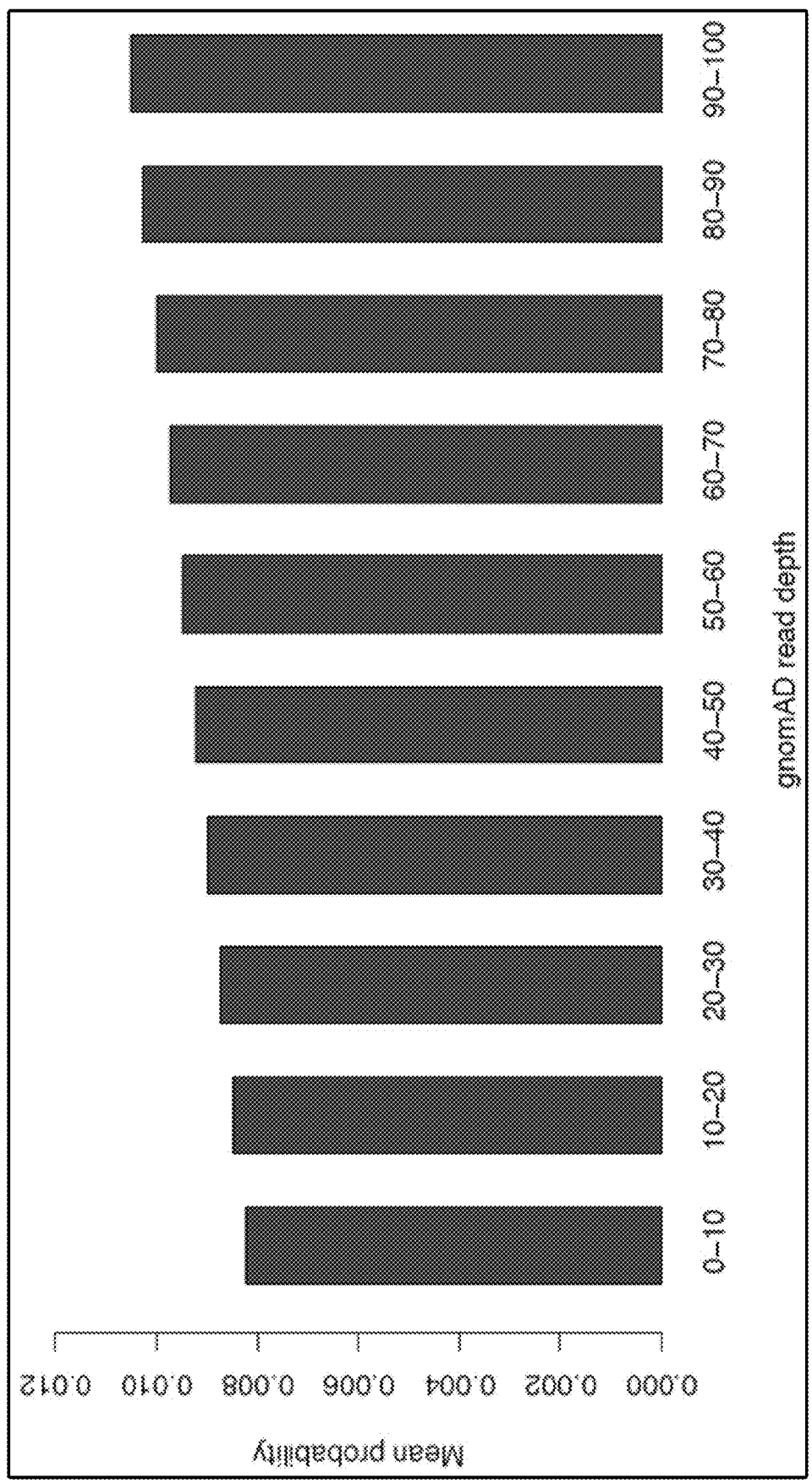
FIG. 35 illustrates correcting for the effect of sequencing coverage on the ascertainment of common primate variants.

FIG. 35 illustrates correcting for the effect of sequencing coverage on the ascertainment of common primate variants. The probability of observing a given variant in a nonhuman primate species is inversely correlated with the sequencing depth at that position in the ExAC/gnomAD exome dataset. In contrast, the lower gnomAD read depth did not affect the probability of observing a common human variant at that position (>0.1% allele frequency) because the large number of human exomes sequenced makes ascertainment of common variation almost guaranteed. When picking matched variants for each of the primate variants for training the network, the probability of picking a variant was adjusted for the effects of sequencing depth, in addition to matching for trinucleotide context to control for mutational rate and gene conversion.

Figure 36A:
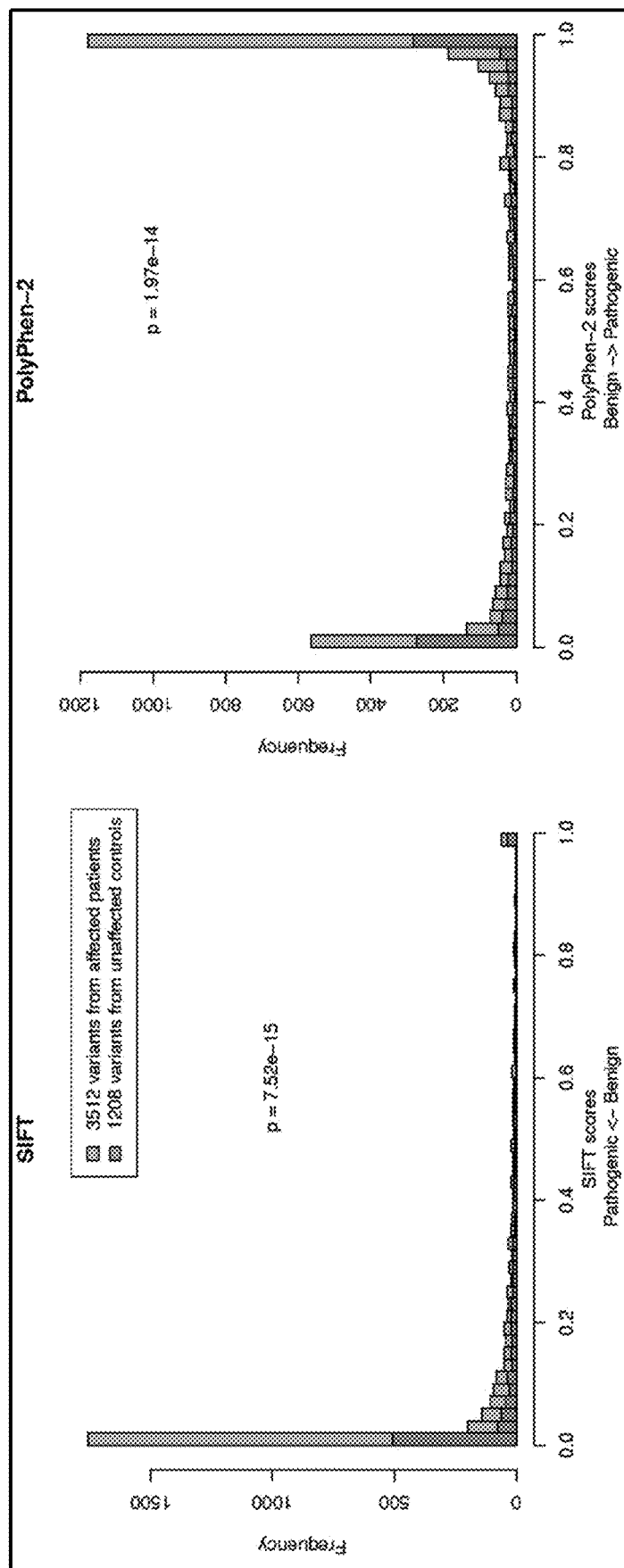
FIGS. 36A and 36B illustrate distribution of the prediction scores of four classifiers.
Figure 36B:
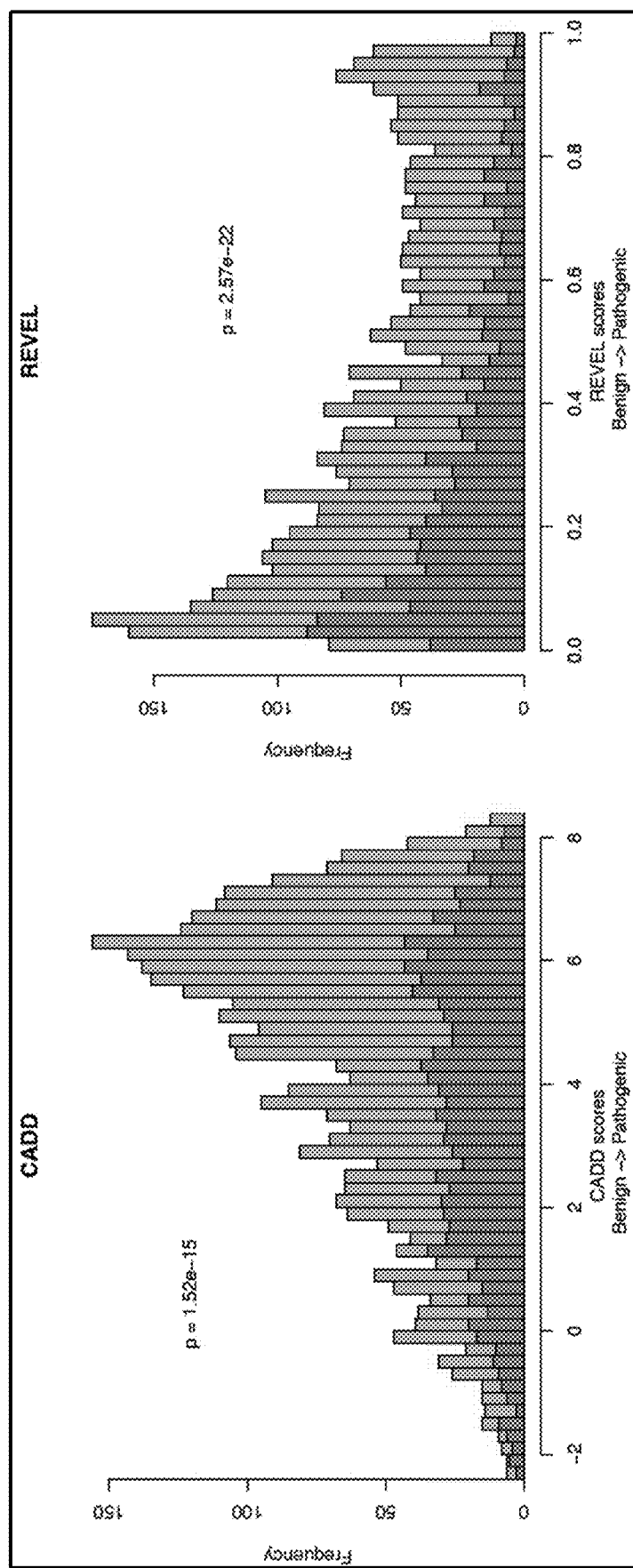

FIGS. 36A and 36B illustrate distribution of the prediction scores of four classifiers. Histograms of the prediction scores of four classifiers, including SIFT, PolyPhen-2, CADD, and REVEL, for de novo missense variants occurring in DDD cases versus unaffected controls, with corresponding Wilcoxon rank-sum P-values.

Figures 37A, 37B:
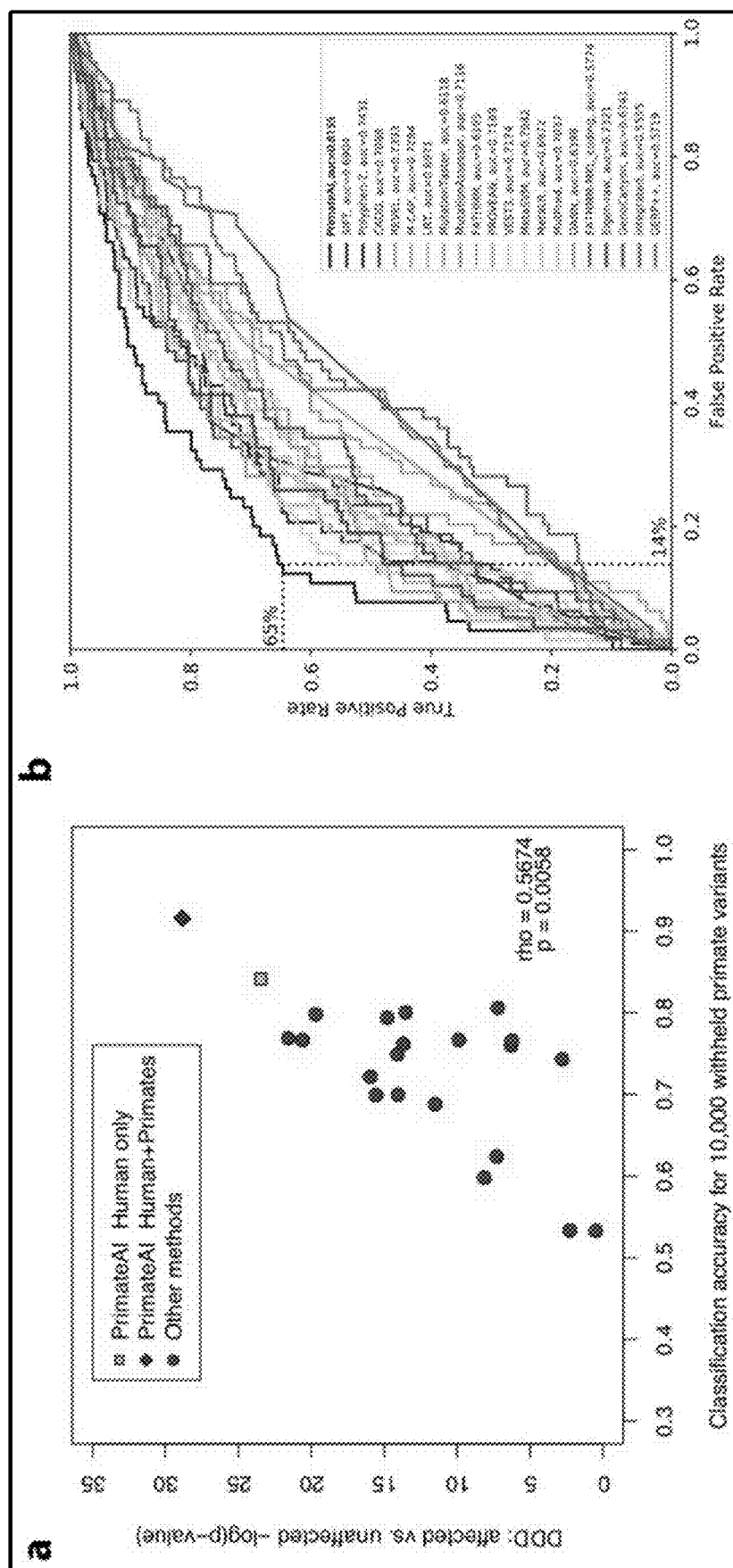
FIGS. 37A, 37B, and 37C compare the accuracy of the PrimateAI network and other classifiers at separating pathogenic and benign variants in 605 disease-associated genes.
Figure 37C:
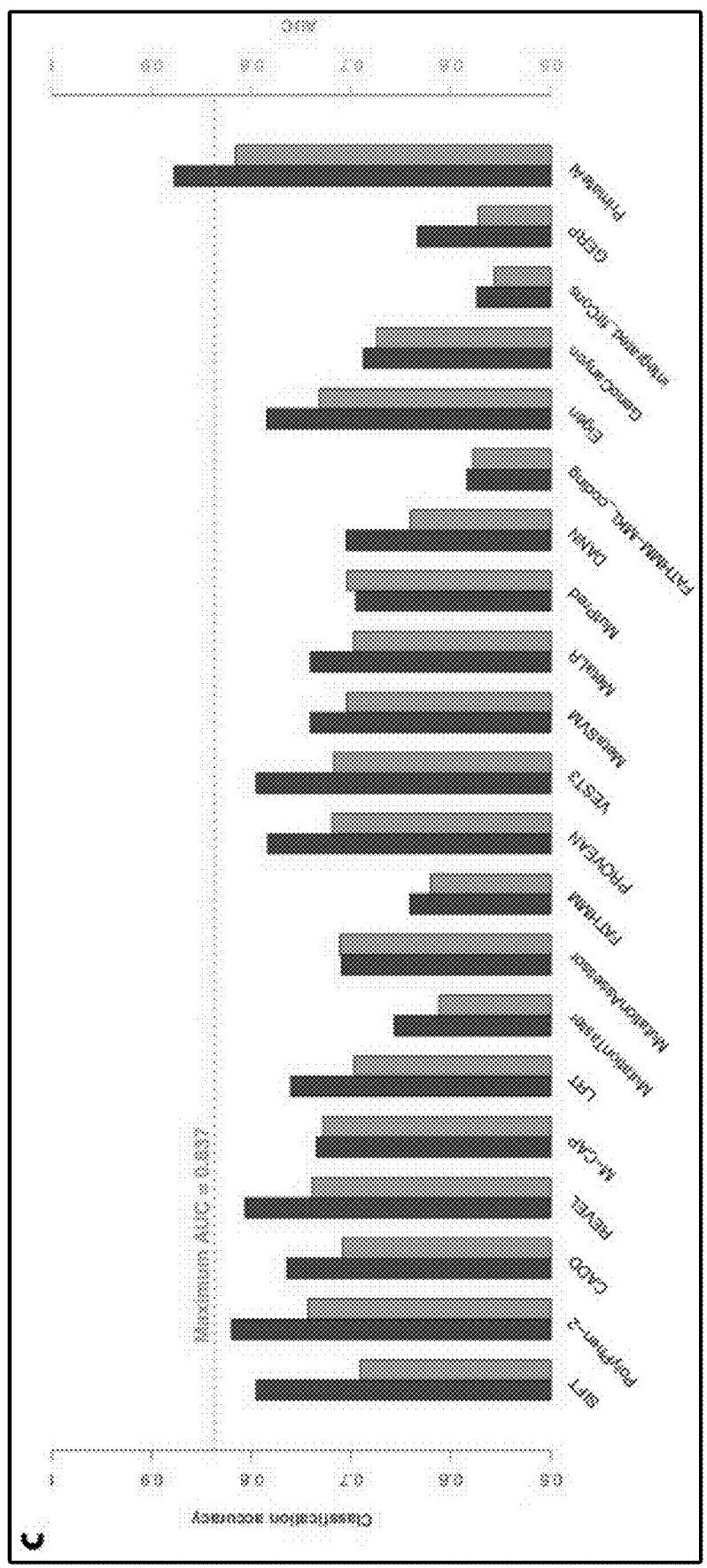

FIGS. 37A, 37B, and 37C compare the accuracy of the PrimateAI network and other classifiers at separating pathogenic and benign variants in 605 disease-associated genes. The scatterplot in FIG. 37A shows the performance of each of the classifiers on DDD cases versus controls (y axis) and benign prediction accuracy on the withheld primate dataset (x axis). FIG. 37B compares different classifiers at separating de novo missense variants in cases versus controls within the 605 genes, shown on a receiver operator characteristic (ROC) curve, with area under the curve (AUC) indicated for each classifier. FIG. 37C shows classification accuracy and AUC for the PrimateAI network and the 20 classifiers listed above. The classification accuracy shown is the average of the true positive and true negative rates, using the threshold where the classifier would predict the same number of pathogenic and benign variants as expected based on the enrichment. The maximum achievable AUC for a perfect classifier is indicated with a dotted line, assuming that de novo missense variants in DDD cases are 67% pathogenic variants and 33% benign, and de novo missense variants in controls are 100% benign.

Figure 31:
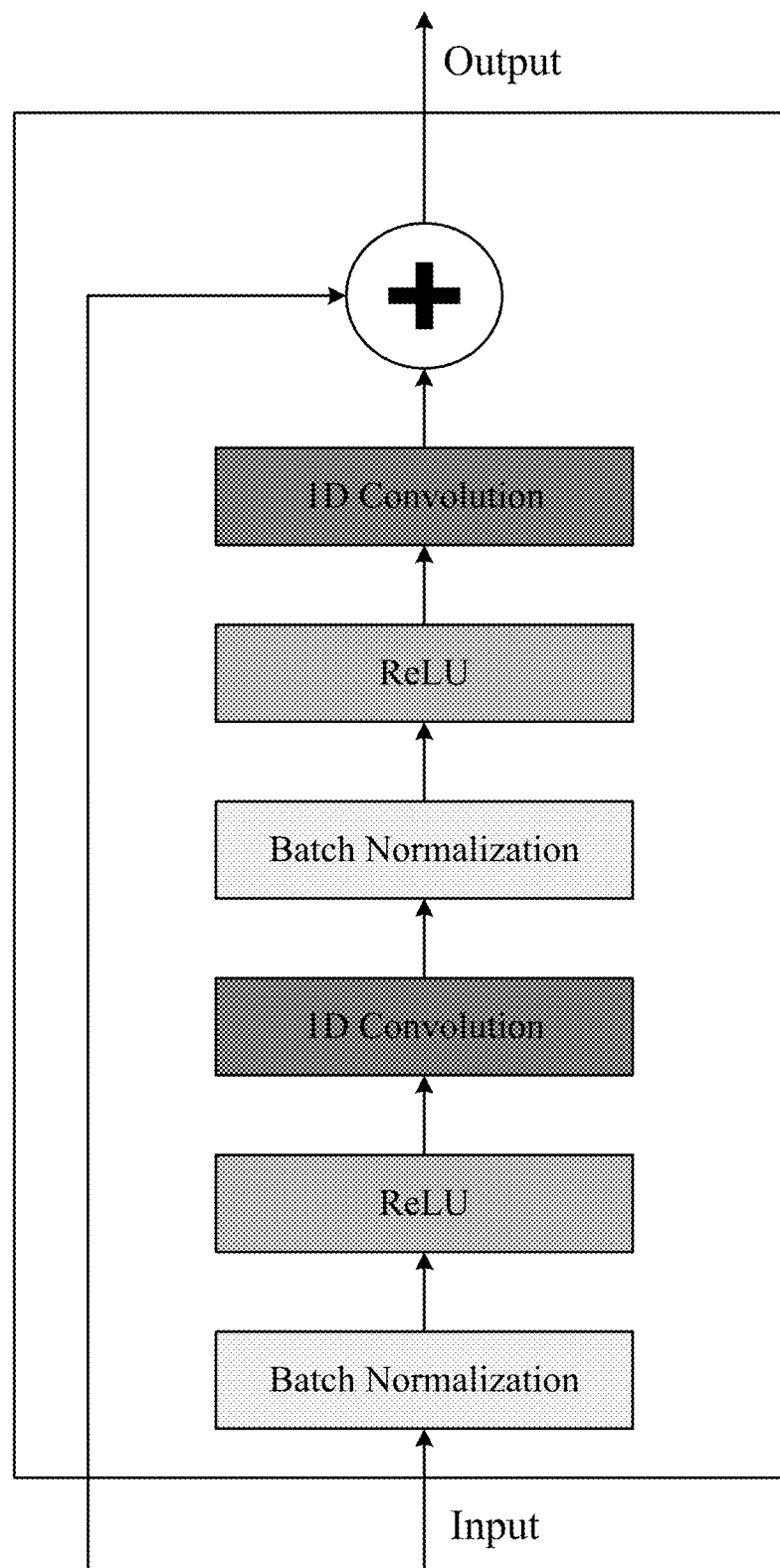
FIG. 31 illustrates a residual block.
Figure 32:
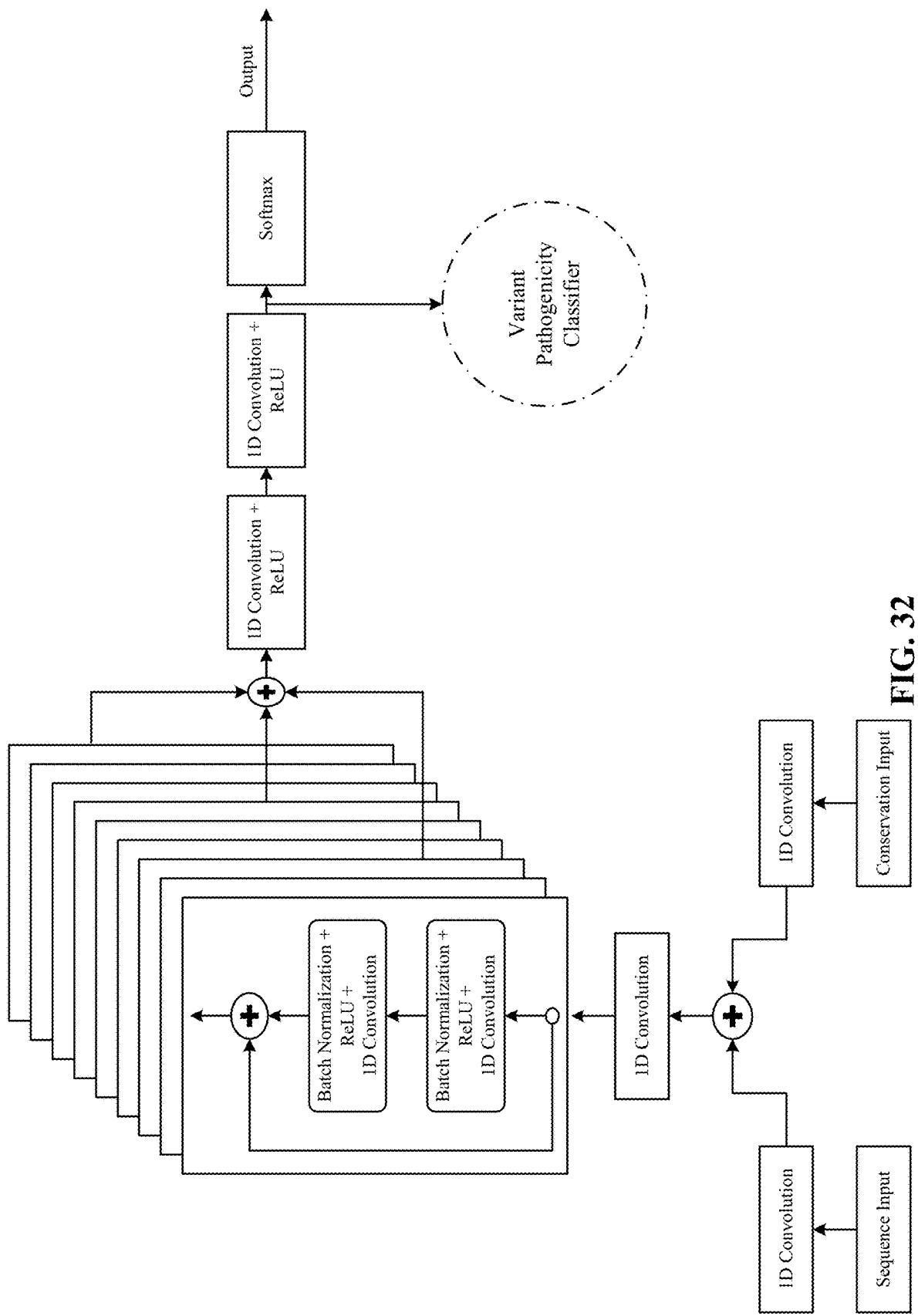
FIG. 32 depicts a neural network architecture of the secondary structure and solvent accessibility subnetworks.
Figure 38A:
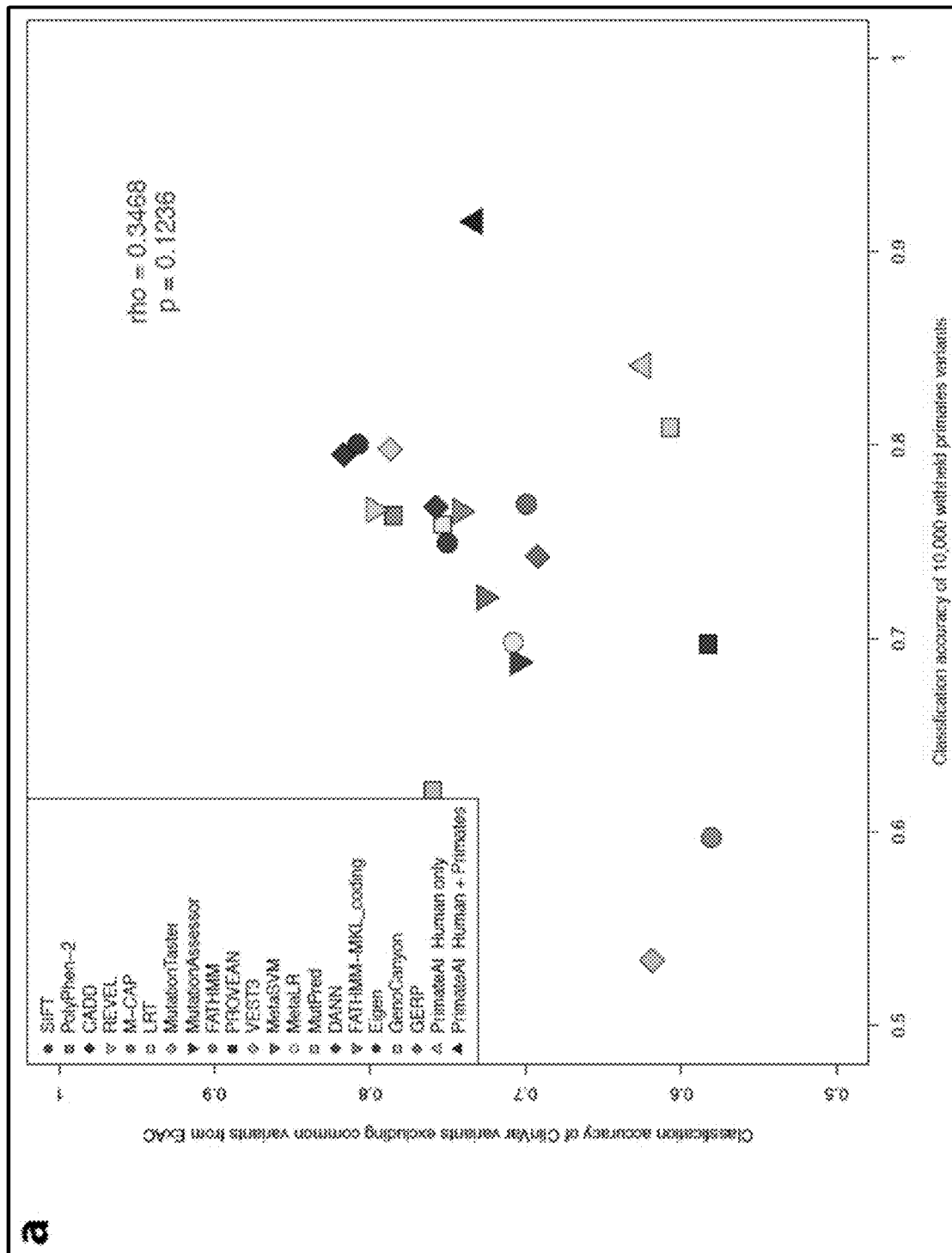
FIGS. 38A and 38B illustrate correlation between classifier performance on human expert-curated ClinVar variants and performance on empirical datasets.
Figure 38B:
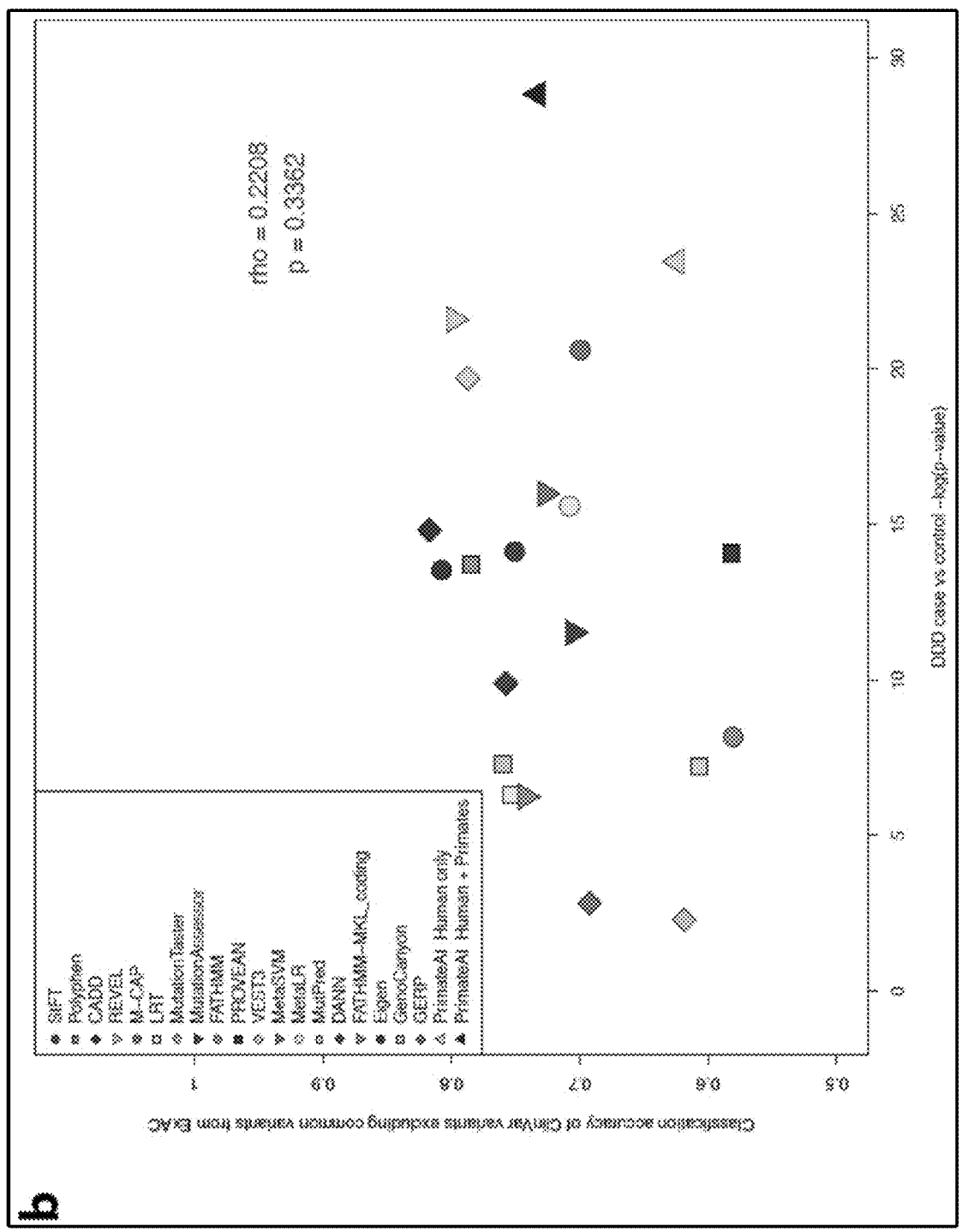

FIGS. 38A and 38B illustrate correlation between classifier performance on human expert-curated ClinVar variants and performance on empirical datasets. The scatterplot in FIG. 31A shows the classification accuracy (y axis) on ClinVar variants on the 10,000 withheld primate variants (x axis) for each of the 20 other classifiers and the PrimateAI network trained with human-only or human+primates data. Shown are the Spearman correlation coefficient rho and associated P value. To limit the evaluation to data that were not used for training the classifiers, we only used ClinVar variants that were added between January 2017 and November 2017, and excluded common human variants from ExAC/gnomAD (>0.1% allele frequency). The ClinVar classification accuracy shown is the average of the true positive and true negative rates, using the threshold where the classifier would predict the same number of pathogenic and benign variants as observed in the ClinVar dataset.

The scatterplot in FIG. 38B shows the classification accuracy (y axis) on ClinVar variants the DDD cases versus controls full dataset (x axis) for each of the 20 other classifiers and the PrimateAI network trained with human-only or human+primates data.

FIG. 39 shows performance of the 3-state secondary structure and 3-state solvent accessibility prediction models on annotated samples from the Protein DataBank, using 6,367 unrelated protein sequences for training, 400 for validation, and 500 for testing. Only proteins with <25% sequence similarity were selected from the Protein DataBank. We report the accuracy of the deep learning networks as a performance metric, as the three classes are not grossly unbalanced for either secondary structure or solvent accessibility.

FIG. 40 shows performance comparison of deep learning network using annotated secondary structure labels of human proteins from DSSP database when available with deep learning network using predicted secondary structure labels.

FIG. 41 shows the accuracy values on the 10,000 withheld primate variants and the p-values for de novo variants in DDD cases vs controls for each of the 20 classifiers we evaluated. The PrimateAI model with Human data only is our deep learning network that was trained using a labeled benign training dataset comprising only of common human variants (83.5K variants with >0.1% in the population), while PrimateAI model with Human+Primates data is our deep learning network trained on the full set of 385K labeled benign variants, comprising both common human variants and primate variants.

FIG. 42 shows comparison of the performance of different classifiers on de novo variants in the DDD case vs control dataset, restricted to 605 disease-associated genes. To normalize between the different methods, for each classifier we identified the threshold where the classifier would predict the same number of pathogenic and benign variants as expected based on the enrichment in DDD and the control set. Classification accuracy shown is the average of the true positive and true negative error rates at this threshold.

Generation of Unlabeled Variants to Complement the Benign Training Dataset

All possible missense variants were generated from each base position of canonical coding regions by substituting the nucleotide at the position with the other three nucleotides. We excluded variants that were observed in the 123,136 exomes from ExAC/gnomAD, and variants in start or stop codons. In total, 68,258,623 unlabeled variants were generated. We assigned each of the unlabeled variants to one of the 96 different tri-nucleotide context categories. We trained the deep learning network using a semi-supervised approach, by sampling variants from this unlabeled dataset that match the variants in the benign dataset by tri-nucleotide context, and training the classifier to discriminate between benign and unlabeled training examples.

Additional Filtering of Unlabeled Variants

By presenting examples of benign and unlabeled variants along with the flanking amino acid sequence, the deep learning network learns regions of proteins that are highly intolerant of mutations. However, the absence of common variants within a region of the protein sequence may be due to strong purifying selection, or it may be due to technical artifacts that prevent variants from being called in the region. To correct for the latter, we removed variants from both the benign and unlabeled datasets from regions where the ExAC/gnomAD dataset had mean coverage <1. Similarly, when matching unlabeled variants to primate variants in the benign dataset during training, we excluded unlabeled variants from regions where that primate did not have orthologous alignable sequence with human in the multiple sequence alignment.

Withheld Primate Variants for Validation and Testing, and De Novo Variants from Affected and Unaffected Individuals For validating and testing of the deep learning network, we randomly sampled two sets of 10,000 primate variants for validation and testing, which we withheld from training. The rest of the primate variants, along with the common human variants (>0.1% allele frequency), were used as the benign dataset for training the deep learning network. In addition, we also sampled two sets of 10,000 unlabeled variants that were matched to the withheld primate variants for the validation set and the test set.

We used the 10,000 withheld primate variants in the validation set and the matched 10,000 unlabeled variants to monitor the performance of the deep learning network during the course of training, by measuring the ability of the network to discriminate between variants in the two sets. This enabled us to determine a stopping point for training and avoid over-fitting, once the performance of the network had saturated.

We used the 10,000 withheld primate variants in the test dataset to benchmark the deep learning network as well as the other 20 classifiers. Because the different classifiers had widely varying score distributions, we used these unlabeled variants to identify the 50th-percentile threshold for each classifier. We benchmarked each classifier on the fraction of variants in the 10,000 withheld primate variant test set that were classified as benign at the 50th-percentile threshold for that classifier, to ensure fair comparison between the methods.

Prediction of Secondary Structure and Solvent Accessibility

The deep learning network for pathogenicity prediction contains 36 total convolutional layers, including 19 convolutional layers for the secondary structure and solvent accessibility prediction networks, and 17 for the main pathogenicity prediction network which takes as input the results of the secondary structure and solvent accessibility networks. Because the crystal structures of most human proteins are unknown, we trained two models to enable the network to learn protein structure from primary sequence. Both models used the same network architecture and inputs shown in FIG. 6. The inputs to the secondary structure and solvent accessibility networks is a 51 length×20 amino acid position frequency matrix encoding conservation information from the multiple sequence alignment of human with 99 other vertebrates.

The secondary structure network is trained to predict 3-state secondary structure: alpha helix (H), beta sheet (B), and coils (C). The solvent accessibility network is trained to predict 3-state solvent accessibility: buried (B), intermediate (I), and exposed (E). Both networks only take primary sequence as their inputs, and were trained using labels from known crystal structures in the Protein DataBank. The models predict one state for each amino acid residue.

Data Preparation for Prediction of Secondary Structure and Solvent Accessibility We used unrelated crystal structures from the Protein Databank for training the models. Amino acid sequences with more than 25% sequence similarity were removed. In total, 6,367 protein sequences were used for training, 400 for validation, and 500 for testing. The data used for training, including the amino acid sequence and the secondary structure and solvent accessibility labels is available from the RaptorX website: http://raptorx.uchicago.edu/download/.

Most solved crystal structures are of non-human proteins, hence for pre-training the secondary structure and solvent models, we used the RaptorX suite (based on PSI-BLAST) to obtain related sequences, since human-based multiple sequence alignments were generally not available. We generated multiple sequence alignments for the proteins using the CNFsearch1.66_release tool from RaptorX, and counted the amino acids at each position from the 99 closest alignments to form the position frequency matrix. For example, the specific commands using RaptorX to retrieve the multiple sequence alignment for the 1u71A.fasta protein were as follows:

% ./buildFeature -i 1u71A.fasta -c 10-o ./TGT/1u71A.tgt
% ./CNFsearch -a 30-q 1u71A For each amino acid position in the dataset, we took a window from the position frequency matrix corresponding to the flanking 51 amino acids, and used this to predict the label for either secondary structure or solvent accessibility for the amino acid at the center of the 51-length amino acid sequence. The labels for secondary structure and relative solvent accessibility were directly obtained from the known 3D crystal structure of the protein using the DSSP software and did not require prediction from primary sequence. To incorporate the secondary structure and solvent accessibility networks as part of the pathogenicity prediction network, we computed position frequency matrices from the human-based 99 vertebrate multiple sequence alignments. Although the conservation matrices generated from these two methods are generally similar, we enabled backpropagation through the secondary structure and solvent accessibility models during training for pathogenicity prediction to allow fine-tuning of the parameter weights.

Model Architecture and Training

We trained two separate deep convolutional neural network models to predict secondary structure and relative solvent accessibility of proteins. The two models have identical architecture and input data, but differ on the prediction states. We conducted detailed hyperparameter search to optimize the models for best performance. Both our deep learning network for pathogenicity prediction and deep learning networks for predicting secondary structure and solvent accessibility adopted the architecture of residual blocks, which has become widely adopted due to its success in image classification. The residual blocks comprise repeating units of convolution, interspersed with skip connections that allow information from earlier layers to skip over residual blocks. In each residual block, the input layer is first batch normalized, followed by an activation layer using rectified linear units (ReLU). The activation is then passed through a 1D convolution layer. This intermediate output from the 1D convolution layer is again batch normalized and ReLU activated, followed by another 1D convolution layer. At the end of the second 1D convolution, we summed its output with the original input into the residual block, which acts as a skip connection by allowing the original input information to bypass the residual block. In such an architecture, termed a deep residual learning network by its authors, the input is preserved in its original state and the residual connections are kept free of nonlinear activations from the model, allowing effective training of deeper networks. The detailed architecture is provided in FIG. 6 and (FIGS. 7A and 7B) and (FIGS. 8A and 8B).

Following the residual blocks, the softmax layer computes probabilities of the three states for each amino acid, among which the largest softmax probability determines the state of the amino acid. The model is trained with accumulated categorical cross entropy loss function for the whole protein sequence using the ADAM optimizer. Once the networks had been pretrained on secondary structure and solvent accessibility, instead of directly taking the output of the networks as inputs for the pathogenicity prediction network, we took the layer before the softmax layer, so that more information would pass through to the pathogenicity prediction network.

The best testing accuracy achieved for the 3-state secondary structure prediction model is 79.86%, similar to the state-of-the-art accuracy predicted by DeepCNF mode130. The best testing accuracy for the 3-state solvent accessibility prediction model is 60.31%, similar to the current best accuracy predicted by RaptorX on the similar training dataset. We also compared the predictions of the neural network when using DSSP-annotated structure labels for the approximately 4000 human proteins that had crystal structures, versus using the standard PrimateAI model which uses predicted structure labels only. We did not obtain further improvement in pathogenicity prediction accuracy when using the DSSP-annotated labels (Supplemental Table 15).

Input Features for Deep Learning Models for Pathogenicity Prediction

The training dataset for the pathogenicity prediction network contains 385,236 labeled benign variants and 68,258,623 unlabeled variants after filtering. For each variant, we generated the following input features. The first input feature of each variant is its 51-length flanking amino acid sequence, i.e., 25 amino acids to each side of the variant obtained from the reference sequence of hg19, to provide the deep learning models the sequence context of the variant. In total, this flanking reference sequence is 51 amino acids in length. Through empirical observation we found that amino acid representation of the protein sequence was more effective than representing the protein coding sequence using nucleotides.

The second feature is the 51-length flanking human amino acid sequence with the alternative amino acid substituted at the central position by the variant. The alternative flanking sequence is the same as the reference flanking sequence in the first feature, except that the middle position of the sequence contains the alternative amino acid, instead of the reference amino acid. Both reference and alternative human amino acid sequences were converted to one-hot encoded vectors of length 51×20, where each amino acid is represented by a vector of 19 amino acids with value 0, and a single amino acid with value 1.

Three position frequency matrices (PFMs) are generated from multiple sequence alignments of 99 vertebrates for the variant, including one for 11 primates, one for 50 mammals excluding primates, and one for 38 vertebrates excluding primates and mammals. Each PFM has dimensions L×20, where L is the length of flanking sequences around the variant (in our case, L represents 51 amino acids).

For the input to the pre-trained 3-state secondary structure and 3-state solvent accessibility networks, we used a single PFM matrix generated from the multiple sequence alignments for all 99 vertebrates, also with length 51 and depth 20. After pre-training the networks on known crystal structures from the Protein DataBank, the final two layers for the secondary structure and solvent models were removed (the global maxpool layer and the output layer), and the 51×40 shape of the previous layer's output was used as input for the pathogenicity prediction network. We allowed backpropagation through the structural layers of the network to fine-tune parameters.

Semi-Supervised Learning

Because semi-supervised learning algorithms use both labeled and unlabeled instances in the training process, they can produce classifiers that achieve better performance than completely supervised learning algorithms that have only a small amount of labeled data available for training. The principle behind semi-supervised learning is that intrinsic knowledge within unlabeled data can be leveraged in order to strengthen the prediction capability of a supervised model that only uses labeled instances, thereby providing a potential advantage for semi-supervised learning. Model parameters learned by a supervised classifier from a small amount of labeled data may be steered towards a more realistic distribution (which more closely resembles the distribution of the test data) by the unlabeled data.

Another challenge that is prevalent in bioinformatics is the data imbalance problem. The data imbalance phenomenon arises when one of the classes to be predicted is underrepresented in the data because instances belonging to that class are rare (noteworthy cases) or hard to obtain. Ironically, minority classes are typically the most important to learn, because they may be associated with special cases.

An algorithmic approach to handle imbalanced data distributions is based on ensembles of classifiers. Limited amounts of labeled data naturally lead to weaker classifiers, but ensembles of weak classifiers tend to surpass the performance of any single constituent classifier. Moreover, ensembles typically improve the prediction accuracy obtained from a single classifier by a factor that validates the effort and cost associated with learning multiple models. Intuitively, aggregating several classifiers leads to better overfitting control, since averaging the high variability of individual classifiers also averages the classifiers' overfitting.

We pursued a semi-supervised learning strategy because of the lack of adequately sized datasets of confidently labeled pathogenic variants. Although the ClinVar database has over 300,000 entries, after removing variants of uncertain significance, there were only ~42,000 missense variants remaining with non-conflicting interpretations of pathogenicity.

Systematic reviews have also found that these entries often have insufficient clinical evidence to support their annotated pathogenicity. Moreover, most of the variants in human curated databases tend to be within a very small set of genes, making them mismatched for variants in benign training datasets, which are ascertained genome-wide using human common variants or chimpanzee-human fixed substitutions. Given how differently the datasets were ascertained, training a supervised learning model with human-curated variants as the pathogenic set and genome-wide common variants as the benign set is likely to introduce significant biases.

We trained the deep learning network to discriminate between a set of labeled benign variants and an unlabeled set of variants that were carefully matched to remove biases. According to one implementation, the set of 385,236 labeled benign variants comprised human common variants (>0.1% allele frequency) from the ExAC/gnomAD database and variants from six species of non-human primates.

We sampled a set of unlabeled variants, requiring matching with the benign variants on trinucleotide context (to control for mutational rate, genetic drift, and gene conversion), and adjusting for the impact of alignability and sequence coverage on variant ascertainment. Because the number of unlabeled variants greatly exceeds the labeled benign variants, we obtained a consensus prediction by training eight models that use the same set of labeled benign variants and eight randomly sampled sets of unlabeled variants and taking the average of their predictions.

The motivation of choosing semi-supervised learning is that human-curated variant databases are unreliable and noisy, and in particular, the lack of reliable pathogenic variants. We obtained a set of reliable benign variants from human common variants from gnomAD and primate variants. For pathogenic variants, we adopted an iterative balanced sampling approach to initially sampling pathogenic variants from a set of unknown variants (VUS variants without annotated clinical significance).

To reduce the sampling bias, we trained an ensemble of eight models that use the same set of benign training variants and eight different sets of pathogenic variants. Initially, we randomly sampled unknown variants to represent pathogenic variants. Next, iteratively, the ensemble of models are used to score a set of unknown variants that were not involved in the prior training cycle. The top scored pathogenic variants are then obtained to replace 5% of random unknown variants in the prior cycle. Note that we retained 25% more top scored pathogenic variants than needed, so that we can sample eight different sets of scored pathogenic variants to replace unknown variants which increases randomness for the eight models. Then the new pathogenic training set is formed and a new cycle of training is executed. This process is repeated till initial randomly-sampled unknown variants are all replaced by highly confident pathogenic variants predicted by the ensemble models. FIG. 42 is an illustration of the iterative balanced sampling process.

Balancing the Benign and Unknown Training Sets

The sampling scheme of unknown variants that match benign variants is useful in reducing the bias of our model training. When the unknown variants are sampled randomly, deep learning models often extract biased information and present trivial solutions. For example, if an amino acid substitution K→M occurs more frequently in unknown variants than benign variants, the deep learning models tend to always classify K→M substitutions as pathogenic. Thus, it is important to balance the distribution of amino acid substitutions between the two training sets.

Higher mutable classes like CpG transitions have a huge representation bias in the benign common variants. The orthologous variants from other primates also follow the human mutation rates, implying enrichment of the highly mutable classes in the overall benign training set. If the sampling procedure of unknown variants is not well controlled and balanced, deep learning models tend to be more likely to classify CpG transitions as benign, compared to a less represented class such as transversion or non CpG transitions.

To prevent deep learning models from converging to a trivial, non-biological solution, we consider balancing the trinucleotide contexts of benign and unknown variants. The trinucleotide is formed by the base before the variant, the reference base of the variant, and the base after the variant. And the reference base of the variant can be changed into the other three nucleotides. In total, there are 64×3 trinucleotide contexts.

Iterative Balanced Sampling

Cycle 1

We sampled the unknown variants to match the exact number of benign variants for each trinucleotide context. In other words, at the first cycle, we mirrored the benign and pathogenic training sets in terms of trinucleotide contexts of variants. The intuition behind such a sampling methodology is that there are equal representation of variants with identical mutation rates between the benign and unknown sets. This prevents the model from converging to a trivial solution based on mutation rates.

Cycle 2 to Cycle 20

For cycle 2, we applied the trained model from cycle 1 to score a set of unknown variants that are not involved in cycle 1, and replaced 5% of the unknown variants with the top predicted pathogenic variants. This set is purely generated by the model and we applied no balancing for trinucleotide contexts in this set. The rest of 95% of the unknown variants required for training are sampled to be 95% of the counts of each trinucleotide context in benign variants.

The intuition is that since cycle 1 uses completely matched training sets, the top predicted pathogenic variants are generated without any mutation rate bias. Hence, There is no need to account for any bias in this set. The rest of 95% of the data is still controlled for the trinucleotide context mutation rate to prevent the model from converging to a trivial solution.

For each cycle, the percentage of the replaced unknown variants increases by 5%. For cycle 3, we replaced 5% of the unknown variants with the top predicted pathogenic variants from the model of cycle 3. Accumulatively, the fraction of pathogenic variants increases to 10% and that of the trinucleotide-context-mirrored unknown variants is reduced to 90%. The sampling process is similar for the rest cycles.

Cycle 21

For cycle 21, the last cycle, the entire pathogenic training set comprise purely of the top pathogenic variants predicted from the deep learning models. Since we have explicitly controlled for the mutation rate bias at every cycle, the pathogenic variants are reliable to use as training data and not affected by the mutation rate bias. Thus, the last cycle of training produces the final deep learning model for pathogenicity prediction.

Matching the Labeled Benign and Unlabeled Training Sets

Balanced sampling of unlabeled variants is crucial for removing biases that are unrelated to the deleteriousness of the variant. In absence of proper control of confounding effects, deep learning can easily pick up on inadvertently introduced biases to discriminate between the classes. Human common variants tend to be enriched with variants from highly mutable classes, such as those on CpG islands. Likewise, primate polymorphisms also follow human mutational rates, implying enrichment of highly mutable variants in the overall benign training set. If the sampling procedure of unlabeled variants is not well controlled and balanced, deep learning networks tend to rely on mutational rate bias to classify variants, thus they are more likely to classify CpG transitions as benign, compared to less represented classes such as transversion or non-CpG transition. We sampled exactly the same number of unlabeled variants as labeled benign variants in each of the 96 trinucleotide contexts (discussed previously).

When matching unlabeled variants for the primate variants in the labeled benign dataset, we disallowed unlabeled variants from being selected from regions of the human genome where that primate species was not aligned in the multiple sequence alignment, since it was not possible to call a variant in that primate species at that position.

Figure 24:
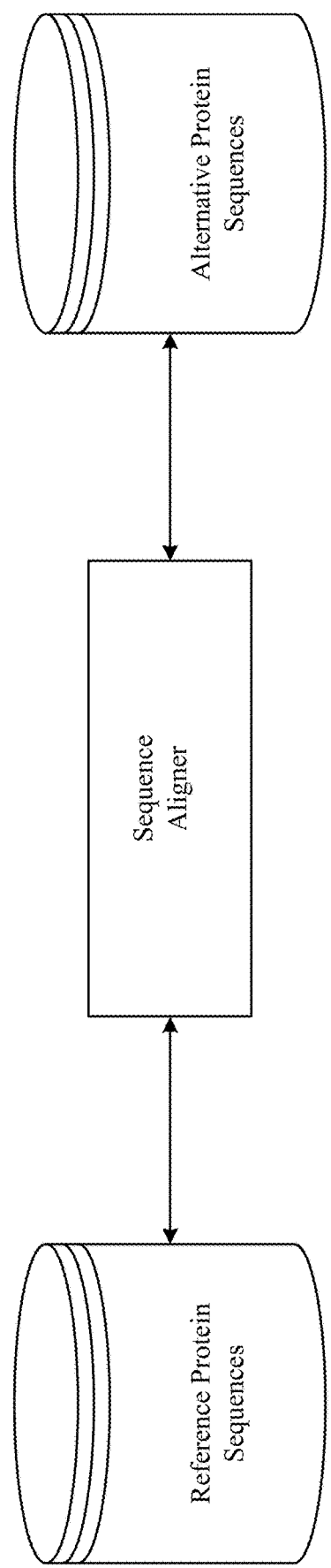
FIG. 24 shows one implementation of aligning reference and alternative protein sequences.

Within each of the 96 trinucleotide contexts, we corrected for sequencing coverage for primate variants. Because of the large number of humans sequenced, common variants in the human population are observed frequently enough that they are well-ascertained even in areas with low sequencing coverage. The same is not true for primate variants, since only a small number of individuals were sequenced. We split the genome into 10 bins based on sequencing coverage in ExAC/gnomAD exomes. For each bin, we measured the fraction of primate variants in the labeled benign dataset versus the unlabeled dataset. We calculated the probability that a primate variant is a member of the labeled benign dataset, based only on sequencing coverage, using linear regression (FIG. 24). When selecting unlabeled variants to match the primate variants in the labeled benign dataset, we weighted the probability of sampling a variant based on the sequencing coverage at that position using the regression coefficients.

Generation of Benign and Unknown Variants

Common Variants in Human Population

Recent studies demonstrated that common variants in human populations are generally benign. gnomAD provides 90,958 nonsynonymous SNPs with minor allele frequency (MAF) >=0.1% within canonical coding regions, according to one implementation. Variants that passed filters are retained. Indels are excluded. Variants that occur in the start or stop codons are removed, as well as protein-truncating variants. Scrutinizing subpopulations, the total number of missense variants with MAF>=0.1% within each subpopulation increases to 245,360, according to one implementation. These variants forms part of the training set of benign variants.

Common Polymorphism in Great Apes

As coding regions are known to be highly conservative, it is straightforward to assume if a polymorphism is segregating in a great ape population at high frequency, it may also have a mild impact on human fitness. Polymorphism data of bonobo, chimp, gorilla, and orangutan from great ape genome projects and other studies were merged with SNPs of rhesus and marmoset from db SNP.

Generation of Unknown Variants

All the possible variants are generated from each base position of canonical coding regions by substituting the nucleotide at the position to the other three nucleotides. New codons are formed leading to potential changes of amino acids at the positions. Synonymous changes are filtered.

Variants observed in gnomAD dataset are removed. Variants that occur in the start or stop codons are removed, as well as variants that form stop codons. For SNPs with multiple gene annotations, the canonical gene annotation is selected to represent the SNP's annotation. In total, 68,258, 623 unknown variants are generated, according to one implementation.

Additional Filtering of Variants

In some regions of human genome, it is known to be difficult to align reads. Inclusion of those regions cause confounding effects on the training and testing datasets. For example, regions under high selective pressure tend to have limited numbers of polymorphisms. Whereas, regions that are hard to sequence also have fewer polymorphisms. To avoid such confounding inputs to our models, we removed variants from genes that were not sequenced by gnomAD.

Generally benign variants are discovered in the well-sequenced regions which tend to be conservative across multiple species. While unknown variants are randomly sampled across genomes, which include some poorly-covered regions. This causes ascertainment bias between the benign and unknown sets. To reduce the bias, we filtered out variants with read depths <10 in gnomAD. We also filtered out all variants which have more than 10% missing data in the flanking sequence alignments across all the mammal species.

Data for Validation and Testing

For validating and testing the pathogenicity models, we randomly sampled from the big pool of benign variants two sets of 10,000 benign variants for validation and testing, respectively, according to one implementation. The rest of benign variants are used for training the deep learning models. These variants are specifically sampled from orthologous primate variants to ensure fair comparison between methods as some methods are trained on human common variants. We also randomly sampled two sets of 10,000 unknown variants for validation and testing, separately, according to one implementation. We ensure that the number of unknown variants within each of the 192 trinucleotide contexts match that of benign variants for validation and testing sets, respectively.

We evaluated the performance of multiple methods in clinical settings using de novo variants of affected children with autism or developmental disability disorder (DDD) and their unaffected siblings. Totally, according to one implementation, there are 3821 missense de novo variants from the cases with DDD and 2736 missense de novo variants from the cases with autism. There are 1231 missense de novo variants for unaffected siblings, according to one implementation.

Deep Learning Network Architecture

The pathogenicity prediction network receives five direct inputs and two indirect inputs via the secondary structure and solvent accessibility networks. The five direct inputs are the 51-length amino acid sequences×20-depth (encoding the 20 different amino acids), and comprise the reference human amino acid sequence without the variant (1a), the alternative human amino acid sequence with the variant substituted in (1b), the PFM from the multiple sequence alignment of primate species (1c), the PFM from the multiple sequence alignment of mammalian species (1d), and the PFM from the multiple sequence alignment of more distant vertebrate species (1e). The secondary structure and solvent accessibility networks each receive as input a PFM from the multiple sequence alignment (1f) and (1g), and provide their outputs as inputs into the main pathogenicity prediction network. The secondary structure and solvent accessibility networks were pre-trained on known protein crystal structures for the Protein DataBank, and allow backpropagation during the pathogenicity model training.

The five direct input channels are passed through an upsampling convolution layer of 40 kernels with linear activations. The human reference amino acid sequence (1a) is merged with the PFMs from primate, mammal, and vertebrate multiple sequence alignments (Merge 1a). Similarly, the human alternative amino acid sequence (1b), is merged with the PFMs from primate, mammal, and vertebrate multiple sequence alignments (Merge 1b). This creates two parallel tracks, one for the reference sequence, and one with the alternate sequence with the variant substituted in.

The merged feature map of both reference channel and the alternative channel (Merge 1a and Merge 1b) are passed through a series of six residual blocks (Layers 2a to 7a, Merge 2a and Layers 2b to 7b, Merge 2b). The output of the residual blocks (Merge 2a and Merge 2b) are concatenated together to form a feature map of size (51,80) (Merge 3a, Merge 3b) which fully mixes the data from the reference and alternative channels. Next, the data has two paths for passing through the network in parallel, either through a series of six residual blocks containing two convolutional layers each, as defined in section 2.1 (Merge 3 to 9, Layers 9 to 46 excluding layer 21,34), or via skip connections, which connect the output of every two residual blocks after passing through a 1D convolution (Layer 21, Layer 37, Layer 47). Finally, the merged activations (Merge 10) are fed to another residual block (layers 48 to 53, Merge 11). The activations from Merge 11 are given to a 1D convolution with filter size 1 and sigmoid activation (Layer 54), then passed through a global max pooling layer that picks a single value representing the network's prediction for variant pathogenicity. A schematic illustration of the model is shown in FIG. 3 and (FIGS. 4A, 4B, and 4C).

Model Overview

We developed semi-supervised deep convolutional neural network (CNN) models to predict pathogenicity of variants. The input features to the models include protein sequences and conservation profiles flanking variants, and depletion of missense variants in specific gene regions. We also predicted the changes caused by variants to secondary structure and solvent accessibility by deep learning models and integrated that into our pathogenicity prediction model. For training the model, we generated benign variants from common variants of human subpopulations and orthologous variants from primates. However, we are still lacking reliable sources for pathogenic variants. We initially trained the model with benign and unknown variants, and then used a semi-supervised iterative balanced sampling (IBS) algorithm to gradually replace unknown variants with a set of pathogenic variants predicted with high confidence. Finally, we demonstrated that our model outperformed the existing methods in distinguishing de novo variants causing developmental disability disorder in humans from benign ones.

Adoption of Residual Block

FIG. 17 illustrates a residual block. Both our deep learning model of pathogenicity prediction and deep learning models for predicting secondary structure and solvent accessibility adopt the definition of residual blocks that was first illustrated in the. Structure of a residual block is shown in figure below. The input layer is first batch normalized, followed by the nonlinear activation "ReLU". The activation is then passed through a 1D convolution layer. This intermediate output from the 1D convolution layer is again batch normalized and ReLU activated, followed by another 1D convolution layer. At the end of the second 1D convolution, we merge its output with the original input. In such an architecture, the input is preserved in its original state and the residual connections are kept free of non-linear activations of the model.

Atrous/dilated convolutions allow for large receptive fields with few trainable parameters. An atrous/dilated convolution is a convolution where the kernel is applied over an area larger than its length by skipping input values with a certain step, also called atrous convolution rate or dilation factor. Atrous/dilated convolutions add spacing between the elements of a convolution filter/kernel so that neighboring input entries (e.g., nucleotides, amino acids) at larger intervals are considered when a convolution operation is performed. This enables incorporation of long-range contextual dependencies in the input. The atrous convolutions conserve partial convolution calculations for reuse as adjacent nucleotides are processed.

Novelty of Our Model

Our method differs from the existing methods for predicting pathogenicity of variants in three ways. First, our method adopts a novel architecture of semi-supervised deep convolutional neural networks. Second, reliable benign variants are obtained from human common variants from gnomAD and primate variants, while the highly confident pathogenic training set is generated through iterative balanced sampling and training, to avoid circular training and testing of models using the identical human curated variant databases. Third, deep learning models for secondary structure and solvent accessibility are integrated into the architecture of our pathogenicity model. The information obtained from the structure and solvent models are not limited to label prediction for specific amino acid residues. Rather, the readout layer is removed from the structure and solvent models, and the pre-trained models are merged with the pathogenicity model. While training the pathogenicity model, the structure and solvent pretrained layers also backpropagate to minimize the error. This helps the pre-trained structure and solvent model to focus on the pathogenicity prediction problem.

Training Secondary Structure and Solvent Accessibility Models

Data Preparation

We trained deep convolutional neural networks to predict the 3-state secondary structure and the 3-state solvent accessibility of the proteins. Protein annotations from PDB are used for training the models. Sequences with more than 25% similarity with their sequence profile are removed, according to one implementation. In total, 6,293 protein sequences are used for training, 392 for validation, and 499 for testing, according to one implementation.

The position-specific scoring matrix (PSSM) conservation profiles for the proteins are generated by running PSI-BLAST with E-value threshold 0.001 and 3 iterations to search UniRef90. Any unknown amino acid is set as blank, as well as its secondary structure. We also run PSI-BLAST with similar parameter settings for all human genes to collect their PSSM conservation profiles. These matrices are used for integrating the structure model to pathogenicity prediction. The amino acids of protein sequences are then converted into one-hot encoding vectors. And the protein sequences and PSSM matrices are reshaped to a matrix of L×20, where L is the length of a protein. The three predicted labels for secondary structure include helix (H), beta sheet (B) and coils (C). The three labels for solvent accessibility include buried (B), intermediate (I) and exposed (E). One label corresponds to one amino acid residue. The labels are coded as one-hot encoding vectors of dimension=3.

Model Architecture and Training

We trained two end-to-end deep convolutional neural network models to predict the 3-state secondary structure and 3-state solvent accessibility of proteins, respectively. The two models have similar configurations, including two input channels, one for protein sequences and the other for protein conservation profiles. Each input channel has the dimension L×20, where L denotes the length of a protein.

Each of the input channel is passed through a 1D convolution layer (layer 1a and 1b) with 40 kernels and linear activations. This layer is used to upsample the input dimensions from 20 to 40. Note all the other layers throughout the model use 40 kernels. The two layer (1a and 1b) activations are merged together by summing the values across each of the 40 dimensions (i.e., merge mode='sum'). The output of the merge node is passed through a single layer of 1D convolution (layer 2) followed by linear activation.

The activations from layer 2 is passed through a series of 9 residual blocks (layers 3 to 11) as defined above. The activations of layer 3 is fed to layer 4 and layer 4's activation is fed to layer 5 and so on. There are also skip connections that directly sum the output of every 3rd residual block (layers 5, 8 and 11). The merged activations is then fed to two 1D convolutions (layers 12 and 13) with ReLU activations. The activations from layer 13 is given to the softmax readout layer. The softmax computes the probabilities of the three-class outputs for the given input.

For the best secondary structure model, the 1D convolutions have an atrous rate of 1. For the solvent accessibility model, the last 3 residual blocks (layers 9, 10 and 11) have an atrous rate of 2 to increase the coverage of the kernels. The secondary structure of a protein is strongly dependent on the interactions of amino acids in close proximity. Thus models with higher kernel coverage improves the performance slightly. On the other hand, solvent accessibility is affected by the long-range interactions between amino acids. Therefore, for the model with high coverage of kernels using atrous convolutions, its accuracy is more than 2% higher than that of the short-coverage models.

The table below provides details about activations and parameters for each layer of the 3-state secondary structure prediction model, according to one implementation.

| Layer | Type | Number of Kernels, Window size | Shape | Atrous rate | Activation |
| --- | --- | --- | --- | --- | --- |
| Input Sequence (layer 1a) | Convolution 1D | 40, 1 | (L, 40) | 1 | Linear |
| Input PSSM (layer 1b) | Convolution 1D | 40, 1 | (L, 40) | 1 | Linear |
| Merging Sequence + PSSM | Merge (mode = Concatenate) | — | (L, 80) | — | — |
| Layer 2 | Convolution 1D | 40, 5 | (L, 40) | 1 | Linear |
| Layer 3 | Convolution 1D | 40, 5 | (L, 40) | 1 | ReLU |

| Layer | Type | Number of Kernels, Window size | Shape | Atrous rate | Activation |
|---|---|---|---|---|---|
| Layer 4 | Convolution 1D | 40, 5 | (L, 40) | 1 | ReLU |
| Layer 5 | Convolution 1D | 40, 5 | (L, 40) | 1 | ReLU |
| Layer 6 | Convolution 1D | 40, 5 | (L, 40) | 1 | ReLU |
| Layer 7 | Convolution 1D | 40, 5 | (L, 40) | 1 | ReLU |
| Layer 8 | Convolution 1D | 40, 5 | (L, 40) | 1 | ReLU |
| Layer 9 | Convolution 1D | 40, 5 | (L, 40) | 1 | ReLU |
| Layer 10 | Convolution 1D | 40, 5 | (L, 40) | 1 | ReLU |
| Layer 11 | Convolution 1D | 40, 5 | (L, 40) | 1 | ReLU |
| Merge activations | Merge layer 5, 8 and 11. mode = 'sum' | — | (L, 40) | — | — |
| Layer 12 | Convolution 1D | 40, 5 | (L, 40) | 1 | ReLU |
| Layer 13 | Convolution 1D | 40, 5 | (L, 40) | 1 | ReLU |
| Output layer | Convolution 1D | 1, 3 | (L, 3) | — | Softmax |

The details of the solvent accessibility model is shown in the table below, according to one implementation.

| Layer | Type | Number of Kernels, Window size | Shape | Atrous rate | Activation |
|---|---|---|---|---|---|
| Input Sequence (layer 1a) | Convolution 1D | 40, 1 | (L, 40) | 1 | Linear |
| Input PSSM (layer 1b) | Convolution 1D | 40, 1 | (L, 40) | 1 | Linear |
| Merging Sequence + PSSM | Merge (mode = Concatenate) | — | (L, 80) | — | — |
| Layer 2 | Convolution 1D | 40, 5 | (L, 40) | 1 | Linear |
| Layer 3 | Convolution 1D | 40, 5 | (L, 40) | 1 | ReLU |
| Layer 4 | Convolution 1D | 40, 5 | (L, 40) | 1 | ReLU |
| Layer 5 | Convolution 1D | 40, 5 | (L, 40) | 1 | ReLU |
| Layer 6 | Convolution 1D | 40, 5 | (L, 40) | 1 | ReLU |
| Layer 7 | Convolution 1D | 40, 5 | (L, 40) | 1 | ReLU |
| Layer 8 | Convolution 1D | 40, 5 | (L, 40) | 1 | ReLU |
| Layer 9 | Convolution 1D | 40, 5 | (L, 40) | 2 | ReLU |
| Layer 10 | Convolution 1D | 40, 5 | (L, 40) | 2 | ReLU |
| Layer 11 | Convolution 1D | 40, 5 | (L, 40) | 2 | ReLU |
| Merge activations | Merge layer 5, 8 and 11. mode = 'sum' | — | (L, 40) | — | — |
| Layer 12 | Convolution 1D | 40, 5 | (L, 40) | 1 | ReLU |
| Layer 13 | Convolution 1D | 40, 5 | (L, 40) | 1 | ReLU |
| Output layer | Convolution 1D | 1, 3 | (L, 3) | — | Softmax |

The secondary structure class of a specific amino acid residue is determined by the largest predicted softmax probabilities. The model is trained with accumulated categorical cross entropy loss function for the whole protein sequence using ADAM optimizer for optimizing the backpropagation.

The best testing accuracy for the 3-state secondary structure prediction model is 80.32%, similar to the state-of-the-art accuracy predicted by DeepCNF model on a similar training dataset.

The best testing accuracy for the 3-state solvent accessibility prediction model is 64.83%, similar to the current best accuracy predicted by RaptorX on a similar training dataset.

We integrated the pretrained 3-state secondary structure and solvent accessibility prediction models into our pathogenicity prediction model as explained below.

Training Models to Predict Pathogenicity of Variants

Input Features for Pathogenicity Prediction Model

As discussed above, for the pathogenicity prediction problem, there is a benign variant training set and an unknown variant training set for training the pathogenicity model. For each variant, we prepared the following input features to feed into our model.

The first input feature of each variant is its flanking amino acid sequence, i.e., 25 amino acids on each side of the variant obtained from the reference sequence of hg19, to provide the deep learning models of the sequence context of the variant. In total, this flanking reference sequence has 51 amino acids in length.

The second feature is the alternative amino acid that caused the variant. Instead of providing the reference-alternative amino acid pair directly, we provide the alternative flanking sequence to the model. The alternative flanking sequence is the same as the reference flanking sequence in the first feature, except that the middle position of the sequence contains the alternative amino acid, instead of the reference amino acid.

Both the sequences are then converted to one-hot encoded vectors of length 51×20, where each amino acid is represented by a vector of 20 zeros or ones.

Then three position weight matrices (PWM) are generated from multiple sequence alignments (MSA) of 99 vertebrates for the variant, including one for 12 primates, one for 47 mammals excluding primates, and one for 40 vertebrates excluding primates and mammals. Each PWM has the dimension of L×20, where L is the length of flanking sequences around the variant (in our case, L represents 51 amino acids). It comprises counts of amino acids seen in each category of species.

We also generate the PSSM matrices for the variant-flanking sequences of 51 amino acids from psi blast. This is used for the integration of 3-state secondary structure and solvent accessibility prediction models for pathogenicity prediction.

We train the pathogenicity model with the reference sequence (input1), alternate sequence (input2), PWM matrices for primates (input3), mammals (input4), vertebrates (inputs), and information from 3-state secondary structure and solvent accessibility models.

Deep Learning Model Training

FIG. 19 is a block diagram that provides an overview of the deep learning models workflow. The pathogenicity training models comprises five direct inputs and four indirect inputs. The five direct input features include reference sequence (1a), alternative sequence (1b), primate conservation (1c), mammal conservation (1d), and vertebrate conservation (1e). The indirect inputs include reference-sequence-based secondary structure (1f), alternative-sequence-based secondary structure (1g), reference-sequence-based solvent accessibility (1h), and alternative-sequence-based solvent accessibility (1i).

For indirect inputs 1f and 1g, we load the pretrained layers of secondary structure prediction model, excluding the softmax layer. For input 1f, the pretrained layers are based on the human reference sequence for the variants along with the PSSM generated by PSI-BLAST for the variant. Likewise, for input 1g, the pretrained layers of the secondary structure prediction models are based on the human alternative sequence as the input along with the PSSM matrix. Inputs 1h and 1i correspond to the similar pretrained channels containing the solvent accessibility information for reference and alternative sequences of the variant, respectively.

The five direct input channels are passed through an upsampling convolution layer of 40 kernels with linear activations. The layers 1a, 1c, 1d and 1e are merged with values summed across the 40 feature dimensions to produce layer 2a. In other words, the feature map of the reference sequence is merged with the three types of conservation feature maps. Similarly, 1b, 1c, 1d and 1e are merged with values summed across the 40 feature dimensions to generate layer 2b, i.e., the features of the alternative sequence is merged with the three types of conservation features.

The layers 2a and 2b are batch normalized with the activation of ReLU and each passed through a 1D convolution layer of filter size 40 (3a and 3b). The outputs of layers 3a and 3b are merged with 1f, 1g, 1h and 1i with the feature maps concatenated to each other. In other words, the feature maps of reference sequence with conservation profile, and alternative sequence with the conservation profile are merged with the secondary structure feature maps of the reference and alternative sequence and the solvent accessibility feature maps of the reference and alternative sequence (layer 4).

The outputs of layer 4 are passed through six residual blocks (layers 5, 6, 7, 8, 9, 10). The last three residual blocks have an atrous rate of 2 for the 1D convolutions, to give higher coverage for the kernels. The output of layer 10 is passed through a 1D convolution of filter size 1 and activation sigmoid (layer 11). The output of layer 11 is passed through a global maxpool that picks a single value for the variant. This value represents the pathogenicity of the variant. The details of one implementation of the pathogenicity prediction model are shown in the table below.

| Layer | Type | Number of Kernels, Window size | Shape | Atrous rate | Activation |
|---|---|---|---|---|---|
| Reference sequence (1a) | Convolution 1D | 40, 1 | (51, 40) | 1 | Linear |
| Alternative sequence (1b) | Convolution 1D | 40, 1 | (51, 40) | 1 | Linear |
| Primate conservation (1c) | Convolution 1D | 40, 1 | (51, 40) | 1 | Linear |
| Mammal Conservation (1d) | Convolution 1D | 40, 1 | (51, 40) | 1 | Linear |
| Vertebrate Conservation (1e) | Convolution 1D | 40, 1 | (51, 40) | 1 | Linear |
| Reference-sequence-based Secondary structure (1f) | Input layer | — | (51, 40) | — | — |
| Alternative-sequence-based secondary structure (1g) | Input layer | — | (51, 40) | — | — |
| Reference-sequence-based solvent accessibility (1h) | Input layer | — | (51, 40) | — | — |
| Alternative-sequence-based solvent accessibility (1i) | Input layer | — | (51, 40) | — | — |
| Reference sequence merge (2a) | Merge (mode = Sum) (1a, 1c, 1d, 1e) | — | (51, 40) | — | — |
| Alternative sequence merge (2b) | Merge (mode = Sum) (1b, 1c, 1d, 1e) | — | (51, 40) | — | — |
| 3a | Convolution 1D (2a) | 40, 5 | (51, 40) | 1 | ReLU |

| Layer | Type | Number of Kernels, Window size | Shape | Atrous rate | Activation |
|---|---|---|---|---|---|
| 3b | Convolution 1D (2b) | 40, 5 | (51, 40) | 1 | ReLU |
| 4 | Merge (mode = concatenate) (3a, 3b, 1f, 1g, 1h, 1i) | — | (51, 240) | — | — |
| 5 | Convolution 1D | 40, 5 | (51, 40) | 1 | ReLU |
| 6 | Convolution 1D | 40, 5 | (51, 40) | 1 | ReLU |
| 7 | Convolution 1D | 40, 5 | (51, 40) | 1 | ReLU |
| 8 | Convolution 1D | 40, 5 | (51, 40) | 1 | ReLU |
| 9 | Convolution 1D | 40, 5 | (51, 40) | 2 | ReLU |
| 10 | Convolution 1D | 40, 5 | (51, 40) | 2 | ReLU |
| 11 | Convolution 1D | 40, 1 | (51, 1) | 2 | Sigmoid |
| 12 | Global max pooling | — | 1 | — | — |
| Output layer | Activation layer | — | 1 | — | Sigmoid |

Ensembles

In one implementation, for each cycle of our method, we ran eight different models that train on the same benign data set and eight different unknown data sets and averaged the prediction of evaluation data sets across the eight models. Sampling bias can be reduced and well controlled when multiple randomly-sampled sets of unknown variants are presented to the model.

Furthermore, adoption of ensemble-of-ensembles approach can improve the performance of our model on our evaluation dataset. CADD uses an ensemble of 10 models and gets the average score across all the 10 models to score a variant. Here we attempted to use a similar ensemble approach. We benchmarked the results using one ensemble and then increased the number of ensembles to assess the performance gain. Note that each ensemble has eight models that train on the same benign data set and eight different unknown data sets. For different ensembles, the seed values of the random number generator are distinct so that the random variant sets are drawn differently from each other.

The detailed results according to one implementation are shown in the table below.

| Number of Ensembles | -log(pvalue) on DDD dataset (mean of mean of ensembles) | -log(pvalue) on DDD dataset (median of mean of ensembles) |
|---|---|---|
| 1 | 3.4e−27 | 3.4e−27 |
| 5 | 2.74e−29 | 3.8e−29 |
| 10 | 2.98e−29 | 2.55e−29 |
| 15 | 4.06e−29 | 3.88e−29 |
| 20 | 3.116e−29 | 3.05e−29 |
| 25 | 3.77e−29 | 3.31e−29 |
| 30 | 3.81e−29 | 3.34e−29 |

Compared with one ensemble, 5 ensembles and 10 ensembles produced more significant p-values when evaluated using DDD datasets. But increasing the number of ensembles fails to improve the performance further, indicating a saturation for ensembles. The ensembles reduce sampling bias with a large variety of unknown variants. However, we also required matching the 192 trinucleotide contexts between benign and pathogenic classes, which limits our sampling space substantially, leading to the quick saturation. We conclude that ensemble-of-ensembles approach improves the model performance significantly and further enriches our understanding of models.

Early Stopping for Training Pathogenicity Model

Since there lacks reliable annotated pathogenic variant samples, it is challenging to define stopping criteria for model training. To avoid using pathogenic variants in model evaluation, in one implementation, we used the 10,000 benign validation variants from orthologous primates and 10,000 trinucleotide-context-matched unknown variants. After training each epoch of the model, we evaluated the benign validation variants and the unknown validation variants. We used Wilcoxon rank-sum test to assess the difference of the probability distributions of both of the validation variant sets.

The p-value of the test becomes more significant with improvements in the model's ability to distinguish benign variants from a set of unknown variants. We stop the training if no improvement is observed in the model's ability to distinguish between the two distributions during any five consecutive epochs of model training.

Earlier, we had set aside two separate sets of 10,000 withheld primate variants from training, which we termed the validation set and the test set. We used the validation set of 10,000 withheld primate variants and 10,000 unlabeled variants that were matched for trinucleotide context for evaluating early stopping during model training. After each training epoch, we evaluated the ability of the deep neural network to discriminate between variants in the labeled benign validation set and the unlabeled matched controls, measuring the difference in the distributions of the predicted scores using the Wilcoxon rank-sum test. We stopped the training once no further improvement was observed after five consecutive training epochs to prevent overfitting.

Benchmarking of Classifier Performance

We assessed the classification accuracy of two versions of the deep learning network, one trained with common human variants only, and one trained with the full benign labeled dataset including both common human variants and primate variants, in addition to the following classifiers: SIFT, PolyPhen-2, CADD, REVEL, M-CAP, LRT, Mutation-Taster, MutationAssessor, FATHMM, PROVEAN, VEST3, MetaSVM, MetaLR, MutPred, DANN, FATHMM-MKL_coding, Eigen, GenoCanyon, and GERP++13,32-48. To obtain the scores for each of the other classifiers, we downloaded the scores for all missense variants from dbNSFP 49 (https://sites.google.com/site/jpopgen/dbNSFP), and benchmarked the methods on the 10,000 withheld primate variant test set, and on de novo variants in DDD cases versus controls. We selected SIFT, PolyPhen-2, and CADD for inclusion in the main paper because they are among the most widely used methods, and REVEL, because across the different modes of evaluation, it stood out as being one of the best of the 20 existing classifiers we evaluated. The performance for all classifiers we evaluated is provided in FIG. 28A.

For evaluating the impact of available training data size on the performance of the deep learning network, we trained deep learning networks at each data point in FIG. 6, by randomly sampling from the labeled benign training set of 385,236 primate and common human variants. To reduce random noise in the performance of the classifiers, we performed this training procedure five times, each time using a random instantiation of initial parameter weights, and showed the median performance on both the 10,000 withheld primate variants and the DDD case vs controls dataset in FIG. 6. By chance, the performance of the median classifier with the full dataset of 385,236 labeled benign variants was slightly better than the one we used for the rest of the paper on the DDD dataset ($P<10^{-29}$ instead of $P<10^{-28}$ by Wilcoxon rank-sum test). To show that variants from each individual primate species contributes to classification accuracy whereas variants from each individual mammal species lower classification accuracy, we trained deep learning networks using a training dataset comprising 83,546 human variants plus a constant number of randomly selected variants for each species, according to one implementation. According to one implementation, the constant number of variants we added to the training set (23,380) is the total number of variants available in the species with the lowest number of missense variants, i.e. bonobo. To reduce noise, we again repeated the training procedure five times, and reported the median performance of the classifier.

Model Evaluation

In one implementation, we trained 21 cycles of deep learning models following the iterative balanced sampling procedure. We performed two types of evaluations to assess the performance of our classifiers. We also compared our models with Polyphen2, SIFT, and CADD on the two metrics and assessed the potential of application of our models for clinical annotation.

Method 1: Benign Test Set Accuracy

In one implementation, we evaluated the 10,000 benign variants and unknown variants by computing their predicted probabilities using an ensemble of eight different trained models. We also obtained their predicted probabilities scored by the other existing methods mentioned above.

We then obtained the median of predicted probabilities across the unknown test variants for each of the methods used in the evaluation. Using the median score, we found the number of benign variants that scored above or below the median depending on the annotation of benign and pathogenic variants used by each of the methods. SIFT, CADD and our method label pathogenic variants as 1 and benign variants as 0. Thus, we counted the number of benign variants that scored below the median. Polyphen uses the opposite annotation and we counted the number of benign variants above the median. The ratio of the number of benign variants scored above/below the median divided by the total number of benign variants represents the prediction accuracy of benign variants.

Benign accuracy=Total number of benign variants above (below*) the median÷Total number of benign variants Our reasoning behind this evaluation method relies on the analysis of selective pressure of variants in gnomAD. For the singletons in gnomAD, the ratio of missense variants to synonymous variants is ~2.26:1. While for the common variants (MAF>0.1%) in gnomAD, the missense-to-synonymous ratio is ~1.06:1. This indicates that from a set of random unknown variants, approximately 50% are expected to be purged by natural selection and the remaining 50% tend to be mild and likely become common in the population.

| Method | Accuracy of withheld benign set |
|---|---|
| Polyphen | 0.74 |
| SIFT | 0.69 |
| CADD | 0.77 |
| Our Model | 0.85 |

As shown in the table above, our method outperforms the second best method CADD by more than 8%. This shows an significant improvement in our model's ability to classify the benign variants. While such a demonstration proves the ability of our model, the following Method 2 shows the usefulness of our model on clinical datasets for clinical interpretation.

Method 2: Clinical Dataset Evaluation

In one implementation, we evaluated these pathogenicity prediction methods on clinical datasets, including developmental disability disorder (DDD) case-control dataset. DDD dataset comprise 3,821 de novo missense variants from affected children and 1,231 de novo missense variants from their unaffected siblings. Our hypothesis is that the de novo variants from affected children tend to be more deleterious than the de novo variants from their unaffected siblings.

As clinical test datasets do not clearly label pathogenic variants, we used the separation between the two sets of de novo variants (from affected and unaffected) to gauge the performance of those methods. We applied Wilcoxon rank-sum test to evaluate how well the separation of these two sets of de novo variants is.

| Method | -log10(p-value) on DDD dataset |
|---|---|
| Polyphen | 15.02 |
| SIFT | 13.52 |
| CADD | 13.83 |
| DL | 28.35 |

According to the table above, our semi-supervised deep learning models performs significantly better in distinguishing the affected set of de novo variants from the unaffected set. This shows that our model is more appropriate for clinical interpretation than the existing methods. This also validates that the general approach of extracting features from genome sequences and conservation profiles is superior to the manually-crafted features based on human curated datasets.

Benign Prediction Accuracy on a Withheld Test Set of 10,000 Primate Variants

We used the 10,000 withheld primate variants in the test dataset to benchmark the deep learning network as well as the other 20 classifiers. Because the different classifiers had widely varying score distributions, we used 10,000 randomly selected unlabeled variants that were matched to the test set by tri-nucleotide context to identify the 50th-percentile threshold for each classifier. To ensure fair comparison between the methods, we benchmarked each classifier on the fraction of variants in the 10,000 withheld primate variant test set that were classified as benign at the 50th-percentile threshold for that classifier.

Our reasoning behind using the 50th-percentile to identify benign variants is based on the selective pressure observed for missense variants in the ExAC/gnomAD dataset. For variants occurring at singleton allele frequency, the missense:synonymous ratio is ~2.2:1, whereas for common variants (>0.1% allele frequency), the missense:synonymous ratio is ~1.06:1. This indicates that approximately 50% of missense variants are expected to be purged by natural selection at common allele frequencies, and the remaining 50% are mild enough to have the potential to become common in the population via genetic drift.

Figure 28:
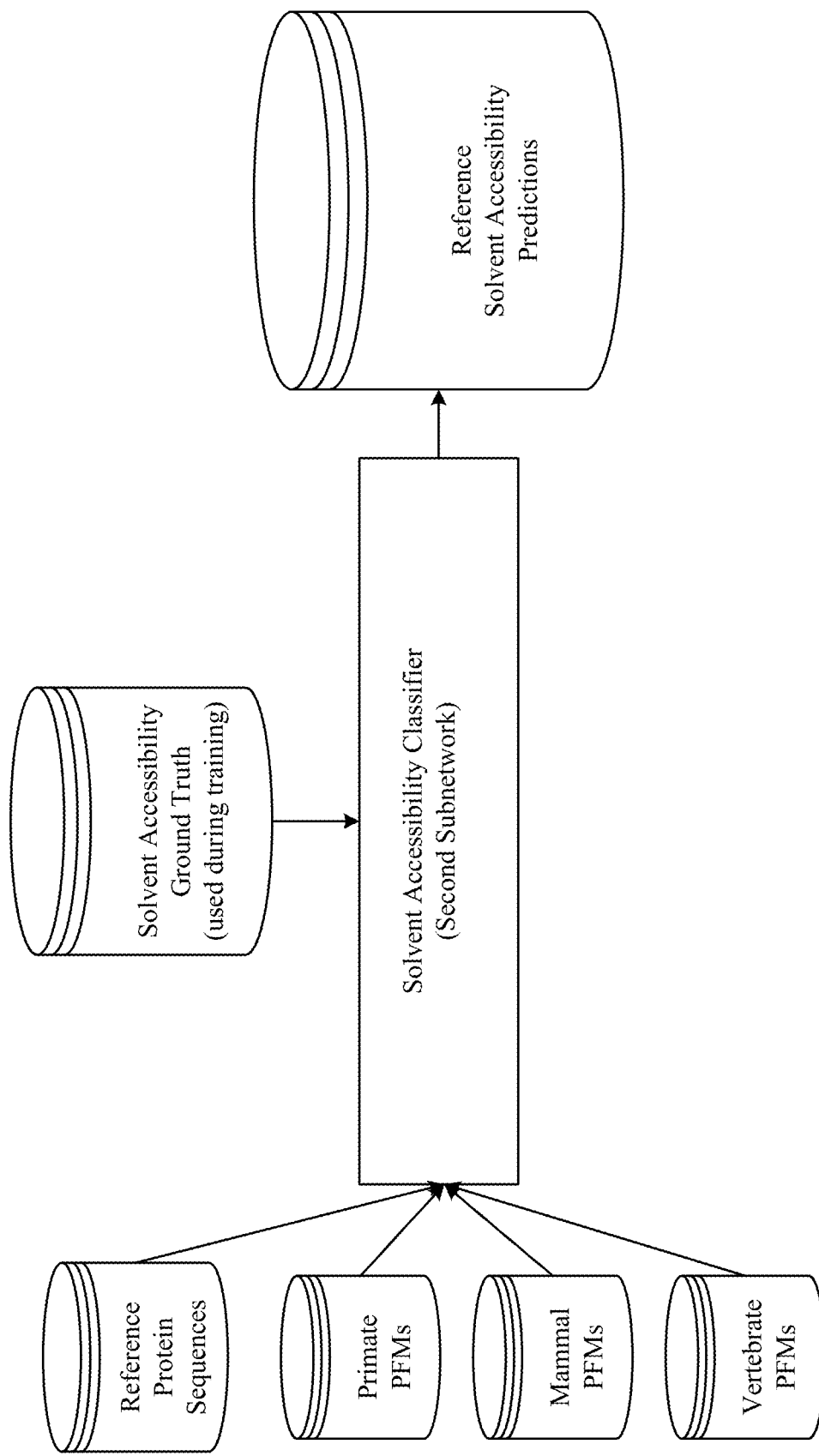
Figure 29:
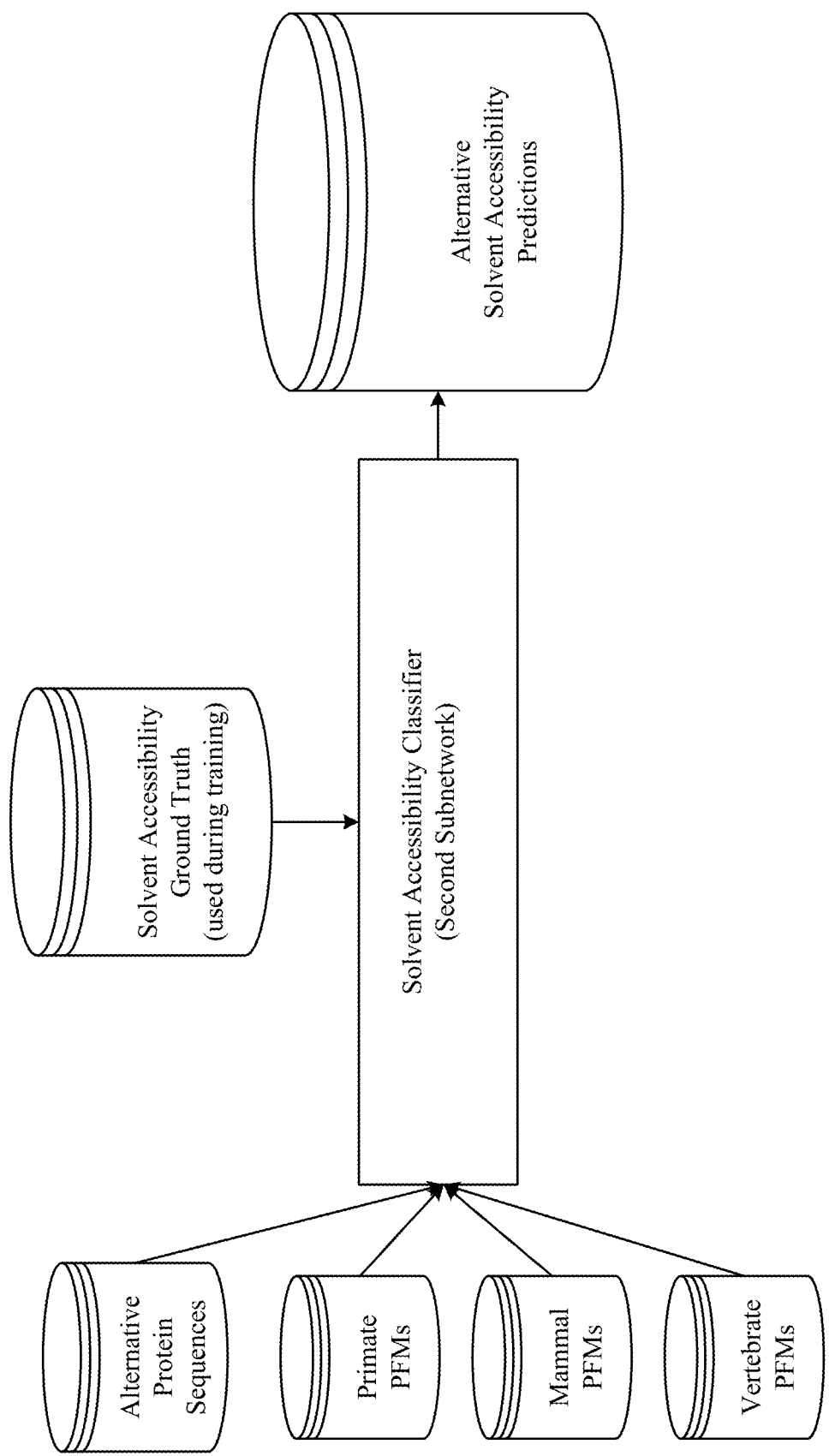
Figure 30:
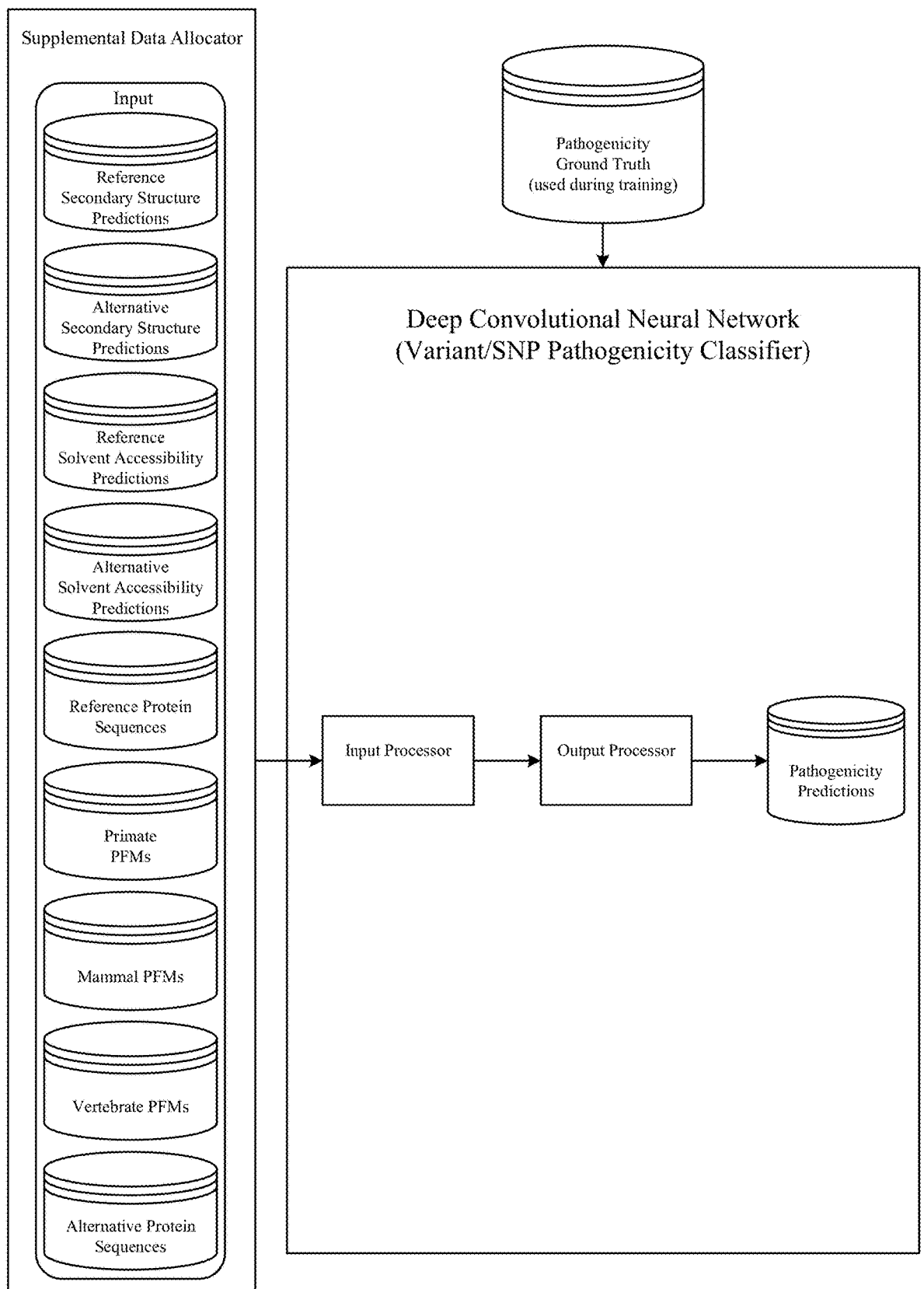
FIG. 30 operation of a variant pathogenicity classifier. As used herein, the term variant also refers to single nucleotide polymorphisms (abbreviated SNPs) and generally to single nucleotide variants (abbreviated SNVs).

For each of the classifiers, the fraction of withheld primate test variants predicted as benign using the 50th-percentile threshold is shown (FIG. 28A and (FIG. 34)).

Interpreting the Deep Learning Models

Understanding the means by which machine learning algorithms solve problems is often difficult. We visualized the initial layers of the deep learning network to understand the features that it had learned to extract in order to predict variant pathogenicity. We calculated the correlation coefficients for different amino acids within the first three layers (the first convolutional layer following two upsampling layers) of the pretrained 3-state secondary structure prediction models, and showed that the weights of the convolutional layers learn features very similar to the BLOSUM62 matrix or Grantham distance.

Figure 27:
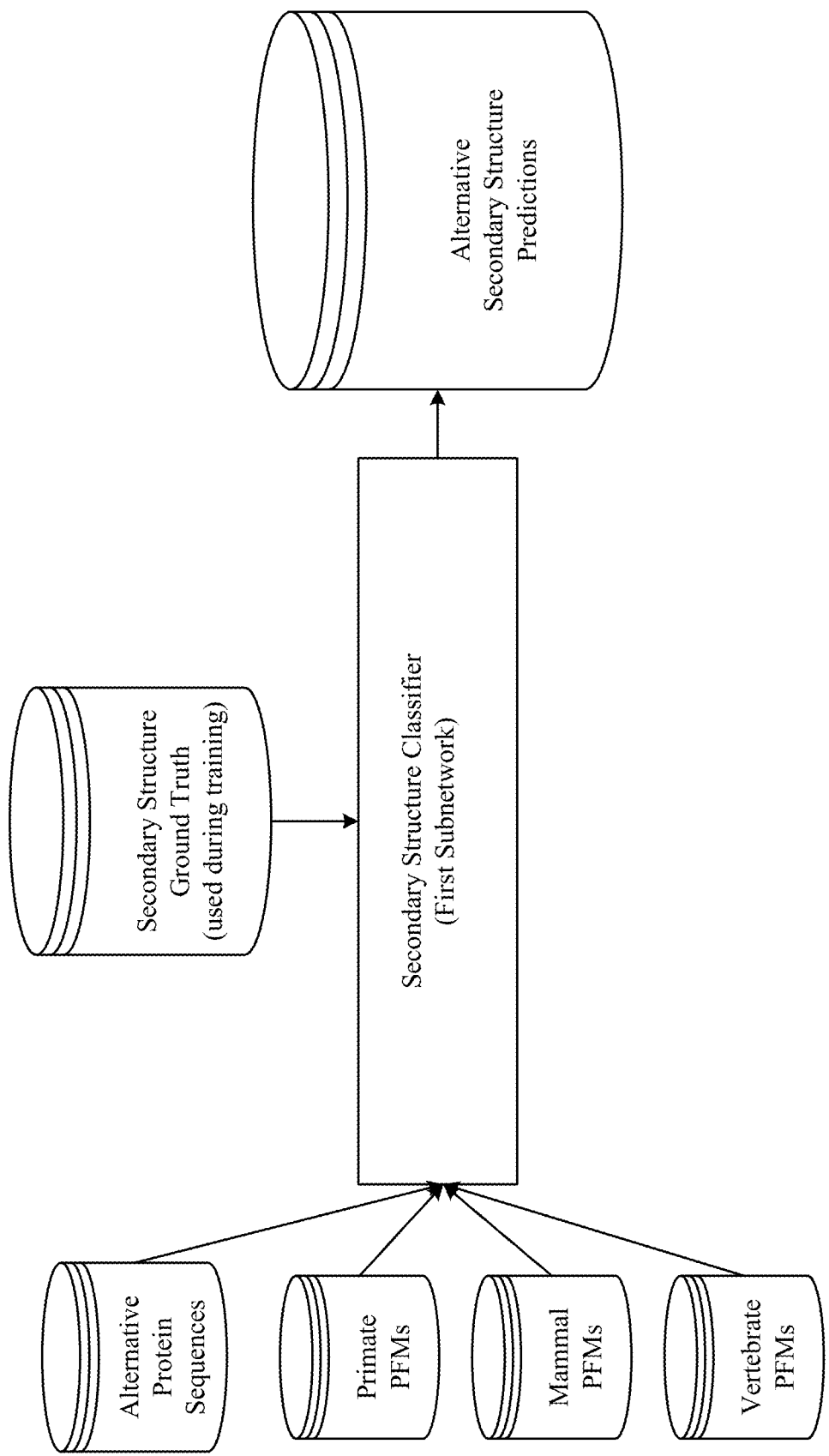

To compute the correlation coefficients between the different amino acids, we started with weights of the first convolutional layer preceded by three upsampling layers (layers 1a, 1b and 1c) in the secondary structure model. We performed matrix multiplication between the three layers, resulted in a matrix with dimensions (20,5,40), where 20 is the number of amino acids, 5 is the window size of the convolutional layer, and 40 is the number of kernels. We reshaped the matrix to have the dimension (20,200) by flattening the last two dimensions, obtaining a matrix in which the weights operating on each of the 20 amino acids were represented as a 200-length vector. We calculated the correlation matrix between the 20 amino acids. Since each dimension represents each amino acid, by calculating the correlation coefficient matrix we are calculating the correlation between the amino acids, and how similar they appear to the deep learning network, based on what it has learned from the training data. The visualization of the correlation coefficient matrix is shown in FIG. 27 (amino acids sorted by BLOSUM62 matrix order), and shows two prominent clusters, comprising the hydrophobic amino acids (Methionine, Isoleucine, Leucine, Valine, Phenylalanine, Tyrosine, Tryptophan), and the hydrophilic amino acids (Asparagine, Aspartic Acid, Glutamic Acid, Glutamine, Arginine, and Lysine). The outputs of these initial layers become the inputs for later layers, enabling the deep learning network to construct increasingly complex hierarchical representations of the data.

Figure 25:
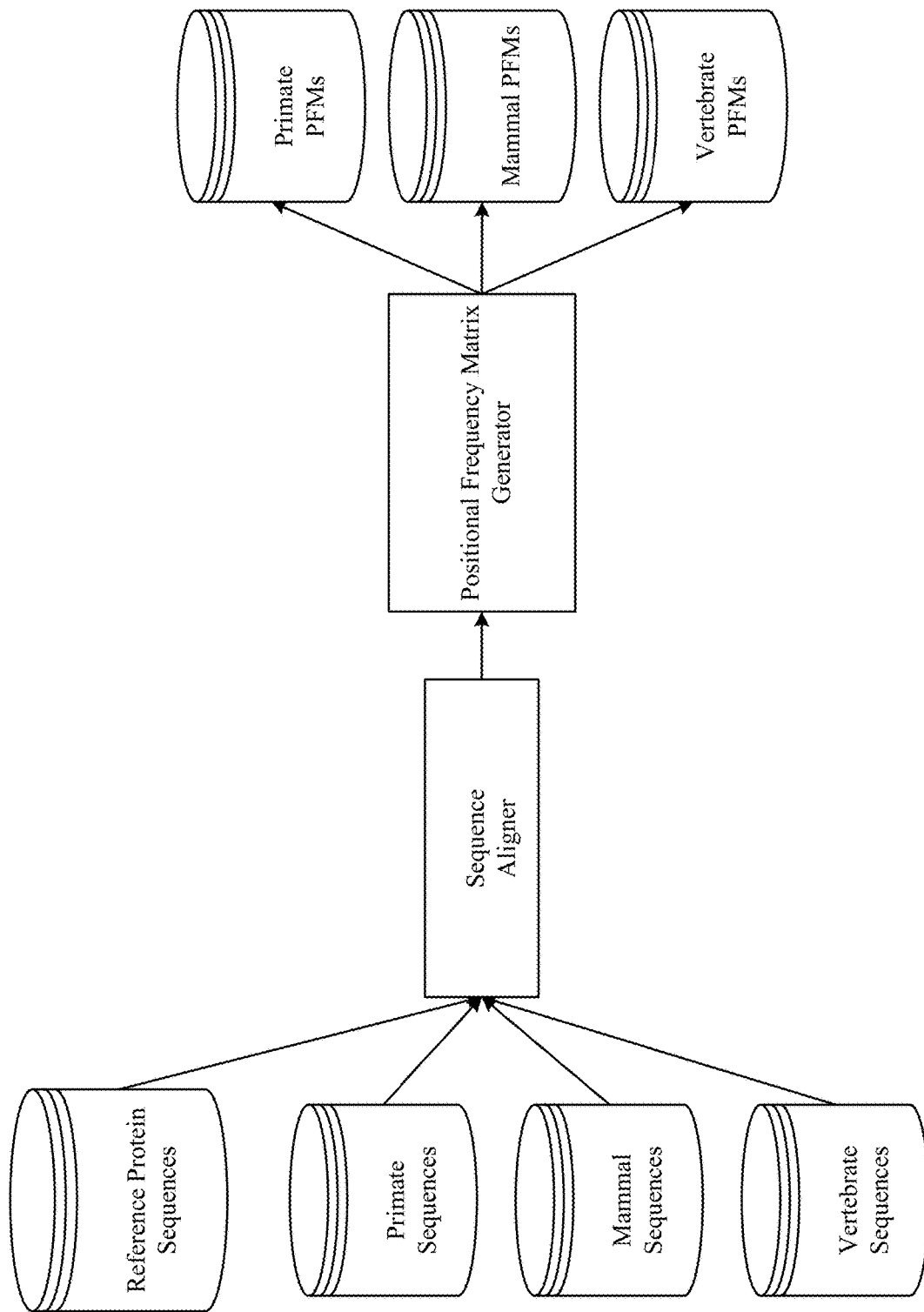
FIG. 25 is one implementation of generating position frequency matrices (abbreviated PFMs), also called position weight matrices (abbreviated PWMs) or position-specific scoring matrix (abbreviated PSSM).
Figure 26:
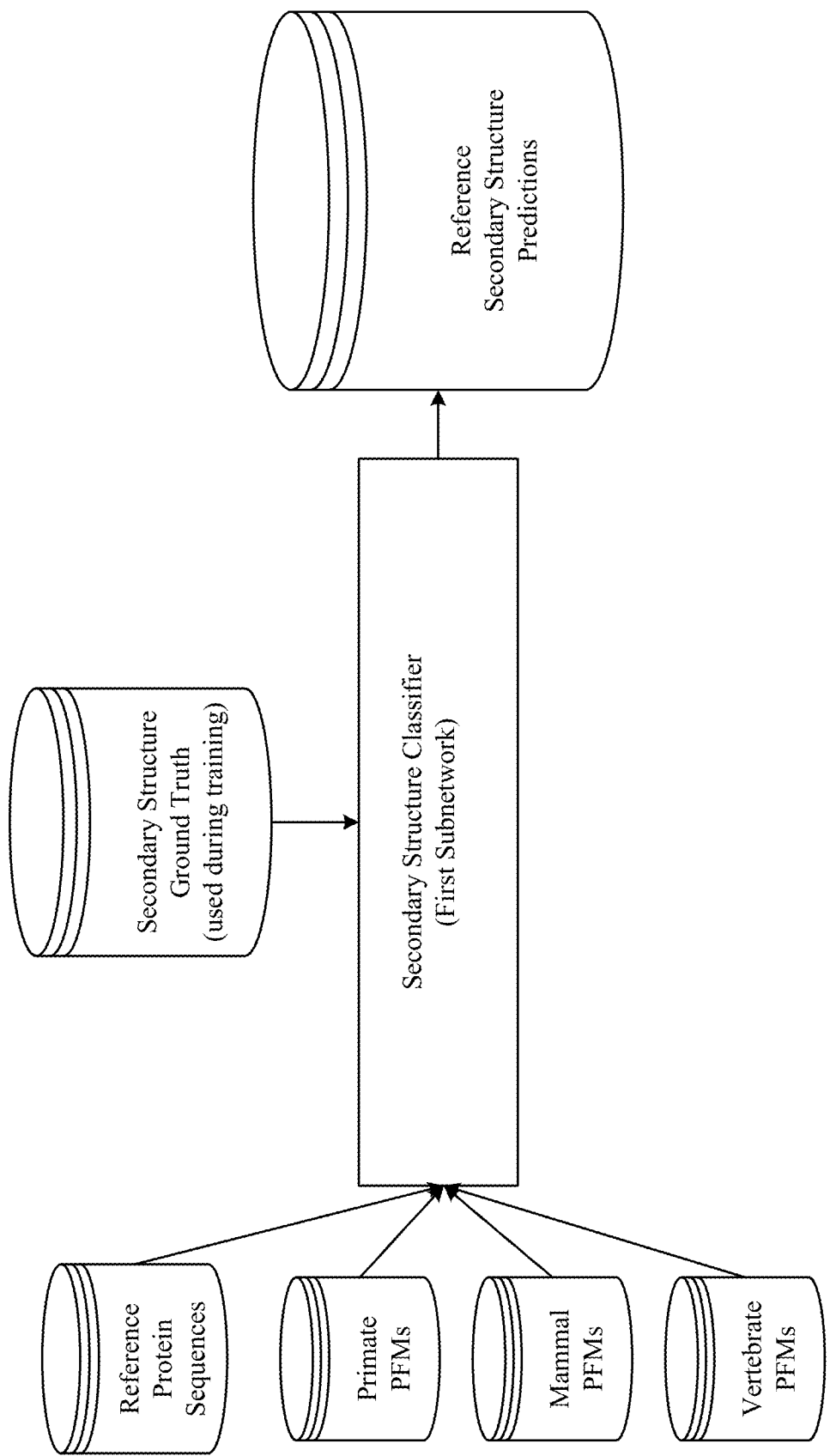
FIGS. 26, 27, 28, and 29 show processing of the secondary structure and solvent accessibility subnetworks.

To illustrate the window of amino acid sequence used by the neural network in its predictions, we perturbed each position in and around 5000 randomly selected variants to observe its effects on the predicted PrimateAI score for the variant (FIG. 25B). We systematically zeroed out the inputs at each nearby amino acid position (−25 to +25) around the variant, and measured the change in the neural network's predicted pathogenicity of the variant, and plotted the average absolute value of the change across the 5000 variants. Amino acids near the variant have the greatest effect, in a roughly symmetric distribution, gradually tailing off as distance from the variant increases. Importantly, the model makes its predictions based not only on the amino acid at the position of the variant, but by using information from a wider window, as would be needed to recognize protein motifs. Consistent with the relatively compact size of protein subdomains, we empirically observed that extending the size of the window to more than 51 amino acids did not further improve accuracy.

To evaluate the sensitivity of the deep learning classifier to alignment, we examined the effects of the depth of the alignment on the accuracy of variant classification as follows. We split the data into five bins based on the number of species in the alignment, and evaluated the accuracy of the network in each bin. We found that the accuracy of the network at separating a set of withheld benign mutations from randomly selected mutations that were matched for trinucleotide context is strongest at the top three bins and noticeably weaker in the bottom two bins. The 99 vertebrate multi-species alignment comprises 11 non-human primates, 50 mammals, and 38 vertebrates, with the bottom two bins representing proteins that have sparse alignment information from other non-primate mammals. The deep learning network is robust and accurate when alignment information extends throughout primates and mammals, with conservation information from more distant vertebrates being less important.

Per-Gene Enrichment Analysis

In one implementation, the deep convolutional neural network-based variant pathogenicity classifier is further configured to implement a per-gene enrichment analysis which confirms pathogenicity of variants that have been determined to be pathogenic. For a particular gene sampled from a cohort of individuals with a genetic disorder, the per-gene enrichment analysis includes applying the deep convolutional neural network-based variant pathogenicity classifier to identify candidate variants in the particular gene that are pathogenic, determining a baseline number of mutations for the particular gene based on summing observed trinucleotide mutation rates of the candidate variants and multiplying the sum with a transmission count and a size of the cohort, applying the deep convolutional neural network-based variant pathogenicity classifier to identify de novo missense variants in the particular gene that are pathogenic, and comparing the baseline number of mutations with a count of the de novo missense variants. Based on an output of the comparison, the per-gene enrichment analysis confirms that the particular gene is associated with the genetic disorder and that the de novo missense variants are pathogenic. In some implementations, the genetic disorder is autism spectrum disorder (abbreviated ASD). In other implementations, the genetic disorder is developmental delay disorder (abbreviated DDD).

In some implementations, the deep convolutional neural network-based variant pathogenicity classifier is further configured to perform the comparison using a statistical test that produces a p-value as the output.

In other implementations, the deep convolutional neural network-based variant pathogenicity classifier is further configured to compare the baseline number of mutations with the count of the de novo missense variants and, based on the output of the comparison, confirm that the particular gene is not associated with the genetic disorder and that the de novo missense variants are benign.

Genome-Wide Enrichment Analysis

In another implementation, the deep convolutional neural network-based variant pathogenicity classifier is further configured to implement a genome-wide enrichment analysis which confirms pathogenicity of variants that have been determined to be pathogenic. The genome-wide enrichment analysis includes applying the deep convolutional neural network-based variant pathogenicity classifier to identify a first set of de novo missense variants that are pathogenic in a plurality of genes sampled from a cohort of healthy individuals, applying the deep convolutional neural network-based variant pathogenicity classifier to identify a second set of de novo missense variants that are pathogenic in the plurality of genes sampled from a cohort of individuals with a genetic disorder, and comparing respective counts of the first and second sets, and based on an output of the comparison confirming that the second set of de novo missense variants are enriched in the cohort of individuals with the genetic disorder and therefore pathogenic. In some implementations, the genetic disorder is autism spectrum disorder (abbreviated ASD). In other implementations, the genetic disorder is developmental delay disorder (abbreviated DDD).

In some implementations, the deep convolutional neural network-based variant pathogenicity classifier is further configured to perform the comparison using a statistical test that produces a p-value as the output. In one implementation, the comparison is further parametrized by respective cohort sizes.

In some implementations, the deep convolutional neural network-based variant pathogenicity classifier is further configured to compare the respective counts of the first and second sets, and based on the output of the comparison confirming that the second set of de novo missense variants are not enriched in the cohort of individuals with the genetic disorder and therefore benign.

Particular Implementations

A base refers to a nucleotide base or nucleotide, A (adenine), C (cytosine), T (thymine), or G (guanine).

This application uses the terms "protein" and "translated sequence" interchangeably.

This application uses the terms "codon" and "base triplet" interchangeably.

This application uses the terms "amino acid" and "translated unit" interchangeably.

This application uses the phrases "variant pathogenicity classifier", "convolutional neural network-based classifier for variant classification", and "deep convolutional neural network-based classifier for variant classification" interchangeably.

We describe systems, methods, and articles of manufacture for constructing a variant pathogenicity classifier. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

A system implementation of the technology disclosed includes one or more processors coupled to the memory. The memory is loaded with computer instructions to train a splice site detector that identifies splice sites in genomic sequences (e.g., nucleotide sequences).

Figure 33:
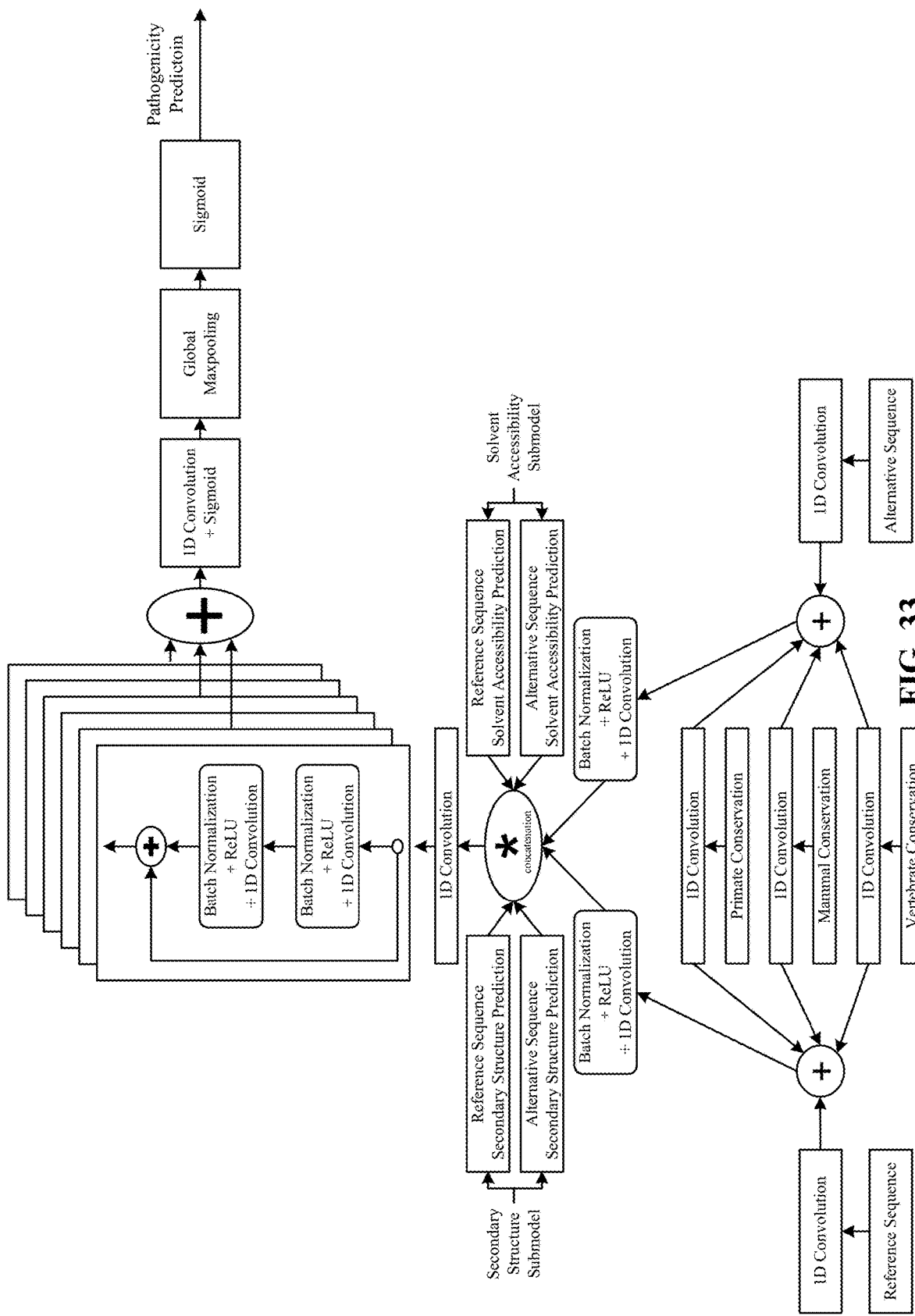
FIG. 33 shows a neural network architecture of the variant pathogenicity classifier.

As shown in FIG. 33, the system trains a convolutional neural network-based variant pathogenicity classifier, which runs on numerous processors coupled to memory. The system uses benign training examples and pathogenic training examples of protein sequence pairs generated from benign variants and pathogenic variants. The benign variants include common human missense variants and non-human primate missense variants occurring on alternative non-human primate codon sequences that share matching reference codon sequences with humans.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

Figure 51:
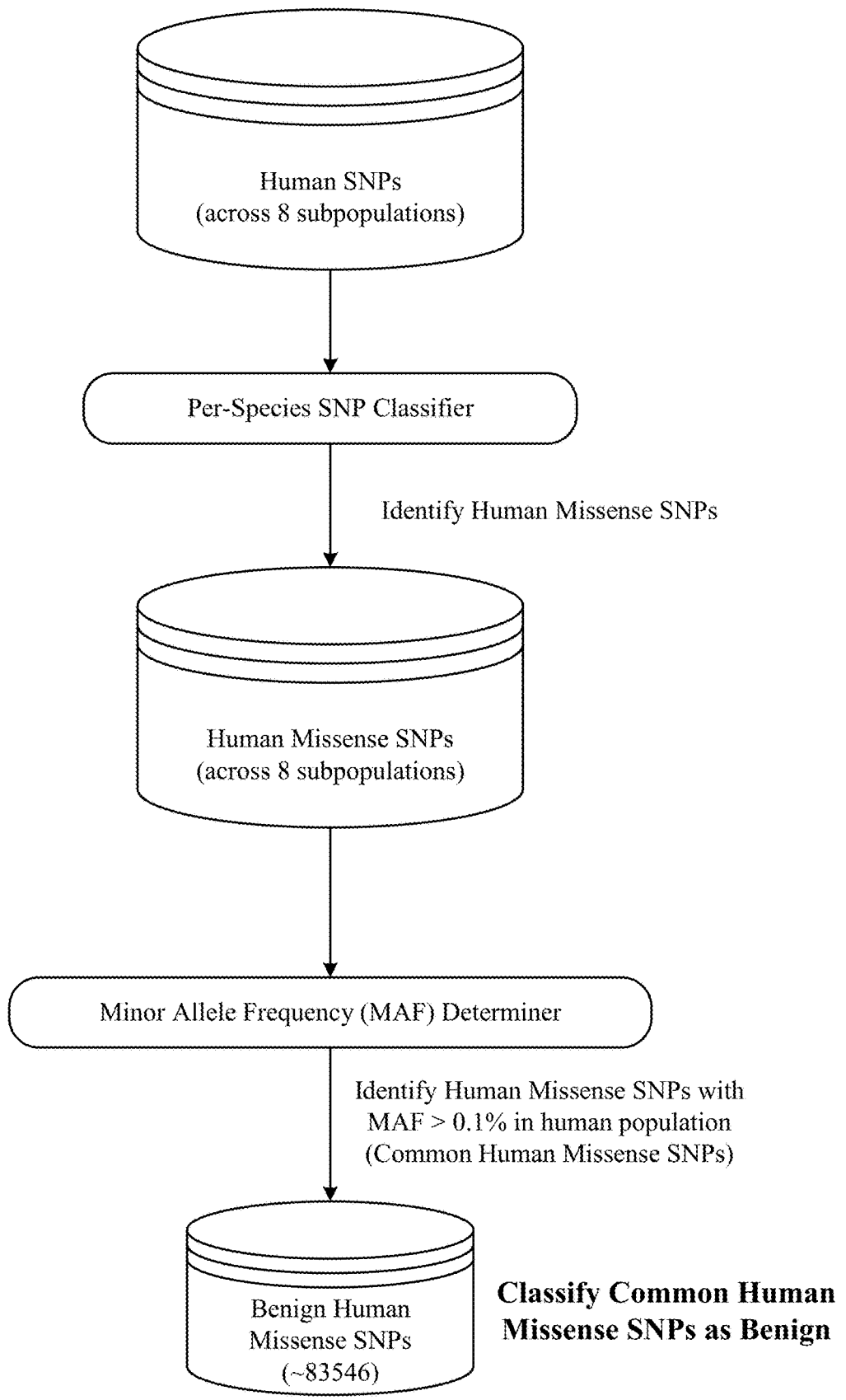
FIG. 51 depicts one implementation of generating benign human missense SNPs.

As shown in FIG. 51, the common human missense variants have a minor allele frequency (abbreviated MAF) greater than 0.1% across a human population variant dataset sampled from at least 100000 humans.

As shown in FIG. 51, the sampled humans belong to different human subpopulations and the common human missense variants have a MAF greater than 0.1% within respective human subpopulation variant datasets.

The human subpopulations include African/African American (abbreviated AFR), American (abbreviated AMR), Ashkenazi Jewish (abbreviated ASJ), East Asian (abbreviated EAS), Finnish (abbreviated FIN), Non-Finnish European (abbreviated NFE), South Asian (abbreviated SAS), and Others (abbreviated OTH).

Figure 50:
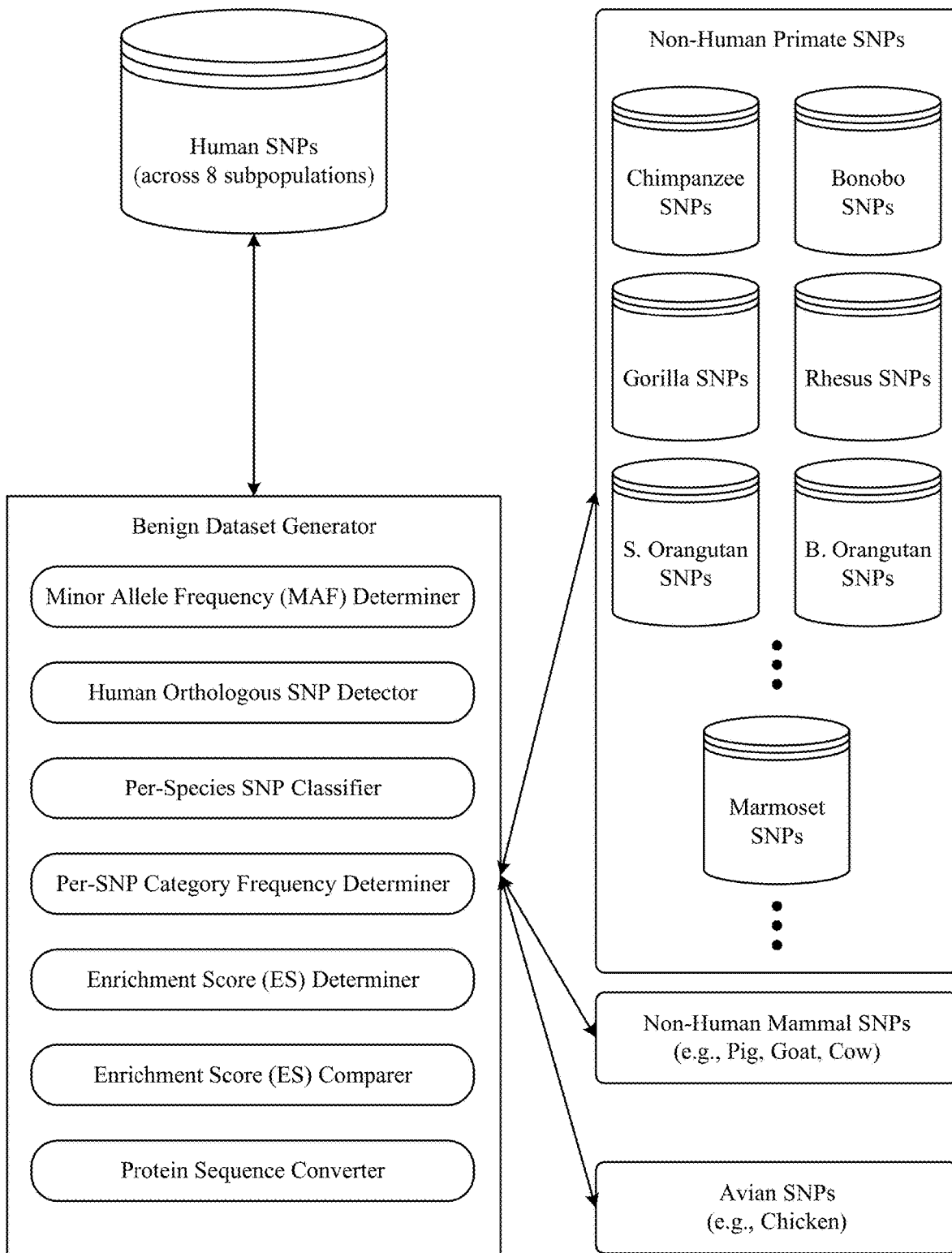
FIG. 50 illustrates one implementation of a computing environment used to generate the benign dataset.

As shown in FIGS. 50 and 51, the non-human primate missense variants include missense variants from a plurality of non-human primate species, including Chimpanzee, Bonobo, Gorilla, B. Orangutan, S. Orangutan, Rhesus, and Marmoset.

Figure 52:
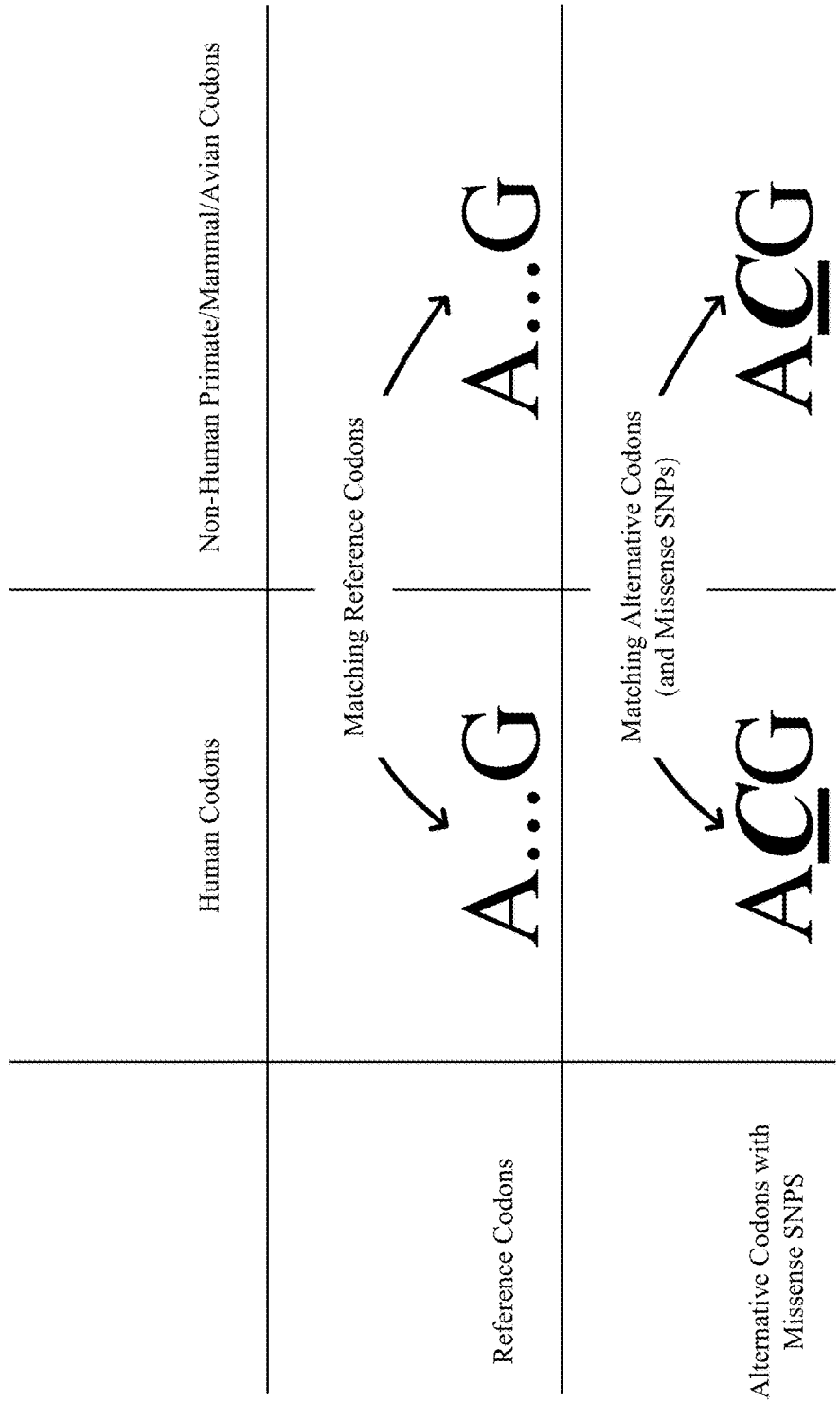
FIG. 52 shows one implementation of human orthologous missense SNPs. A missense SNP in a non-human species that has matching reference and alternative codons with humans.
Figure 53:
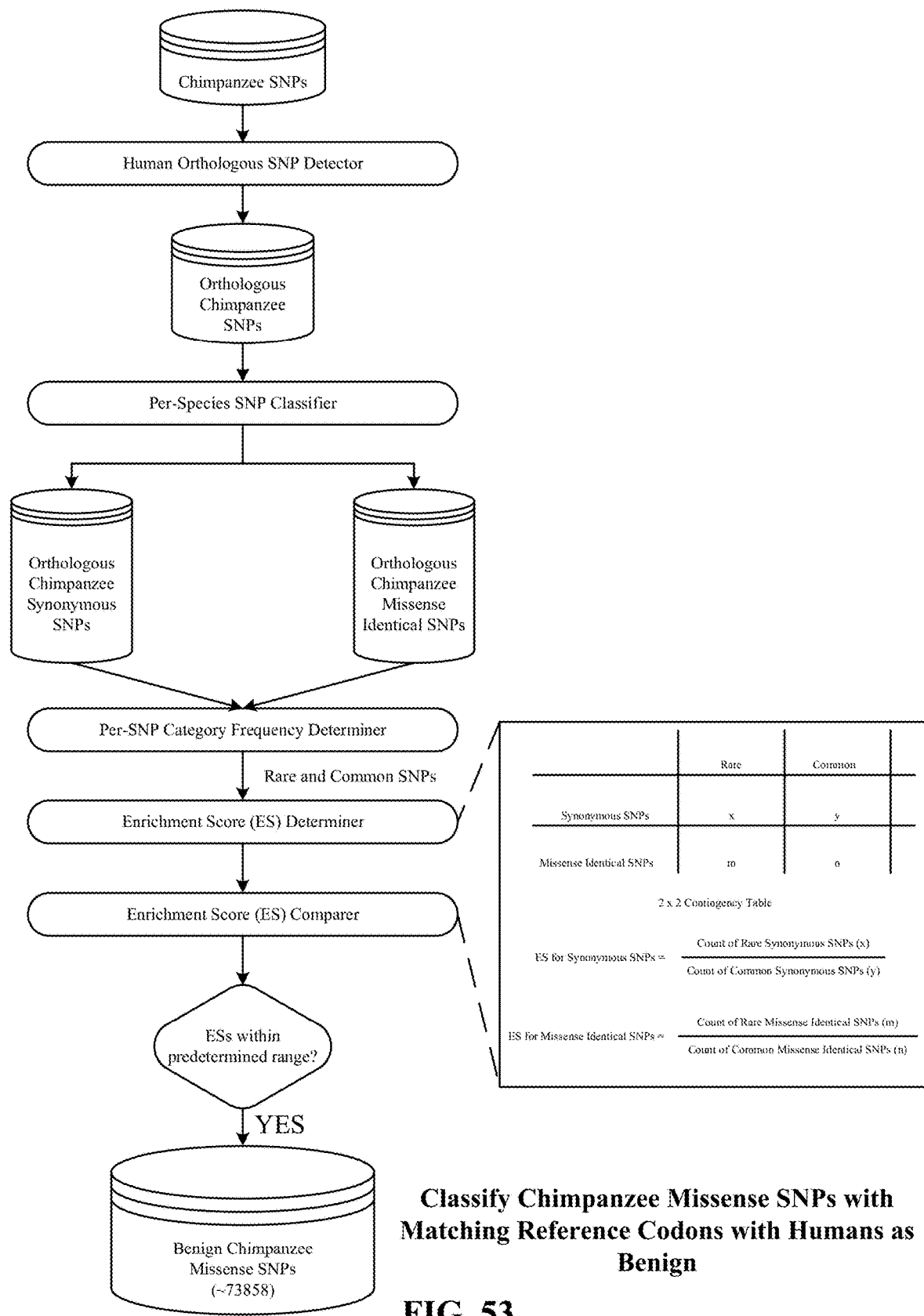
FIG. 53 depicts one implementation of classifying, as benign, SNPs of a non-human primate species (e.g., Chimpanzee) with matching reference codons with humans.

As shown in FIGS. 52 and 53, based on an enrichment analysis, the system accepts a particular non-human primate species for inclusion of missense variants of the particular non-human primate species among the benign variants. The enrichment analysis includes, for the particular non-human primate species, comparing a first enrichment score of synonymous variants of the particular non-human primate species to a second enrichment score of missense identical variants of the particular non-human primate species.

FIG. 52 shows one implementation of human orthologous missense SNPs. A missense SNP in a non-human species that has matching reference and alternative codons with humans. As shown in FIG. 52, the missense identical variants are missense variants that share matching reference and alternative codon sequences with humans.

As shown in FIGS. 53 and 54, the first enrichment score is produced by determining a ratio of rare synonymous variants with a MAF less than 0.1% over common synonymous variants with a MAF greater than 0.1%. The second enrichment score is produced by determining a ratio of rare missense identical variants with a MAF less than 0.1% over common missense identical variants with a MAF greater than 0.1%. Rare variants include singleton variants.

As shown in FIGS. 53 and 54, a difference between the first enrichment score and the second enrichment score is within a predetermined range, further including accepting the particular non-human primate species for inclusion of missense variants of the particular non-human primate among the benign variants. The difference being in the predetermined range indicates that the missense identical variants are under a same degree of natural selection as the synonymous variants and therefore benign as the synonymous variants.

Figure 55:
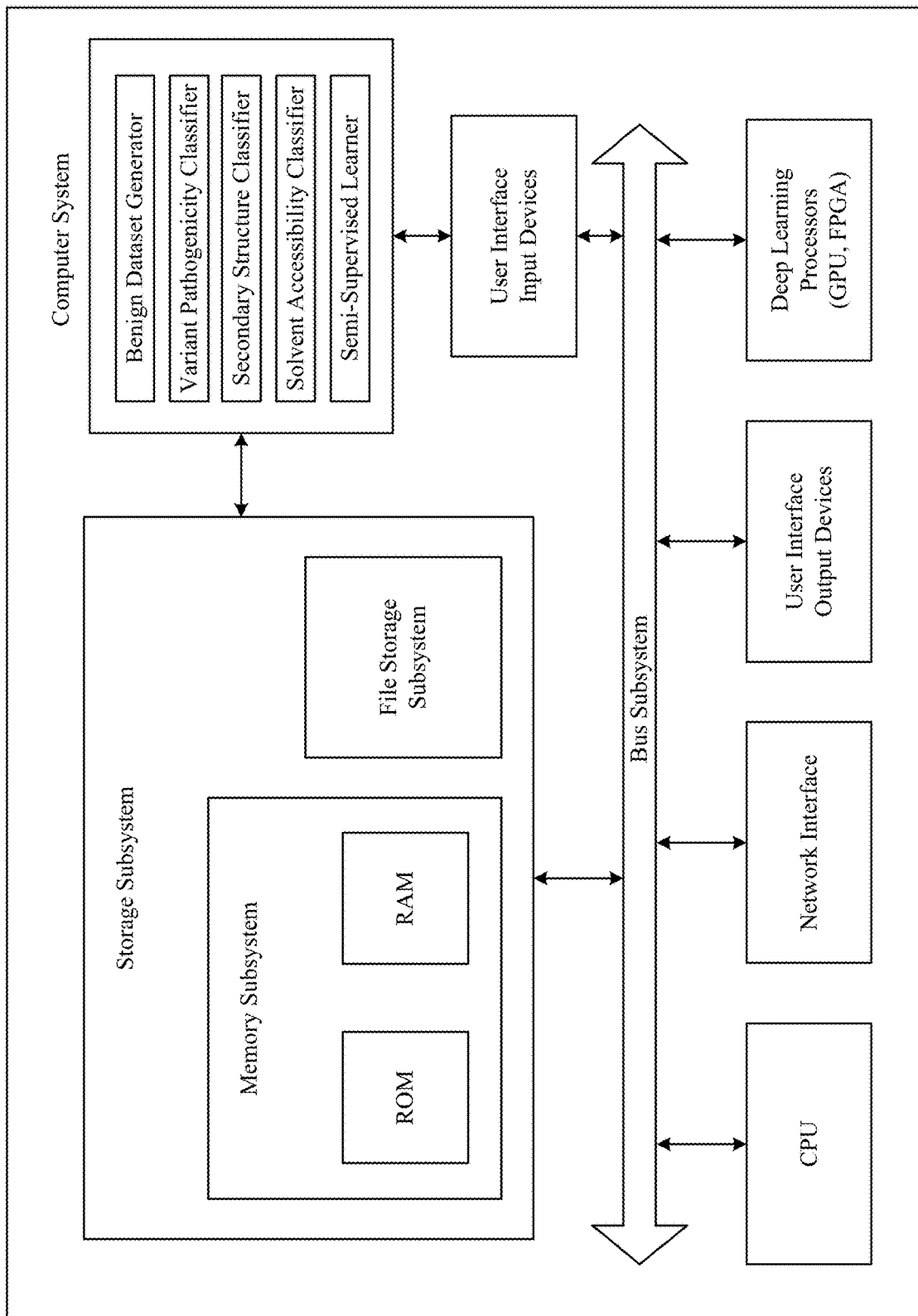
FIG. 55 is a simplified block diagram of a computer system that can be used to implement the technology disclosed.

As shown in FIG. 55, the system repeatedly applies the enrichment analysis to accept a plurality of non-human primate species for inclusion of missense variants of the non-human primate species among the benign variants. The system further includes, a chi-squared test of homogeneity to compare a first enrichment score of synonymous variants and a second enrichment score of missense identical variants for each of the non-human primate species.

As shown in FIG. 55, a count of the non-human primate missense variants is at least 100000. the count of the non-human primate missense variants is 385236. A count of the common human missense variants is at least 50000. The count of the common human missense variants is 83546.

Other implementations may include a non-transitory computer readable storage medium storing instructions executable by a processor to perform actions of the system described above. Yet another implementation may include a method performing actions of the system described above.

Another system implementation of the technology disclosed includes constructing a single nucleotide polymorphism (abbreviated SNP) pathogenicity classifier. The system trains a convolutional neural network-based SNP pathogenicity classifier, which runs on numerous processors coupled to memory, using benign training examples and pathogenic training examples of amino acid sequences expressed by benign SNPs and pathogenic SNPs. The benign training examples include first and second sets of nucleotide sequences, expressed as amino acid sequence pairs, each amino acid sequence including a central amino acid flanked by upstream and downstream amino acids. Each amino acid sequence pair includes a reference sequence of amino acids expressed by a reference nucleotide sequence and an alternative sequence of amino acids expressed by an alternative nucleotide sequence containing a SNP.

Figure 23:
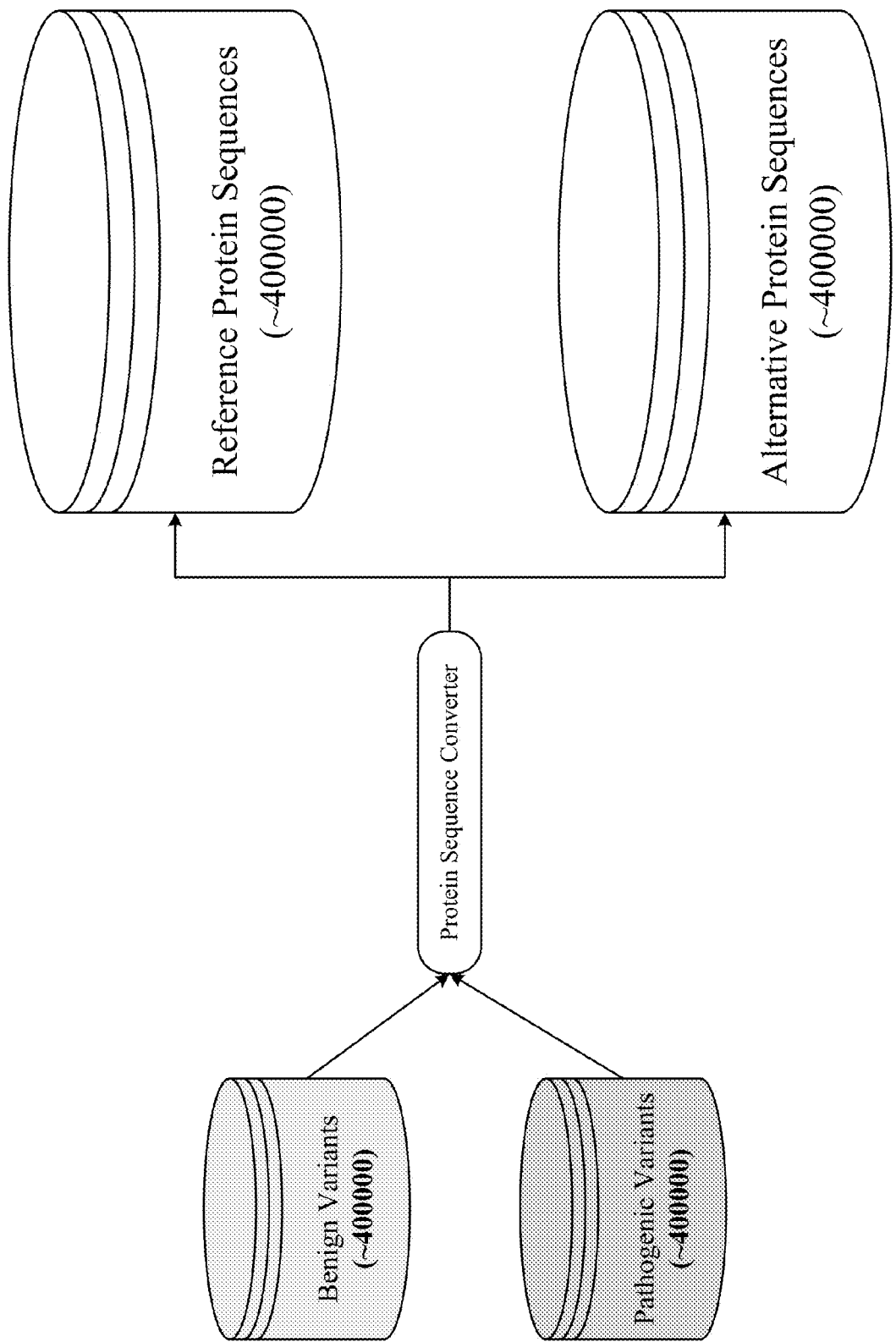
FIG. 23 depicts one implementation of generating reference and alternative protein sequences from benign and pathogenic variants.

As shown in FIG. 23, the first set comprises human nucleotide sequence pairs, with each pair including a human alternative nucleotide sequence containing a SNP and having a minor allele frequency (abbreviated MAF) deemed to be common within a human population. The second set comprises a non-human primate reference nucleotide sequence paired with a non-human primate alternative nucleotide sequence. The non-human primate reference nucleotide sequence has an orthologous human nucleotide reference sequence. The non-human primate alternative nucleotide sequence contains a SNP.

Each of the features discussed in this particular implementation section for the first system implementation apply equally to this system implementation. As indicated above, all the system features are not repeated here and should be considered repeated by reference.

Other implementations may include a non-transitory computer readable storage medium storing instructions executable by a processor to perform actions of the system described above. Yet another implementation may include a method performing actions of the system described above.

As shown in FIG. 33, a first method implementation of the technology disclosed includes constructing a variant pathogenicity classifier, the method including. The method further includes, training a convolutional neural network-based variant pathogenicity classifier, which runs on numerous processors coupled to memory, using benign training examples and pathogenic training examples of protein sequence pairs generated from benign variants and pathogenic variants. The benign variants include common human missense variants and non-human primate missense variants occurring on alternative non-human primate codon sequences that share matching reference codon sequences with humans.

Each of the features discussed in this particular implementation section for the first system implementation apply equally to this method implementation. As indicated above, all the system features are not repeated here and should be considered repeated by reference.

Other implementations may include a non-transitory computer readable storage medium storing instructions executable by a processor to perform the method described above. Yet another implementation may include a system including memory and one or more processors operable to execute instructions, stored in the memory, to perform the method described above.

As shown in FIG. 33, a second method implementation of the technology disclosed includes constructing a single nucleotide polymorphism (abbreviated SNP) pathogenicity classifier. The method further includes training a convolutional neural network-based SNP pathogenicity classifier, which runs on numerous processors coupled to memory, using benign training examples and pathogenic training examples of amino acid sequences expressed by benign SNPs and pathogenic SNPs. The benign training examples include first and second sets of nucleotide sequences, expressed as amino acid sequence pairs, each amino acid sequence including a central amino acid flanked by upstream and downstream amino acids, and each amino acid sequence pair including a reference sequence of amino acids expressed by a reference nucleotide sequence and an alternative sequence of amino acids expressed by an alternative nucleotide sequence containing a SNP. The first set comprises human nucleotide sequence pairs, with each pair including a human alternative nucleotide sequence containing a SNP and having a minor allele frequency (abbreviated MAF) deemed to be common within a human population. The second set comprises a non-human primate reference nucleotide sequence paired with a non-human primate alternative nucleotide sequence. The non-human primate reference nucleotide sequence has an orthologous human nucleotide reference sequence and the non-human primate alternative nucleotide sequence contains a SNP.

Each of the features discussed in this particular implementation section for the second system implementation apply equally to this method implementation. As indicated above, all the system features are not repeated here and should be considered repeated by reference.

Other implementations may include a non-transitory computer readable storage medium storing instructions executable by a processor to perform the method described above.

Yet another implementation may include a system including memory and one or more processors operable to execute instructions, stored in the memory, to perform the method described above.

We describe systems, methods, and articles of manufacture for using a deep convolutional neural network-based a variant pathogenicity classifier with secondary structure and solvent accessibility classifiers. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

A system implementation of the technology disclosed includes one or more processors coupled to the memory. The memory is loaded with computer instructions to run a deep convolutional neural network-based variant pathogenicity classifier with secondary structure and solvent accessibility classifiers.

The system comprises a first secondary structure subnetwork, running on numerous processors coupled to memory, trained to predict a three-state secondary structure at amino acid locations within a protein sequence. The system further includes a second solvent accessibility subnetwork, running on numerous processors coupled to memory, trained to predict a three-state solvent accessibility at amino acid locations within a protein sequence. A positional frequency matrix (abbreviated PFM) generator, running on at least one of the numerous processors, applied to three sequence groups of primates, mammals, and vertebrates excluding primates and mammals to generate a primate PFM, a mammal PFM, and a vertebrate PFM. An input processor that accepts a variant amino acid sequence with a target variant amino acid flanked upstream and downstream by at least 25 amino acids in each direction, wherein a single nucleotide variant produces the target variant amino acid. A supplemental data allocator, running on at least one of the numerous processors, that allocates a reference amino acid sequence with a target reference amino acid flanked upstream and downstream by at least 25 amino acids in each direction, aligned with the variant amino acid sequence. Following this, it allocates reference state classifications produced by the first and second subnetworks for the reference amino acid sequence. After this the supplemental data allocator allocates variant state classifications produced by the first and second subnetworks for the variant amino acid sequence. Finally, it allocates primate, mammal, and vertebrate PFMs aligned with the reference amino acid sequence.

The system also includes a deep convolutional neural network, running on the numerous processors, trained to classify the variant amino acid sequence as benign or pathogenic based on processing the variant amino acid sequence, the allocated reference amino acid sequence, the allocated reference and variant state classifications, and the allocated PFMs. The system includes an output processor that reports at least a pathogenicity score for the variant amino acid sequence.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

The system comprising the deep convolutional neural network-based variant pathogenicity classifier, further configured to classify the single nucleotide variant as benign or pathogenic based on the pathogenicity score.

The system comprises the deep convolutional neural network-based variant pathogenicity classifier in which the deep convolutional neural network accepts, in parallel, as input at least the variant amino acid sequence, the allocated reference amino acid sequence, the allocated variant secondary structure state classification, the allocated reference secondary structure state classification, the allocated variant solvent accessibility state classification, the allocated reference solvent accessibility state classification, the allocated primate PFM, the allocated mammal PFM, and the allocated vertebrate PFM.

The system is configured to use the batch normalization layers, the ReLU non-linearity layers, and the dimensionality altering layers to pre-process the variant amino acid sequence, the allocated reference amino acid sequence, the allocated primate PFM, the allocated mammal PFM, and the allocated vertebrate PFM. The system is further configured to sum the pre-processed characterizations and concatenate the sums with the allocated variant secondary structure state classification, the allocated reference secondary structure state classification, the allocated variant solvent accessibility state classification, and the allocated reference solvent accessibility state classification to produce a concatenated input. The system processes the concatenated input through a dimensionality altering layer and accept the processed concatenated input to initiate residual blocks of the deep convolutional neural network.

The deep convolutional neural network comprises groups of residual blocks arranged in a sequence from lowest to highest. The deep convolutional neural network is parameterized by a number of residual blocks, a number of skip connections, and a number of residual connections without non-linear activations. The deep convolutional neural network comprises dimensionality altering layers that reshape spatial and feature dimensions of a preceding input.

The system is further configured to train to classify, as pathogenic, a single nucleotide variant that produces a target variant amino acid from a target reference amino acid that is conserved in aligned reference amino acid sequences across primates, mammals, and vertebrates.

The conservation represents functional significance of the target reference amino acid and is determined from the PFWs. The system is further configured to train to classify, as pathogenic, a single nucleotide variant that causes different secondary structures between a variant amino acid sequence and a reference variant amino acid sequence.

The system is further configured to train to classify, as pathogenic, a single nucleotide variant that causes different solvent accessibilities between a variant amino acid sequence and a reference variant amino acid sequence.

A PFM represents conservation of amino acids in a human protein sequence across aligned protein sequences of other species by determining, on a location-by-location basis, frequency of occurrence an amino acid in the human protein sequence across the aligned protein sequences of the other species.

The three states of secondary structure are helix, sheet, and coil. the first secondary structure subnetwork is trained to accept an input protein sequence and primate, mammal, and vertebrate PFMs aligned with amino acid locations within the input protein sequence, and predict the three-state secondary structure at each of the amino acid locations. The three states of solvent accessibility are exposed, buried, and intermediate.

The second solvent accessibility subnetwork is trained to accept an input protein sequence and primate, mammal, and vertebrate PFMs aligned with amino acid locations within the input protein sequence, and predict the three-state solvent accessibility at each of the amino acid locations. The input protein sequence is a reference protein sequence. The input protein sequence is an alternative protein sequence. The first secondary structure subnetwork comprises groups of residual blocks arranged in a sequence from lowest to highest. The first secondary structure subnetwork is parameterized by a number of residual blocks, a number of skip connections, and a number of residual connections without non-linear activations.

The first secondary structure subnetwork comprises dimensionality altering layers that reshape spatial and feature dimensions of a preceding input. The second solvent accessibility subnetwork comprises groups of residual blocks arranged in a sequence from lowest to highest. The second solvent accessibility subnetwork is parameterized by a number of residual blocks, a number of skip connections, and a number of residual connections without non-linear activations. The second solvent accessibility subnetwork comprises dimensionality altering layers that reshape spatial and feature dimensions of a preceding input.

Each residual block comprises at least one batch normalization layer, at least one rectified linear unit (abbreviated ReLU) layer, at least one dimensionality altering layer, and at least one residual connection. Each residual block comprises two batch normalization layers, two ReLU non-linearity layers, two dimensionality altering layers, and one residual connection.

The deep convolutional neural network, the first secondary structure subnetwork, and the second solvent accessibility subnetwork each comprise an ultimate classification layer. The ultimate classification layer is a sigmoid-based layer. The ultimate classification layer is a softmax-based layer.

The system is further configured to ablate ultimate classification layers of the first secondary structure subnetwork and the second solvent accessibility subnetwork for collaboration with the deep convolutional neural network.

The system is further configured to, during training of the deep convolutional neural network, further train the first secondary structure subnetwork and the second solvent accessibility subnetwork on pathogenicity classification, including back propagating errors to the subnetworks and updating subnetwork weights.

The second solvent accessibility subnetwork comprises at least on atrous convolution layer. The system is further configured to classify developmental delay disorder (abbreviated DDD)-causing variants as pathogenic. The variant amino acid sequence and the reference amino acid sequence share flanking amino acids. The system is further configured to use one-hot encoding to encode inputs to the deep convolutional neural network.

Figure 15:
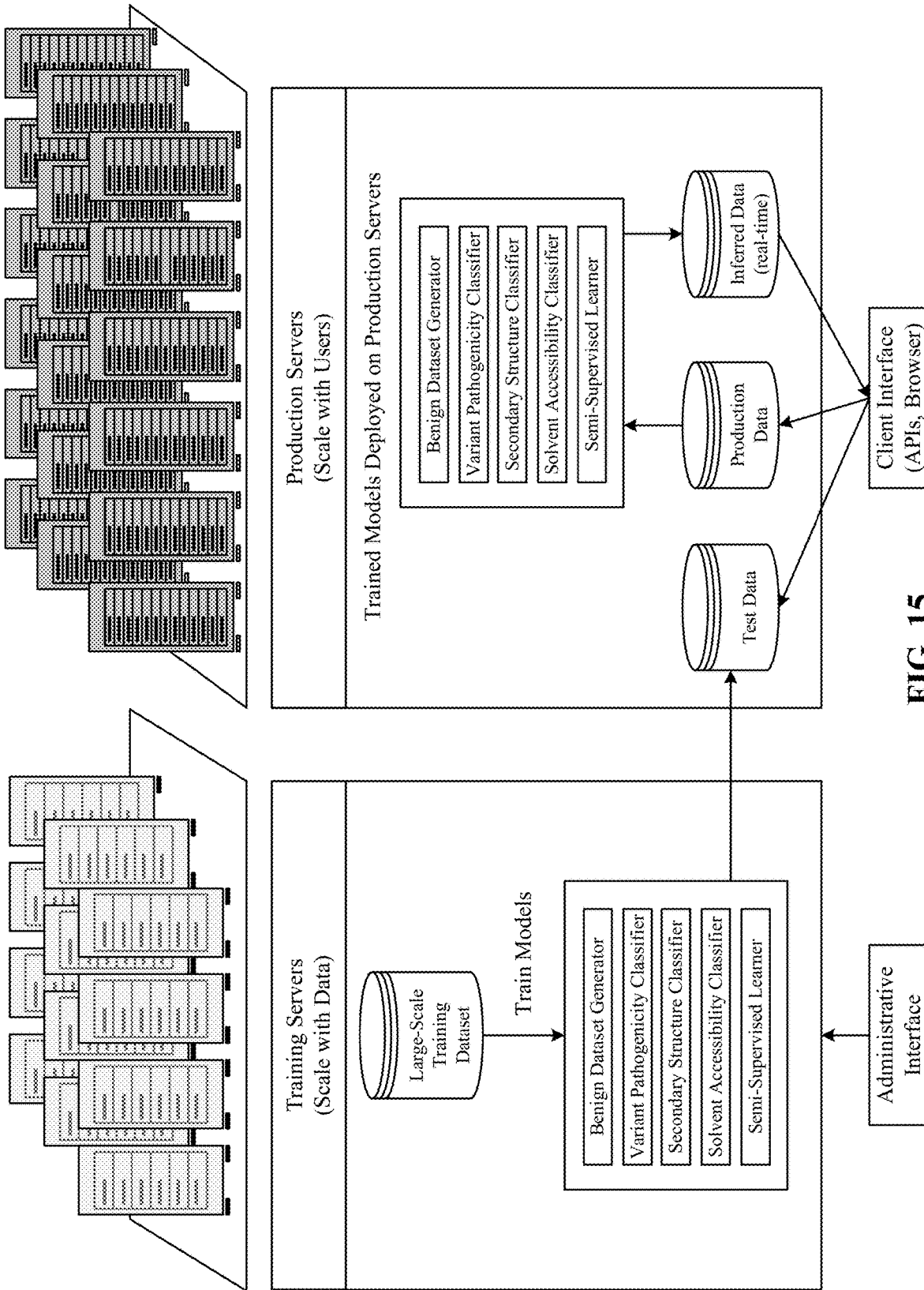
FIG. 15 shows an example computing environment in which the technology disclosed can be operated.

FIG. 15 shows an example computing environment in which the technology disclosed can be operated. The deep convolutional neural network, the first secondary structure subnetwork, and the second solvent accessibility subnetwork are trained on one or more training servers. The trained deep convolutional neural network, the first trained secondary structure subnetwork, and the trained second solvent accessibility subnetwork are deployed on one or more production servers that receive input sequences from requesting clients. The production servers process the input sequences through at least one of the deep convolutional neural network, the first secondary structure subnetwork, and the second solvent accessibility subnetwork to produce outputs that are transmitted to the clients.

Other implementations may include a non-transitory computer readable storage medium storing instructions executable by a processor to perform actions of the system described above. Yet another implementation may include a method performing actions of the system described above.

Another system implementation of the technology disclosed includes a deep convolutional neural network-based variant pathogenicity classifier, running on numerous processors coupled to memory. The system includes, a positional frequency matrix (abbreviated PFM) generator, running on at least one of the numerous processors, applied to two sequence groups of primates and mammals to generate a primate PFM and a mammal PFM. The system also includes an input processor that accepts a variant amino acid sequence with a target variant amino acid flanked upstream and downstream by at least 25 amino acids in each direction, wherein a single nucleotide variant produces the target variant amino acid. The system also includes a supplemental data allocator, running on at least one of the numerous processors, that allocates a reference amino acid sequence with a target reference amino acid flanked upstream and downstream by at least 25 amino acids in each direction, aligned with the variant amino acid sequence. It also allocates primate and mammal PFMs aligned with the reference amino acid sequence. The system further includes a deep convolutional neural network, running on the numerous processors, trained to classify the variant amino acid sequence as benign or pathogenic based on processing the variant amino acid sequence, the allocated reference amino acid sequence, and the allocated PFMs. Finally, the system includes, an output processor that reports at least a pathogenicity score for the variant amino acid sequence.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

The system is further configured to classify the single nucleotide variant as benign or pathogenic based on the pathogenicity score. The deep convolutional neural network, in parallel, accepts and processes the variant amino acid sequence, the allocated reference amino acid sequence, the allocated primate PFM, and the allocated mammal PFM. The system is further configured to train to classify, as pathogenic, a single nucleotide variant that produces a target variant amino acid from a target reference amino acid that is conserved in reference amino acid sequences across primates and mammals. The conservation represents functional significance of the target reference amino acid and is determined from the PFWs.

Each of the features discussed in this particular implementation section for the first system implementation apply equally to this system implementation. As indicated above, all the system features are not repeated here and should be considered repeated by reference.

Other implementations may include a non-transitory computer readable storage medium storing instructions executable by a processor to perform actions of the system described above. Yet another implementation may include a method performing actions of the system described above.

A first method implementation of the technology disclosed includes running a first secondary structure subnetwork on numerous processors coupled to memory, trained to predict a three-state secondary structure at amino acid locations within a protein sequence. Running a second solvent accessibility subnetwork on numerous processors coupled to memory, trained to predict a three-state solvent accessibility at amino acid locations within a protein sequence. Running on at least one of the numerous processors. a positional frequency matrix (abbreviated PFM) generator, applied to three sequence groups of primates, mammals, and vertebrates excluding primates and mammals to generate a primate PFM, a mammal PFM, and a vertebrate PFM. Accepting a variant amino acid sequence an input processor with a target variant amino acid flanked upstream and downstream by at least 25 amino acids in each direction. A single nucleotide variant produces the target variant amino acid. Running on at least one of the numerous processors, a supplemental data allocator that allocates a reference amino acid sequence with a target reference amino acid flanked upstream and downstream by at least 25 amino acids in each direction, aligned with the variant amino acid sequence. It also allocates reference state classifications produced by the first and second subnetworks for the reference amino acid sequence. It further allocates variant state classifications produced by the first and second subnetworks for the variant amino acid sequence. It allocates primate, mammal, and vertebrate PFMs aligned with the reference amino acid sequence. Running on the numerous processors, a deep convolutional neural network trained to classify the variant amino acid sequence as benign or pathogenic based on processing the variant amino acid sequence, the allocated reference amino acid sequence, the allocated reference and variant state classifications, and the allocated PFMs. Reporting at least a pathogenicity score for the variant amino acid sequence through an output processor.

Each of the features discussed in this particular implementation section for the first system implementation apply equally to this method implementation. As indicated above, all the system features are not repeated here and should be considered repeated by reference.

Other implementations may include a non-transitory computer readable storage medium storing instructions executable by a processor to perform the method described above. Yet another implementation may include a system including memory and one or more processors operable to execute instructions, stored in the memory, to perform the method described above.

A second method implementation of the technology disclosed includes running on numerous processors coupled to memory, a deep convolutional neural network-based variant pathogenicity classifier. Running a positional frequency matrix (abbreviated PFM) generator on at least one of the numerous processors, applied to two sequence groups of primates and mammals to generate a primate PFM and a mammal PFM. Accepting in an input processor, a variant amino acid sequence with a target variant amino acid flanked upstream and downstream by at least 25 amino acids in each direction. A single nucleotide variant produces the target variant amino acid. Running a supplemental data allocator on at least one of the numerous processors, that allocates a reference amino acid sequence with a target reference amino acid flanked upstream and downstream by at least 25 amino acids in each direction, aligned with the variant amino acid sequence and allocates primate and mammal PFMs aligned with the reference amino acid sequence. Running a deep convolutional neural network on the numerous processors, trained to classify the variant amino acid sequence as benign or pathogenic based on processing the variant amino acid sequence, the allocated reference amino acid sequence, and the allocated PFMs. Reporting at least a pathogenicity score for the variant amino acid sequence in an output processor.

Each of the features discussed in this particular implementation section for the second system implementation apply equally to this method implementation. As indicated above, all the system features are not repeated here and should be considered repeated by reference.

Other implementations may include a non-transitory computer readable storage medium storing instructions executable by a processor to perform the method described above. Yet another implementation may include a system including memory and one or more processors operable to execute instructions, stored in the memory, to perform the method described above.

Yet another system implementation of the technology disclosed includes a system that generates large-scale pathogenic training data for training a single nucleotide polymorphism (abbreviated SNP) pathogenicity classifier.

As shown in FIG. 33, the system trains the SNP pathogenicity classifier, which runs on numerous processors coupled to memory, using a training set of benign SNPs and a training set of elite predicted pathogenic SNPs that are culled from a synthetic set of combinatorically generated SNPs.

As shown in FIGS. 44, 45, 46, 47, 48, and 49, the system builds the elite set iteratively in cycles, beginning with no predicted SNPs and accumulating a full set of predicted SNPs by culling outlier SNPs from the synthetic set. The synthetic set comprises pseudo-pathogenic SNPs that are combinatorically generated SNPs not present in the benign set and decrease in set membership as the outlier SNPs are iteratively culled from the synthetic set for inclusion in the elite set.

As shown in FIGS. 44, 45, 46, 47, 48, and 49, the system trains and applies an ensemble of SNP pathogenicity classifiers to cull the outlier SNPs from the synthetic set, iteratively in cycles. This includes training the ensemble using a common training set of benign SNPs, a common training set of elite predicted pathogenic SNPs, and separate training sets of pseudo-pathogenic SNPs sampled from the synthetic set without replacement. This also includes applying the trained ensemble to cull the outlier SNPs from the synthetic set and accumulate culled outlier SNPs in the common elite set by applying the trained ensemble to score at least some SNPs from the synthetic set that were not used for training the ensemble in a current cycle and using the scores to select, from the scored SNPs, current cycle outlier SNPs to accumulate in the common elite set.

As shown in FIGS. 44, 45, 46, 47, 48, and 49, the system then stores in memory, classifier parameters derived by the training, a common elite set completed over the cycles and within a predetermined spread of the common benign set, and the common benign set for training the SNP pathogenicity classifier.

As shown in FIGS. 44, 45, 46, 47, 48, and 49, the elite predicted pathogenic SNPs are top 5% of the SNPs predicted by the ensemble. In some implementations, they are fixed number of top-scored SNPs, such as 20000.

The SNP pathogenicity classifier and the ensemble of SNP pathogenicity classifiers are each deep convolutional neural networks (abbreviated DCNN). The ensemble includes 4 to 16 DCNNs. As shown in FIGS. 44, 45, 46, 47, 48, and 49, the ensemble includes 8 DCNNs.

As shown in FIGS. 44, 45, 46, 47, 48, and 49, the system trains the ensemble of DCCNs in epochs during the cycles, concluding the training for a particular cycle when predictions on a validation sample form discrete probability distribution clusters of benign and pathogenic predictions.

As shown in FIGS. 44, 45, 46, 47, 48, and 49, the system uses the scores to select the current cycle outlier SNPs by summing scores from the ensemble of DCCNs.

As shown in FIGS. 44, 45, 46, 47, 48, and 49, the system uses the scores to select the current cycle outlier SNPs by taking a maximum mean value for each of the SNPs scored by the ensemble of DCNNs.

As shown in FIGS. 44, 45, 46, 47, 48, and 49, the sampling without replacement during a current cycle results in disjoint separate training sets of pseudo-pathogenic SNPs during the current cycle.

The system continues the cycles until a termination condition is reached. The termination condition can be a predetermined number of cycles. As shown in 44, 45, 46, 47, 48, and 49, the predetermined number of cycles is 21.

As shown in FIGS. 44, 45, 46, 47, 48, and 49, the termination condition is when an elite predicted pathogenic set size is within a predetermined spread of a benign set size.

The classifier parameters can be at least convolution filter weights and learning rate.

The system can select one of the SNP pathogenicity classifiers in the ensemble as the SNP pathogenicity classifier. The selected SNP pathogenicity classifier can be the one that outpredicted other SNP pathogenicity classifiers in the ensemble on a validation sample evaluated in an ultimate cycle.

As shown in FIGS. 44, 45, 46, 47, 48, and 49, the common elite set completed over the cycles can have at least 400000 elite predicted pathogenic SNPs.

As shown in FIGS. 44, 45, 46, 47, 48, and 49, the system, in each cycle, can match trinucleotide context between the benign SNPs and the sampled pseudo-pathogenic SNPs to prevent mutation rate bias in the elite predicted pathogenic SNPs.

As shown in FIGS. 44, 45, 46, 47, 48, and 49, the sampling of pseudo-pathogenic SNPs from the synthetic set can decrease by 5% in each successive cycle.

As shown in FIGS. 44, 45, 46, 47, 48, and 49, the system can filter the synthetic SNPs scored in the current cycle by pseudo-pathogenic SNPs sampled in the current cycle for training, the elite predicted pathogenic SNPs, and the benign SNPs used in the current cycle for training.

Each of the features discussed in this particular implementation section for the first system implementation apply equally to this system implementation. As indicated above, all the system features are not repeated here and should be considered repeated by reference.

Other implementations may include a non-transitory computer readable storage medium storing instructions executable by a processor to perform actions of the system described above. Yet another implementation may include a system including memory and one or more processors operable to execute instructions, stored in the memory, to perform actions of the system described above.

Figure 43:
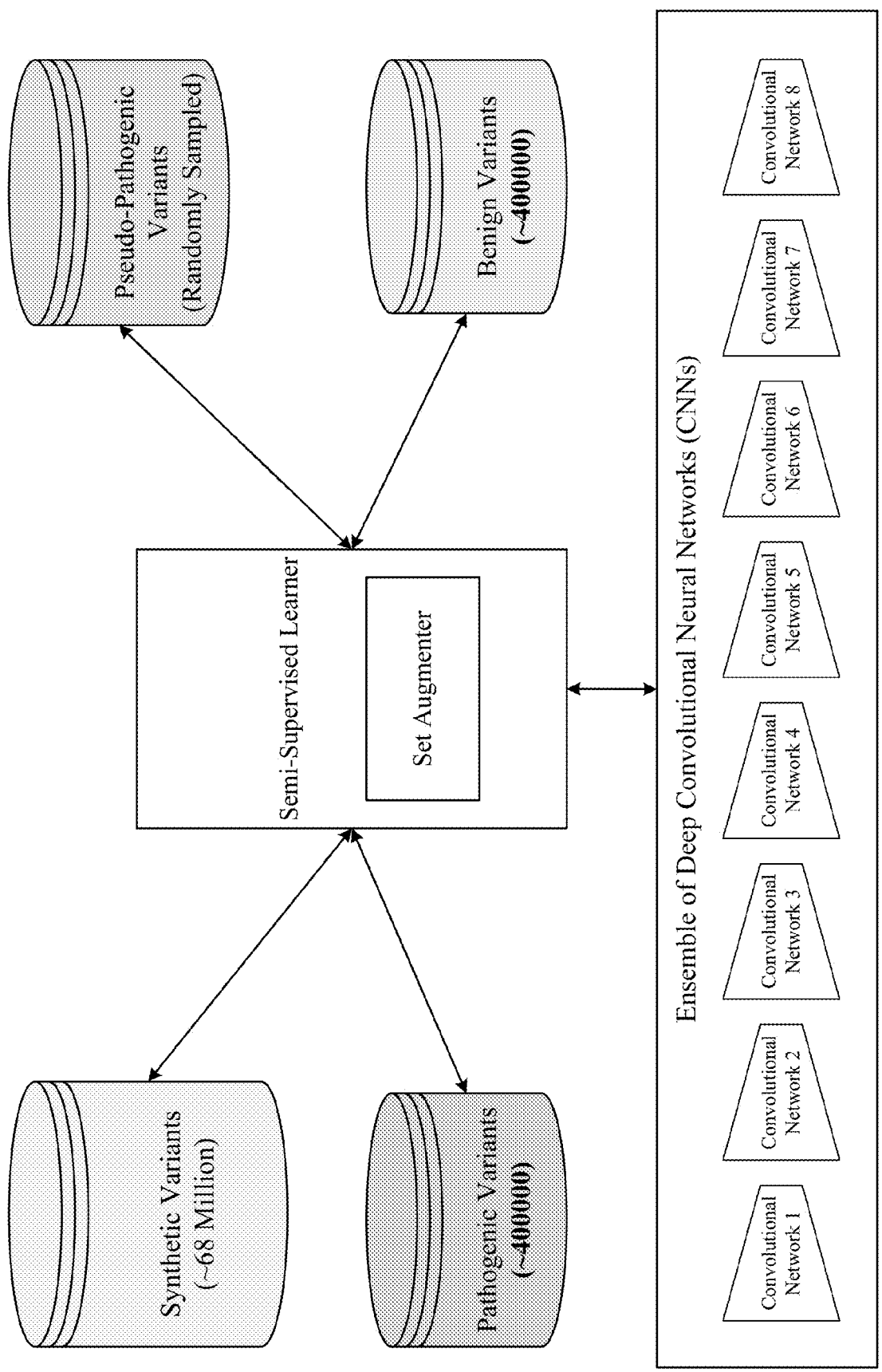
FIG. 43 shows a computing environment of the disclosed semi-supervised learner.
Figure 44:
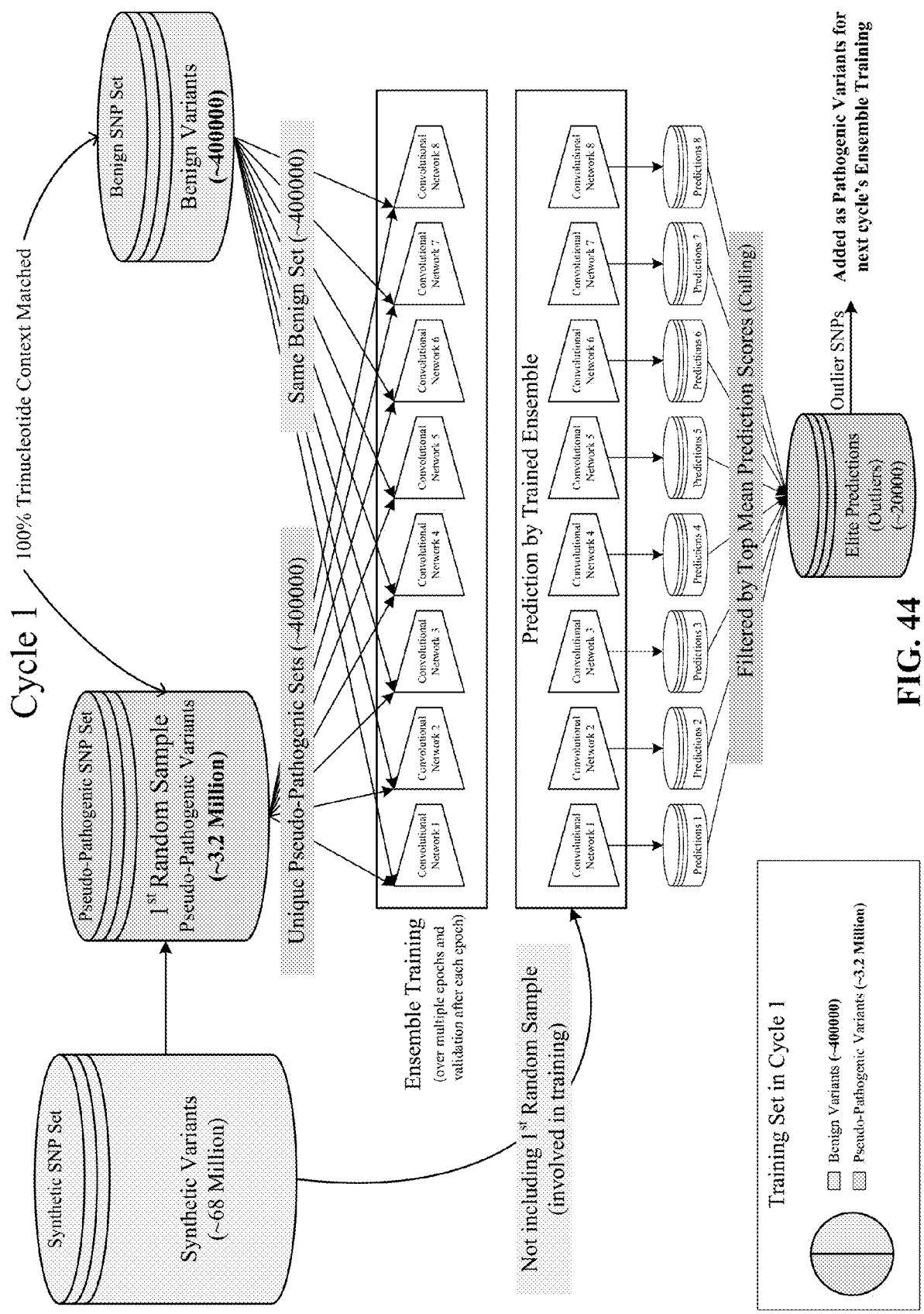
FIGS. 44, 45, 46, 47, and 48 show various cycles of the disclosed semi-supervised learning.
Figure 45:
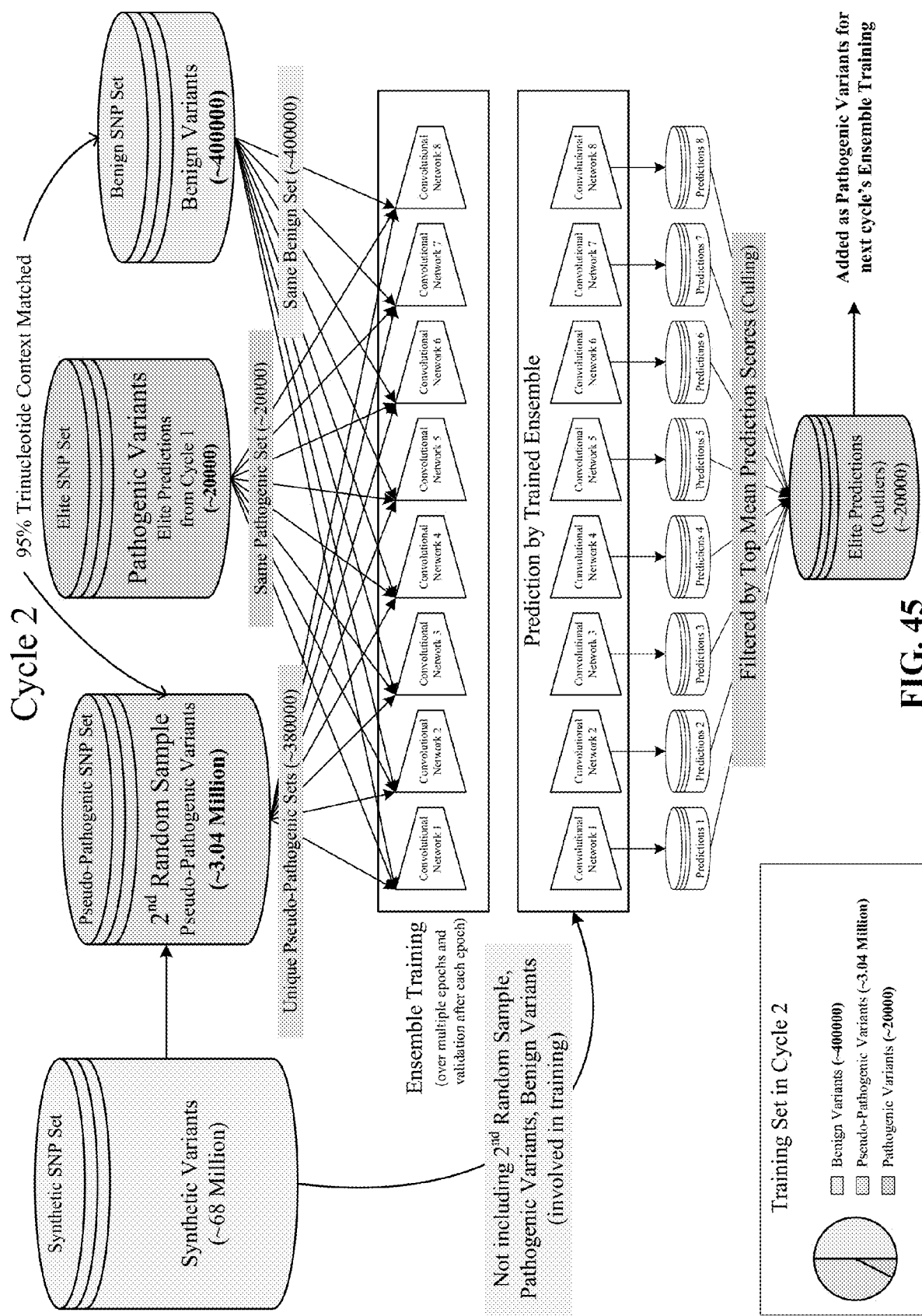
Figure 46:
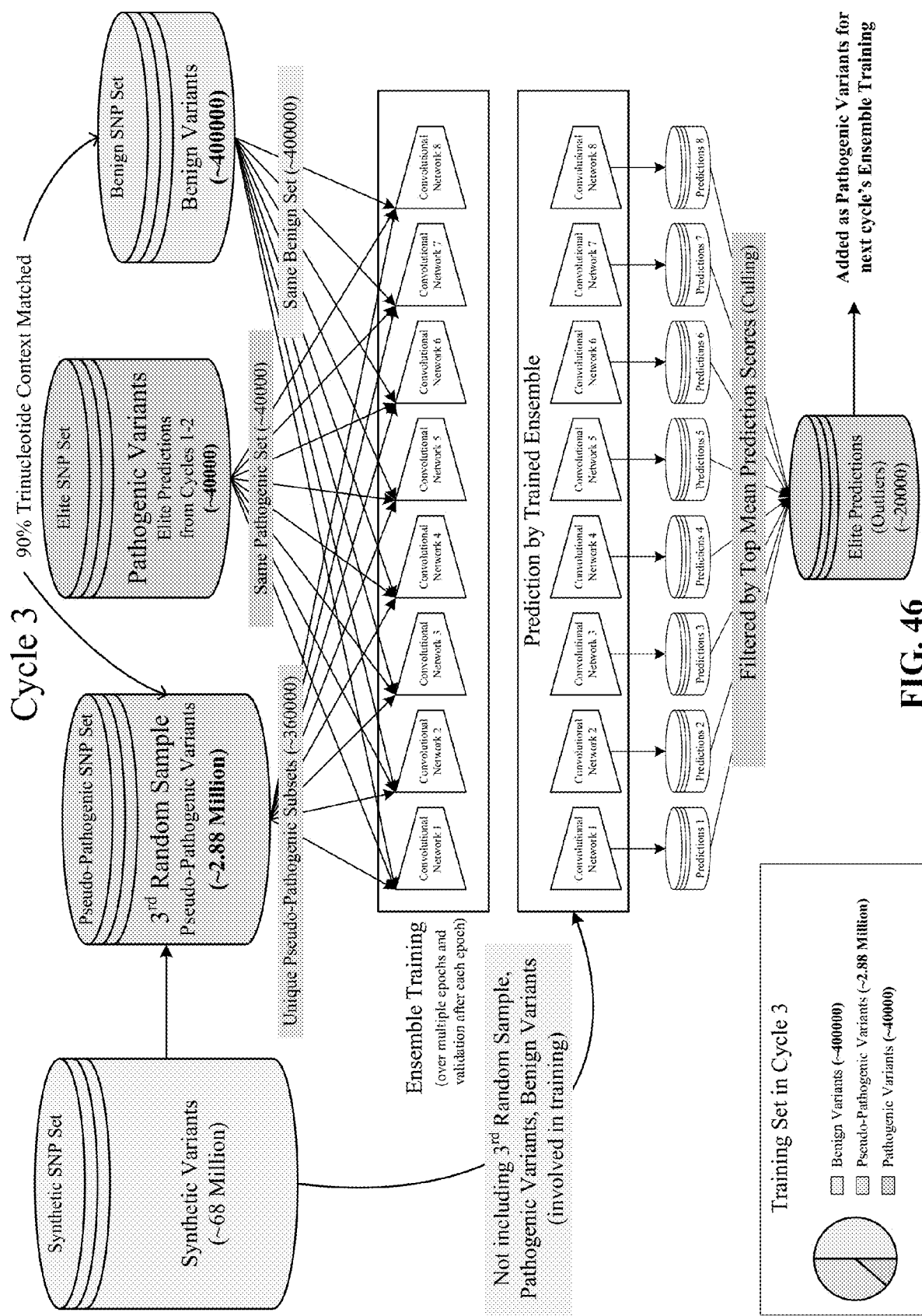
Figure 47:
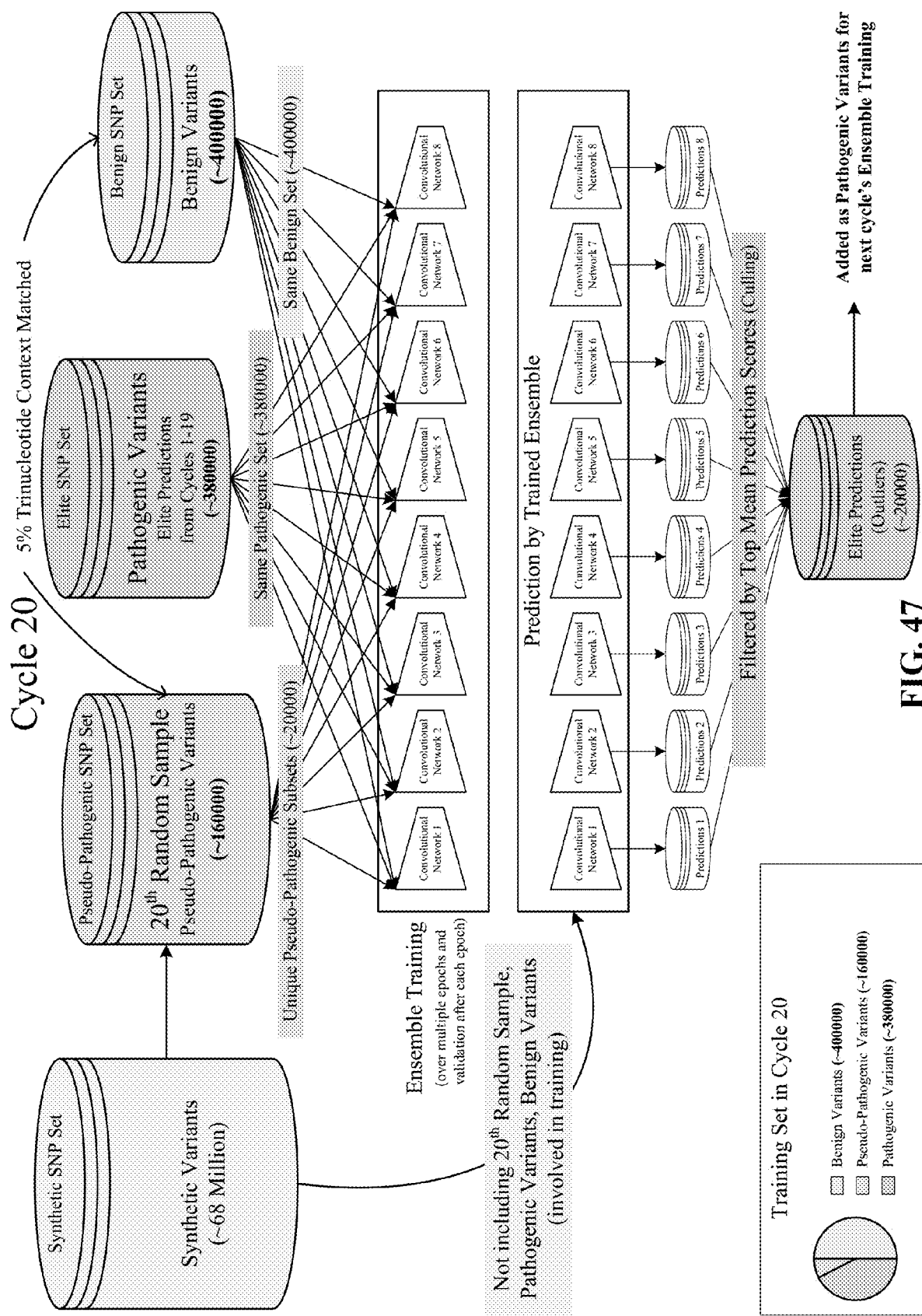
Figure 48:
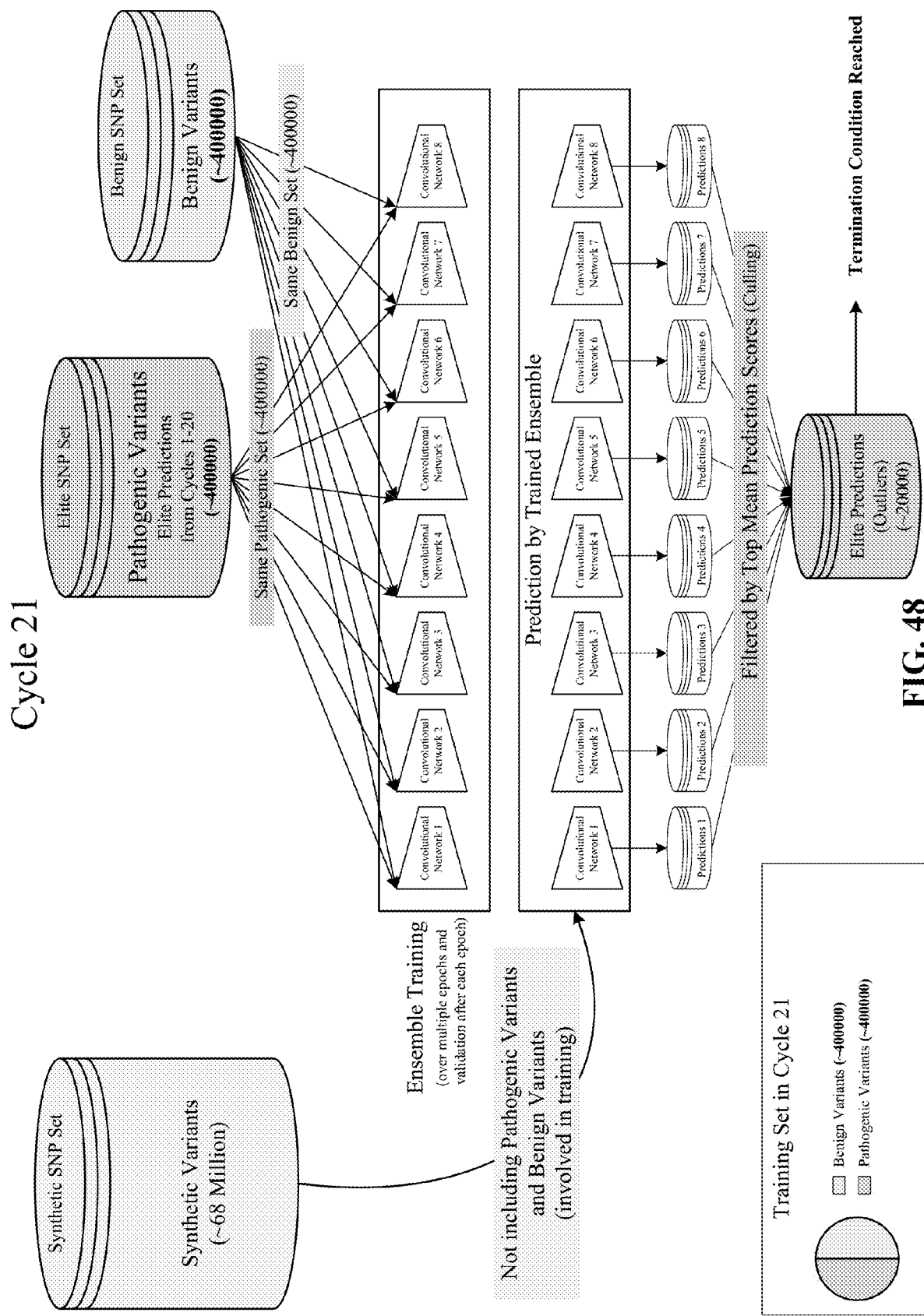
Figure 49:
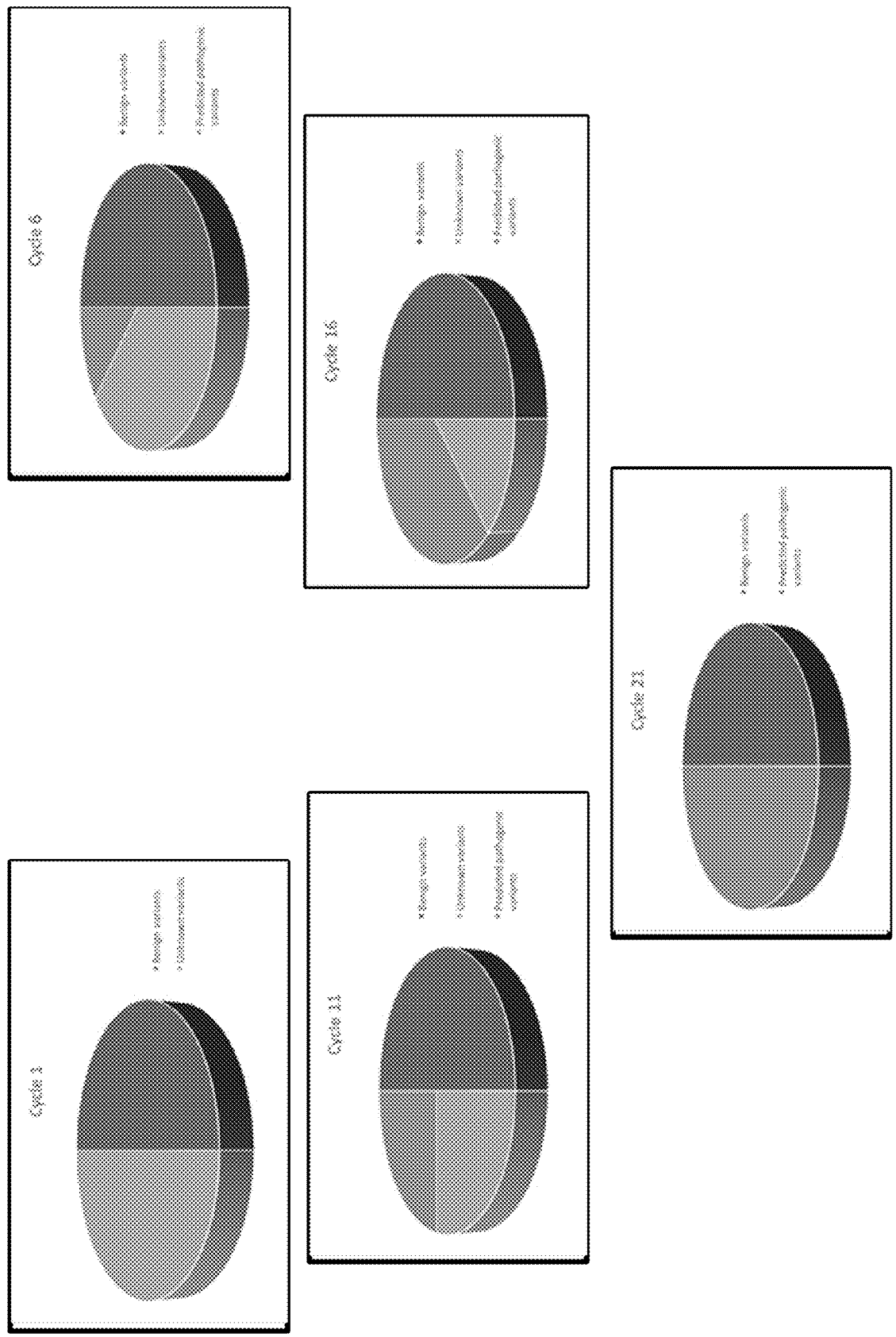
FIG. 49 is an illustration of the iterative balanced sampling process.

Yet another implementation of the technology disclosed includes a convolutional neural network (abbreviated CNN)-based semi-supervised learner, as shown in FIG. 43.

As shown in FIG. 43, the semi-supervised learner can include an ensemble of CNNs, running on numerous processors coupled to memory, that is iteratively trained on a benign training set and a pathogenic training set.

As shown in FIG. 43, the semi-supervised learner can include a set augmenter, running on at least one of the processors, that progressively augments a set size of the pathogenic training set based on the trained ensemble's evaluation of a synthetic set;

In each iteration, the evaluation produces an elite predicted pathogenic set that is added to the pathogenic training set by the set augmenter.

The semi-supervised learner can include a builder that uses at least one of the CNNs, an augmented pathogenic training set, and the benign training set to construct and train a single nucleotide polymorphism (abbreviated SNP) pathogenicity classifier.

Each of the features discussed in this particular implementation section for the first system implementation apply equally to this system implementation. As indicated above, all the system features are not repeated here and should be considered repeated by reference.

Other implementations may include a non-transitory computer readable storage medium storing instructions executable by a processor to perform actions of the system described above. Yet another implementation may include a system including memory and one or more processors operable to execute instructions, stored in the memory, to perform actions of the system described above.

The preceding description is presented to enable the making and use of the technology disclosed. Various modifications to the disclosed implementations will be apparent, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein. The scope of the technology disclosed is defined by the appended claims.

Computer System

FIG. 55 is a simplified block diagram of a computer system that can be used to implement the technology disclosed. Computer system typically includes at least one processor that communicates with a number of peripheral devices via bus subsystem. These peripheral devices can include a storage subsystem including, for example, memory devices and a file storage subsystem, user interface input devices, user interface output devices, and a network interface subsystem. The input and output devices allow user interaction with computer system. Network interface subsystem provides an interface to outside networks, including an interface to corresponding interface devices in other computer systems.

In one implementation, the neural networks such as benign dataset generator, variant pathogenicity classifier, secondary structure classifier, solvent accessibility classifier, and semi-supervised learner are communicably linked to the storage subsystem and user interface input devices.

User interface input devices can include a keyboard; pointing devices such as a mouse, trackball, touchpad, or graphics tablet; a scanner; a touch screen incorporated into the display; audio input devices such as voice recognition systems and microphones; and other types of input devices.

In general, use of the term "input device" is intended to include all possible types of devices and ways to input information into computer system.

User interface output devices can include a display subsystem, a printer, a fax machine, or non-visual displays such as audio output devices. The display subsystem can include a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system to the user or to another machine or computer system.

Storage subsystem stores programming and data constructs that provide the functionality of some or all of the modules and methods described herein. These software modules are generally executed by processor alone or in combination with other processors.

Memory used in the storage subsystem can include a number of memories including a main random access memory (RAM) for storage of instructions and data during program execution and a read only memory (ROM) in which fixed instructions are stored. A file storage subsystem can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem in the storage subsystem, or in other machines accessible by the processor.

Bus subsystem provides a mechanism for letting the various components and subsystems of computer system communicate with each other as intended. Although bus subsystem is shown schematically as a single bus, alternative implementations of the bus subsystem can use multiple busses.

Computer system itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system depicted in FIG. 55 is intended only as a specific example for purposes of illustrating the technology disclosed. Many other configurations of computer system are possible having more or less components than the computer system depicted in FIG. 55.

The deep learning processors can be GPUs or FPGAs and can be hosted by a deep learning cloud platforms such as Google Cloud Platform, Xilinx, and Cirrascale. Examples of deep learning processors include Google's Tensor Processing Unit (TPU), rackmount solutions like GX4 Rackmount Series, GX8 Rackmount Series, NVIDIA DGX-1, Microsoft' Stratix V FPGA, Graphcore's Intelligent Processor Unit (IPU), Qualcomm's Zeroth platform with Snapdragon processors, NVIDIA's Volta, NVIDIA's DRIVE PX, NVIDIA's JETSON TX1/TX2 MODULE, Intel's Nirvana, Movidius VPU, Fujitsu DPI, ARM's DynamicIQ, IBM TrueNorth, and others.

What is claimed is:

1. A variant pathogenicity classifier, comprising:
a recurrent neural network which runs on numerous processors coupled to memory and is trained to determine pathogenicity of variants;
wherein the recurrent neural network is trained using, as input, benign training example pairs and pathogenic training example pairs of reference protein sequences and alternative protein sequences;
wherein the alternative protein sequences are generated from benign variants and pathogenic variants;
wherein the benign variants include common human missense variants and non-human primate missense variants occurring on alternative non-human primate codon sequences that share matching reference codon sequences with humans; and
wherein the recurrent neural network is trained to capture long-range dependencies in the reference protein sequences and in the alternative protein sequences.

2. The variant pathogenicity classifier of claim 1, wherein the recurrent neural network is a long short-term memory (LSTM) network.

3. The variant pathogenicity classifier of claim 2, wherein the recurrent neural network is a gated recurrent unit (GRU) network.

4. The variant pathogenicity classifier of claim 1, wherein the recurrent neural network is a multi-dimensional recurrent neural network.

5. A variant pathogenicity classifier, comprising:
a recurrent neural network which runs on numerous processors coupled to memory and is trained to determine pathogenicity of variants;
wherein the recurrent neural network is trained using, as input, benign training example pairs and pathogenic training example pairs of reference protein sequences and alternative protein sequences;
wherein the alternative protein sequences are generated from benign variants and pathogenic variants; and
wherein the benign variants include common human missense variants and non-human primate missense variants occurring on alternative non-human primate codon sequences that share matching reference codon sequences with humans.

6. The variant pathogenicity classifier of claim 5, wherein the recurrent neural network is a long short-term memory (LSTM) network.

7. The variant pathogenicity classifier of claim 5, wherein the recurrent neural network is a gated recurrent unit (GRU) network.

8. The variant pathogenicity classifier of claim 5, wherein the recurrent neural network is a multi-dimensional recurrent neural network.

9. A system, comprising:
a variant pathogenicity classifier which runs on numerous processors coupled to memory and is trained to determine pathogenicity of variants;
wherein the variant pathogenicity classifier is trained using, as input, benign training example pairs and pathogenic training example pairs of reference protein sequences and alternative protein sequences;
wherein the alternative protein sequences are generated from benign variants and pathogenic variants; and
wherein the benign variants include common human missense variants and non-human primate missense variants occurring on alternative non-human primate codon sequences that share matching reference codon sequences with humans.

10. The system of claim 9, wherein the variant pathogenicity classifier is a recurrent neural network.

11. The system of claim 10, wherein the variant pathogenicity classifier captures long-range dependencies in the reference protein sequences and in the alternative protein sequences.

12. The system of claim 11, wherein the variant pathogenicity classifier is a long short-term memory (LSTM) network.

13. The system of claim 11, Wherein the variant pathogenicity classifier is a gated recurrent unit (GRU) network.

14. The system of claim 11, wherein the variant pathogenicity classifier is a multi-dimensional recurrent neural network.

15. The system of claim 9, Wherein the variant pathogenicity classifier is a deep spatio-temporal neural network.

16. The system of claim 9, wherein the variant pathogenicity classifier uses convolutional auto-encoders.

* * * * *

UNITED STATES PATENT AND TRADEMARK OFFICE
CERTIFICATE OF CORRECTION

PATENT NO. : 11,386,324 B2
APPLICATION NO. : 16/773678
DATED : July 12, 2022
INVENTOR(S) : Hong Gao et al.

It is certified that error appears in the above-identified patent and that said Letters Patent is hereby corrected as shown below:

In the Specification

Column 1, Line 22, delete "Networks," and insert -- Networks (CNNs), --.

Column 1, Line 29, before "and" delete "1000-3/IP-1613-PRV);".

In the Claims

In Claim 3, Column 60, Line 19, delete "2," and insert -- 1, --.

In Claim 13, Column 61, Line 8, delete "Wherein" and insert -- wherein --.

In Claim 15, Column 61, Line 13, delete "Wherein" and insert -- wherein --.

Signed and Sealed this
Twenty-fifth Day of October, 2022

Katherine Kelly Vidal
*Director of the United States Patent and Trademark Office*